United States Patent
Revazova et al.

(10) Patent No.: US 9,920,299 B2
(45) Date of Patent: *Mar. 20, 2018

(54) PATIENT-SPECIFIC STEM CELL LINES DERIVED FROM HUMAN PARTHENOGENETIC BLASTOCYSTS

(71) Applicant: INTERNATIONAL STEM CELL CORPORATION, Carlsbad, CA (US)

(72) Inventors: Elena S. Revazova, Santa Monica, CA (US); Leonid N. Kuzmichev, Moscow (RU); Nickolay A. Turovets, Carlsbad, CA (US); Jeffrey D. Janus, San Ramon, CA (US)

(73) Assignee: International Stem Cell Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/951,199

(22) Filed: Nov. 24, 2015

(65) Prior Publication Data
US 2016/0186133 A1 Jun. 30, 2016

Related U.S. Application Data

(62) Division of application No. 12/082,028, filed on Apr. 7, 2008, now abandoned.

(60) Provisional application No. 60/922,244, filed on Apr. 6, 2007.

(51) Int. Cl.
*A61K 35/545* (2015.01)
*C12N 5/0735* (2010.01)
*C12N 5/075* (2010.01)

(52) U.S. Cl.
CPC .......... *C12N 5/0606* (2013.01); *A61K 35/545* (2013.01); *C12N 5/0609* (2013.01); *C12N 2500/02* (2013.01); *C12N 2500/14* (2013.01); *C12N 2501/115* (2013.01); *C12N 2501/235* (2013.01); *C12N 2502/1323* (2013.01)

(58) Field of Classification Search
CPC C12N 5/0606; C12N 5/0609; C12N 2500/02; C12N 2500/14; C12N 2501/115; C12N 2501/235; C12N 2502/1323; A61K 35/545
See application file for complete search history.

(56) References Cited

U.S. PATENT DOCUMENTS

| | | | |
|---|---|---|---|
| 5,004,681 A | 4/1991 | Boyse et al. | |
| 7,732,202 B2 | 6/2010 | Revazova et al. | |
| 8,420,393 B2 * | 4/2013 | Revazova | C12N 5/0606 435/366 |
| 2003/0027331 A1 * | 2/2003 | Yan | C12N 5/0606 435/366 |
| 2004/0091936 A1 | 5/2004 | West | |
| 2007/0141702 A1 * | 6/2007 | Revazova | C12N 5/0606 435/366 |
| 2010/0069251 A1 | 3/2010 | Kim et al. | |

FOREIGN PATENT DOCUMENTS

| | | |
|---|---|---|
| CN | 1778906 A | 5/2006 |
| WO | WO 89/04168 A1 | 5/1989 |
| WO | WO 2003/020983 A1 | 3/2003 |
| WO | WO 2007/047947 A2 | 4/2007 |
| WO | WO 2007/047979 A2 | 4/2007 |

OTHER PUBLICATIONS

Chinese Office Action with Search Report dated Feb. 8, 2017, regarding CN 201510018547.9.
Brevini et al.: "*Parthenotes as a source of embryonic stem cells*"; Cell Proliferation 41(Suppl. 1), 20-30, Feb. 2008.
Hochberg et al., "*A novel rapid single nucleotide polymorphism (SNP)-based method for assessment of hematopoietic chimerism after allogeneic stem cell transplantation*", Blood, 101(1):363-369 (Epub Aug. 29, 2002) (2003) Abstract.
Hwang et al.: "*Patient-specific embryonic stem cells derived from human SCNT blastocysts*"; Science, 1-11, May 2005.
Kastenberg et al.: "*Alternative Sources of Pluripotency: Science, Ethics, and Stem Cells*"; Transplantation Reviews 22(3), 215-222, Jul. 2008.
Kim et al.: "*Recombination Signatures Distinguish Embryonic Stem Cells Derived by Parthenogenesis and Somatic Cell Nuclear Transfer*"; Cell Stem Cell, 1: 346-352, 2007.
Kono, T. et al.: "*Birth of parthenogenetic mit that mn develop to aduithota*"; Nature 428,(6985), 860-864, Apr. 22, 2004.
Lin et al.: "*Multilineage Potential of Homozygous Stem Cells Derived from Metaphase II Oocytes*"; Stem Cells, 21: 152-161, 2003.
NIH: Stem Cells: Scientific Progress and Future Research Directions, 2001, Chapter 2, pp. 5-10.
Revazova et al., "HLA homozygous stem cell lines derived from human parthenogenetic blastocysts", Cloning Stem Cells, 10(1):11-24 (2008).
Revazova et al., "Patient-specific stem cell lines derived from human parthenogenetic blastocysts", *Cloning Stem Cells*, 9(3):432-49 (2007).
Spinola et al.: "*Distribution of HLA alleles in Portugal and Cabo Verde: Relationships with the slave trade route*"; Ann. Hum. Genetics., 66: 285-296, 2002.
Vrana et al.: "*Nonhuman primate parthenogenetic stem cells*", Pro. Nat. Acad. Sci., 100:11911-11916 (2003).

* cited by examiner

*Primary Examiner* — Thaian N Ton
(74) *Attorney, Agent, or Firm* — DLA Piper LLP (US)

(57) ABSTRACT

Methods are disclosed for generating HLA homozygous parthenogenetic human stem cell (hpSC-Hhom) lines from both HLA homozygous and HLA heterozygous donors. These hpSC-Hhom lines demonstrate typical human embryonic stem cell morphology, expressing appropriate stem cell markers and possessing high levels of alkaline phosphatase and telomerase activity. Additionally, injection of these cell lines into immunodeficient animals leads to teratoma formation. Furthermore, in the case of HLA heterozygous donors, the hpSC-Hhom lines inherit the haplotype from only one of the donor's parents. SNP data analysis suggests that hpSC-Hhom lines derived from HLA heterozygous oocyte donors are homozygous throughout the genome as assessed by single-nucleotide polymorphism (SNP) analysis. The protocol as disclosed minimizes the use of animal-derived components, which makes the stem cells more practical for clinical application.

8 Claims, 12 Drawing Sheets

PATIENT-SPECIFIC STEM CELL LINES DERIVED FROM HUMAN PARTHENOGENETIC BLASTOCYSTS

RELATED APPLICATIONS

This application is a divisional application of U.S. patent application Ser. No. 12/082,028 filed Apr. 7, 2008 which claims benefit of U.S. Provisional Application No. 60/922,244, filed Apr. 6, 2007, which are herein incorporated by reference in their entirety.

INCORPORATION OF SEQUENCE LISTING

The material in the accompanying sequence listing is hereby incorporated by reference into this application. The accompanying sequence listing text file, name ISCC1150_2_Sequence_Listing.txt, was created on Feb. 8, 2016, and is 3 kb. The file can be assessed using Microsoft Word on a computer that uses Windows OS.

BACKGROUND OF THE INVENTION

Field of the Invention

The present invention relates generally to embryonic stems cells, and more specifically to a process for obtaining HLA homozygous parthenogenetic human stem cell lines for cell-based therapy.

Background Information

The first human embryonic stem cells (ESC) were derived from a blastocyst inner cell mass (ICM) obtained from a fertilized oocyte, capable of infinite division and differentiation into cells of all tissues types. The embryonic stem cell is a potentially limitless source of pluripotent cells for transplant-based cell therapies.

Human embryonic stem cells (ES) cells are pluripotent cells that can differentiate into a large array of cell types. When injected into immune-deficient mice, embryonic stem cells form differentiated tumors (teratomas). However, embryonic stem cells that are induced in vitro to form embryoid bodies (EBs) provide a source of embryonic stem cell lines that are amenable to differentiation into multiple cell types characteristic of several tissues under certain growth conditions. For example, ES cells become differentiated into neurons in the presence of nerve growth factor and retinoic acid.

Human embryonic stem cells have the potential to give significant therapeutic benefit to patients, provided that the problem of immune rejection can be solved. Embryonic stem cells that are genetically related to the recipient may overcome such rejection problems. Currently, human embryonic stem cells (hES) are derived from three sources: blastocysts remaining after infertility treatments and donated for research, blastocysts generated from donated gametes (oocytes and sperm), and the products of nuclear transfer (NT). Cadaveric fetal tissue is the only source of human embryonic germ cells (hEG). hES and hEG cells offer remarkable scientific and therapeutic possibilities, involving potential for generating more specialized cells or tissues. Ethical concerns about the sources of hES and hEG cells, however, and fears that use of NT for research could lead to use of NT to produce a human being, have fostered a great deal of public discussion and debate.

Parthenogeneic activation of mammalian oocytes may be used as an alternative to fertilization by sperm/NT to prepare oocytes for embryonic stem cell generation. Parthenogeneic activation is the production of embryonic cells, with or without eventual development into an adult, from a female gamete in the absence of any contribution from a male gamete.

Parthenogenetic activation of oocytes is a relatively simple method to create histocompatible stem cells in comparison to SCNT, because it does not require the complex equipment necessary to micromanipulate an oocyte. Parthenogenetic stem cells are produced from unfertilized oocytes and contain genetic material exclusively from the oocyte donor (the potential patient). Further, following directed cell differentiation, autologous cells may be transplanted without the threat of immune rejection. Parthenogenetic mouse MHC-homozygous stem cell lines and one parthenogenetic primate heterozygous embryonic stem cell line (Cyno-1) have already been derived and cell pluripotency has been demonstrated in these lines.

As stated above, the greatest risk posed with allogeneic tissue and organ transplantation is that of immune rejection. The degree of risk is proportional to the degree of disparity between donor and recipient cell-surface antigen-presenting proteins. In the ideal transplant, donor tissue is histocompatible with the recipient at the major histocompatibility complex (MHC). The human leukocyte antigen (HLA) system is the nomenclature designating the human MHC, and represents antigens important for transplantation. Matching donor and recipient tissue for HLA antigens reduces the chance of a cytotoxic T-cell response in the recipient, and thus greatly increases the likelihood of transplant survival.

MHC class I and II HLA haplotypes are specific sets of HLA-A, -B, -DR locus alleles inherited together from a parent. Despite a high degree of HLA polymorphism, there are only 200 common HLA haplotypes in existence within the U.S. Caucasian population. This HLA diversity, in combination with a heterozygous selection coefficient, means that the chance of finding a donor-recipient match ranges from one in 1000 to one in several million due to the unique tissue type provided by the combination of these allelic variants in the heterozygous individual.

Transplant-based stem cell therapies face the same HLA matching issues that limit solid organ allogeneic transplants due to immune rejection. HLA-matched stem cell lines may overcome the risk of immune rejection. For parthenogeneic derived cells, HLA heterozygous cell lines are derived from HLA heterozygous donors by activating oocytes using a combination of A23187 and 6-DMAP. Since these cells are HLA-matched with the oocyte donor, their ability to provide tissue-matched derivatives is limited.

MHC compatibility between a donor and recipient increases significantly if the donor cells are HLA homozygous; i.e. contain identical alleles for each antigen-presenting protein. Furthermore, if homozygous donor cells have a haplotype found with high frequency in a population, these cells may have application in transplantation-based stem cell therapies for a large number of individuals.

SUMMARY OF THE INVENTION

The present invention discloses methods for generating HLA homozygous parthenogenetic human stem cell (hpSC-Hhom) lines from both HLA homozygous and HLA heterozygous donors. These hpSC-Hhom lines demonstrate human embryonic stem cell morphology, expressing typical stem cell markers (i.e., SSEA-3, SSEA-4, TRA-1-60, TRA-1-81, and OCT-4) and possessing high levels of alkaline phosphatase and telomerase activity. Additionally, injection of these cell lines into immunodeficient animals leads to teratoma formation. SNP data analysis demonstrates that hpSC-Hhom lines derived from HLA heterozygous oocyte donors are homozygous throughout the genome. The protocol as disclosed minimizes the use of animal-derived components, which makes these stem cells ideally suited for clinical application.

In one embodiment, an isolated human stem cell line derived from parthenogeneic blastocysts is disclosed, where at least one cell comprising the cell line is heterozygous for one or more single nucleotide polymorphisms (SNPs), homozygous for one or more HLA alleles, or includes a combination of homozygous and heterozygous SNPs.

In one aspect, at least one cell is homozygous for HLA alleles. In another aspect, at least one cell forms a teratoma when transplanted into an immunocompromised mouse. In a further aspect, at least one cell is MHC compatible with the blastocyst donor.

In a related aspect, at least one cell is MHC compatible with a first degree blood relative of the blastocyst donor, including that at least one cell is substantially genetically imprinted according to donor origin.

In one aspect, at least one cell (i) will proliferate in an in vitro culture for over one year, (ii) maintains the potential to differentiate to derivatives of endoderm, mesoderm, and ectoderm tissues throughout the culture, and (iii) is inhibited from differentiation when cultured on a fibroblast feeder layer.

In another aspect, at least one cell differentiates into a cell including a neuronal cell, a cardiac cell, a smooth muscle cell, a striated muscle cell, an endothelial cell, an osteoblast, and oligodendrocyte, a hematopoietic cell, an adipose cell, a stromal cell, a chondrocyte, an astrocyte, a keratinocyte, a pancreatic islet cell, a lymphoid precursor cell, a mast cell, a mesodermal cell, and an endodermal cell. In a related aspect, at least one cell does not have the capacity to form a viable organism.

In another embodiment, a method of treating a subject in need thereof is disclosed, including administering a cellular composition comprising differentiated cells, where the differentiated cells are derived from a stem cell line derived from parthenogeneic blastocysts, where at least one cell comprising the cell line is heterozygous for one or more single nucleotide polymorphisms (SNPs), homozygous for one or more HLA alleles, or includes a combination of homozygous and heterozygous SNPs.

In one aspect, the subject presents a disease including Parkinson's disease, Huntington's disease, Alzheimer's disease, ALS, spinal cord defects or injuries, multiple sclerosis, muscular dystrophy, cystic fibrosis, liver disease, diabetes, heart disease, macular degeneration, cartilage defects or injuries, burns, foot ulcers, vascular disease, urinary tract disease, AIDS, and cancer.

In one embodiment, a library of stem cells including autologous or allogenic stem cells is disclosed, where the stem cells are derived from parthenogenetically activated oocytes from one or more human donors, and where the stem cells are HLA homozygous stem cells. In one aspect, each library member is identified as a full sibling, half sibling, or unrelated according to single nucleotide polymorphism (SNP) markers. In another aspect, each library member is characterized according to HLA-type and the library member is HLA-matched to potential recipients for therapeutic use.

In another aspect, the oocyte donor is histocompatible with a member of the library. In a related aspect, a member of the library is genomically imprinted according to the oocyte donor origin, including that the stem cells of the library may be derived from an HLA heterozygous oocyte donor. In a further aspect, each member of the library is homozygous for a different combination of MHC/HLA alleles than the other members of the library.

In one aspect, each member of the library is at least homozygous for one or more HLA class I genes and HLA class II genes. In a related aspect, the HLA class I genes include HLA A*, HLA B*, HLA and Cw* haplotype combinations. In another related aspect, the HLA class II genes include HLA DRB1*, DRB3*, DRB4*, DRB5*, DQA1*, and DQB1* haplotype combinations.

In another embodiment, a method of generating HLA homozygous stem cells is disclosed including screening oocyte donors for HLA-haplotypes found commonly in a given population group, incubating human metaphase II oocytes in in vitro fertilization (IVF) media, incubating the cells in IVF media including an ionophore, incubating the cells in IVF media including puromycin, and incubating the cells in fresh IVF medium, where one or more incubations are carried out under differential $O_2$ tension and where inner cell masses (ICM) obtained from cells produce culturable stem cells.

Exemplary methods and compositions according to this invention are described in greater detail below.

DETAILED DESCRIPTION OF THE INVENTION

Figure 1:
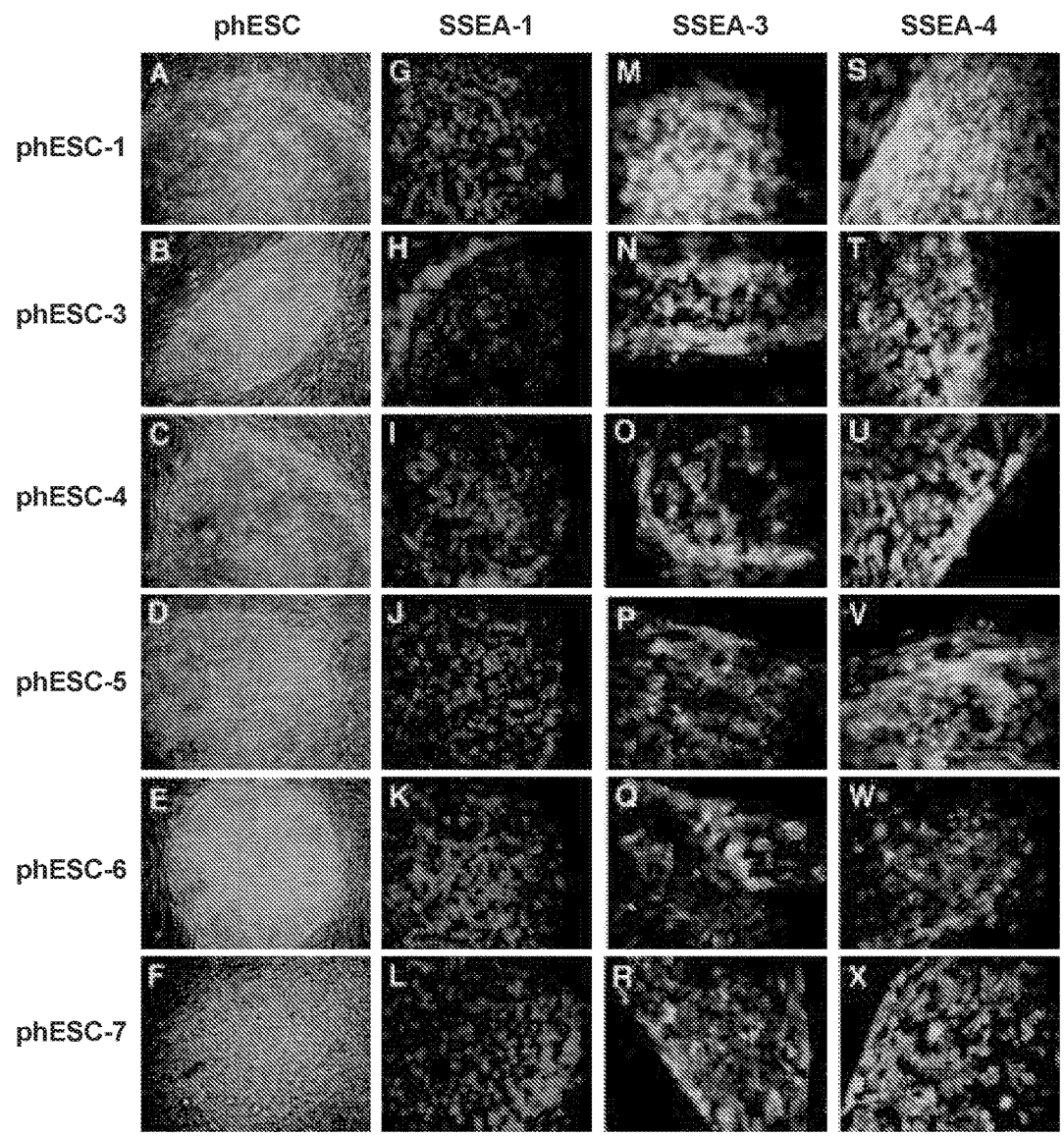
FIG. 1 shows specific markers characteristic for phESC lines. Undifferentiated colonies of phESC on human feeder layer cells (A-F), negative staining for SSEA-1 (G-L), expression of cell surface markers SSEA-3 (M-R), SSEA-4 (S-X). Magnification (A) to (E) ×100; (F) ×200; (G) to (X) ×400. Alkaline phosphatase positive staining of phESC colonies on feeder cells (A-F), OCT-4 (G-L), TRA-1-60 (K-R) and TRA-1-81 (S-X). Magnification (A, B, O, R) ×100; (C-F, M, S, X) ×200; (G-L, N, P, Q, T-W) ×400.
Figure 1:
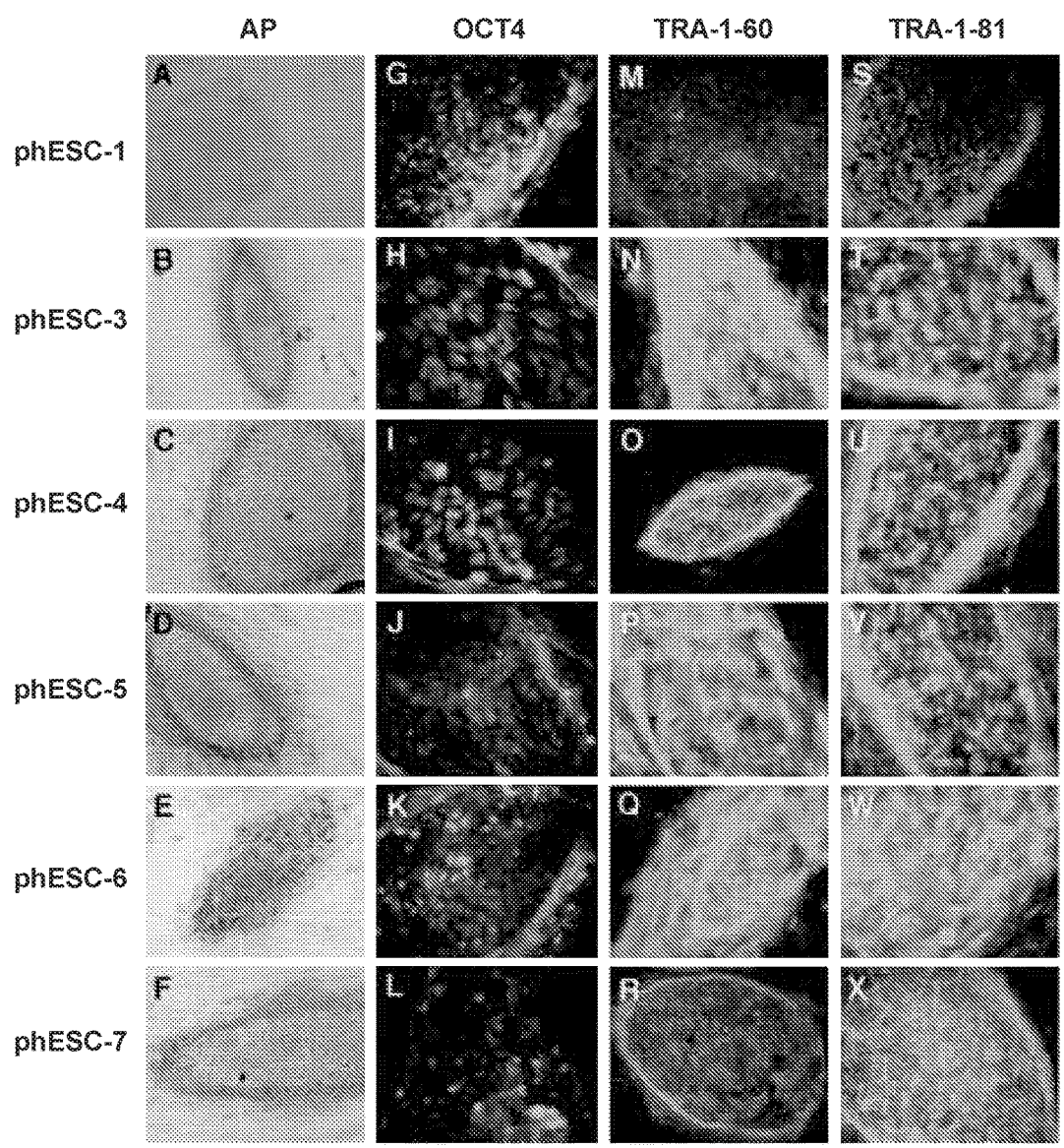

Before the present composition, methods, and culturing methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The present invention discloses at least two different approaches for deriving human HLA homozygous parthenogenetic stem cell lines useful for transplantation-based stem cell therapies.

In one embodiment, one cell line is derived from an HLA homozygous donor, including using A23187 and 6-DMAP during oocyte activation, blocking extrusion of the 2nd polar body, and thereby retaining all of the genetic material of the MII oocyte. The HLA genotype of stem cells derived from these oocytes matched that of the donor (Revazova et al., Cloning Stem Cells (2007) 9(3):432-449). In a related aspect, a diploid hpSC-Hhom-1 line from an HLA homozygous donor may also be obtained.

In another embodiment, HLA homozygous embryonic stem cells may be derived from HLA heterozygous oocyte donors, including using parthenogenetic activation of oocytes with a combination of A23187 and puromycin which allows for extrusion of the 2nd polar body. The activated oocyte therefore contained only half of a set of metaphase II chromosomes, which allowed formation of a homozygous genotype. For example, 80 percent of human oocytes activated by a combination of calcium ionophore and puromycin display a pronucleus with the extrusion of the second polar body. Further, cytogenetic analysis demonstrates that 78 percent contain a normal haploid set of chromosomes (Yamano S. et al, J Med Investigation (2000) 47(1-2):1-8). Moreover, human oocytes activated with A23187 and puromycin displayed one pronucleus and two polar bodies with a haploid set of chromosomes (Nakagawa K., et al., Zygote (2001) 9:83-88). Such a pronuclear parthenote with a normal set of haploid chromosomes has been developed in mouse models. (Nakasaka H. et al., Zygote (2000) 8:203-208).

Using such a protocol results in multiple diploid cell lines from oocytes isolated from HLA heterozygous donors (e.g., but not limited to, hpSC-Hhom-2, hpSC-Hhom-3, hpSC-Hhom-4).

While not being bound by theory, HLA genotyping data suggests that the HLA haplotype is inherited exclusively from one of the donor's parents. SNP analysis data suggests that these three cell lines are homozygous throughout the genome as assessed by SNP analysis. For example, exemplar cell lines disclosed in the present invention (see, Example 1) have a diploid karyotype, which corresponds to earlier work in which diploid stem cell lines were derived from haploid mouse embryos (Kaufman et al., J Embryol Exp Morphol (1983) 73:249-261).

The exact mechanism and timing of duplication of haploid genetic material following oocyte activation is unclear, however, while not being bound by theory, DNA replication seems to occur in the absence of cell cleavage or division. Prior studies suggest that 80% of parthenogenetically activated mouse oocytes preserve their haploid state until the morula stage, with subsequent stem cell lines derived from these embryos becoming diploid (Kaufman M. H. et al., 1983, supra).

Aside from replacement therapy, a repository of cells and tissues derived from hpSC-Hhom lines may be invaluable in the treatment of genetic disorders. According to the Online Mendelian Inheritance in Man (OMIM), John Hopkins University and the National Center for Biotechnology Information (NCBI) there are more than 100 genetic disorders, with the list continuing to expand. Examples include Alzheimer's disease, diabetes, Graves disease, hemophilia, Huntington's disease, muscular dystrophy, Parkinson's disease, sickle cell anemia, Phenylketonuria-PKU and Severe Combined Immune Deficiency (SCID). In these situations, it would be important to use cell lines obtained from donors not carrying the same genetic defect.

"Differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

"Gynogenesis" refers to the production of an embryo containing a discernible trophectoderm and inner cell mass that results upon activation of a cell, such as an oocyte, or other embryonic cell type, containing mammalian DNA of all female origin, preferably human female origin, e.g., human or non-human primate oocyte DNA. Such female mammalian DNA may be genetically modified, e.g., by insertion, deletion or substitution of at least one DNA sequence, or may be unmodified. For example, the DNA may be modified by the insertion or deletion of desired coding sequences, or sequences that promote or inhibit embryogenesis. Typically, such an embryo will be obtained by in vitro activation of an oocyte that contains DNA of all female origin. Gynogenesis is inclusive of parthenogenesis which is defined below. It also includes activation methods where the spermatozoal DNA does not contribute to the DNA in the activated oocyte.

In a related aspect, oocytes are obtained from superovulating subjects prepared for IVF. "Superovulation" techniques, such as treatment of a female subject with hormones, used in IVF are designed to stimulate the ovaries to produce several eggs (oocytes) rather than the usual single egg as in a natural cycle.

The medications required to boost egg production may include, but are not limited to the following: Lupron (gonadotropin releasing hormone-agonist), Orgalutran, Antagon or Cetrotide (gonadotropin releasing hormone-antagonist), Follistim, Bravelle or Gonal-F (FSH, follicle stimulating hormone), Repronex (combination of FSH and LH, luteinizing hormone), and Pregnyl or Novarel (hCG, human chorionic gonadotropin).

In a related aspect, collection of eggs can be performed under transvaginal ultrasound guidance. To accomplish this, a needle is inserted (e.g., under IV sedation) through the vaginal wall into the ovaries using ultrasound to locate each follicle. The follicular fluid is drawn up into a test tube to obtain the eggs.

"Parthenogenesis" ("parthenogenically activated" and "parthenogenetically activated" is used interchangeably) the process by which activation of the oocyte occurs in the absence of sperm penetration, and refers to the development of an early stage embryo comprising trophectoderm and inner cell mass that is obtained by activation of an oocyte or embryonic cell, e.g., blastomere, comprising DNA of all female origin. In a related aspect, a "parthenote" refers to the resulting cell obtained by such activation. In another related aspect, "blastocyst" refers to a cleavage stage of a fertilized or activated oocyte comprising a hollow ball of cells made of outer trophoblast cells and an inner cell mass (ICM). In a further related aspect, "blastocyst formation" refers to the process, after oocyte fertilization or activation, where the oocyte is subsequently cultured in media for a time to enable it to develop into a hollow ball of cells made of outer trophoblast cells and ICM (e.g., 5 to 6 days).

In one embodiment, the process of creating cloned human embryonic stem cell line by parthenogenetically activated oocytes is disclosed. While pathogenesis is not an uncommon form of reproduction in nature, mammals are not known to be capable of this form of reproduction. However, a 10% rate of spontaneous parthenogenesis can be found in oocytes from females of the inbred mouse strain LT/Sv (Hoppe and Illmensee, Proc Natl Acad Sci USA (1982) 79:1912-1916) and spontaneous parthenogenesis also accounts for the formation of hydatitiform moles in humans (Berkowitz and Goldstein, New Eng J Med (1996) 335(23): 1740-1748). Oocytes from placental mammals can be induced to undergo parthenogenesis in vitro; however, embryonic development is unsuccessful.

Following parthenogeneic activation of mammalian oocytes and transfer of the activated oocyte into a surrogate mother, there is limited embryonic survival: ten days in mice; 21 days in sheep; 29 days in pigs; and 11.5 days in rabbits (Kure-bayashi et al., Theriogenology (2000) 53:1105-1119; Hagemann et al., Mol Reprod Dev (1998) 50:154-162; Ozil and Huneau, Development (2001) 128: 917-928; Surani and Barton, Science (1983) 222:1034-1036). The reason for this arrested development is likely due to genetic imprinting. It has been shown that maternal and paternal genomes are epigenetically different and that both sets are required for successful embryonic development (Surani, Cell (1998) 93:309-312; Sasaki et al., (1992) 6:1843-1856). While not being limited by theory, in parthenotes, all of the genetic material should be of maternal origin, a therefore should lack paternal imprinting. Paternal imprinting is thought to be responsible for extra-embryo tissue development, thus the development of trophoblastic tissue following fertilization of an enucleated oocyte (Surani and Barton, (1983), supra). In animals, therefore, enucleated zygotes may be useful for nuclear transfer with subsequent parthenogeneic activation.

Mammalian parthenotes undergo only limited development with eventual death of the embryo. In Macao fascicular, only 14 percent of oocytes in stage II metaphase following in vitro parthenogenetic activation developed to the blastocyst stage following 8 days of culture (Vrana et al., Proc Natl Acad Sci USA (2003) 100(Suppl 1): 11911-11916).

Embryos formed in spontaneously activated parthenotes in virgin females of the LT/Sv inbred mouse strain die within a few days. When nuclear transfer is performed from cells comprising the inner cell mass (ICM) of these embryos into fertilized enucleated C57BL/6j mouse oocytes, cloned mice with the LT/Sv genome are obtained (Hoppe and Illmensee, Proc Natl Acad Sci USA (1982) 79:1912-1916). Thus, the use of a fertilized oocyte allows for full-term development of a parthenote. In one aspect, a fertilized enucleated human oocyte can be used to support development of a parthenogenetic embryo containing a donor's nuclei until the blastocyst stage.

"Pluripotent cell" refers to a cell derived from an embryo produced by activation of a cell containing DNA of all female or male origin that can be maintained in vitro for prolonged, theoretically indefinite period of time in an undifferentiated state, that can give rise to different differentiated tissue types, i.e., ectoderm, mesoderm, and endoderm. The pluripotent state of the cells is preferably maintained by culturing inner cell mass or cells derived from the inner cell mass of an embryo produced by androgenetic or gynogenetic methods under appropriate conditions, for example, by culturing on a fibroblast feeder layer or another feeder layer or culture that includes leukemia inhibitory factor (LIF). The pluripotent state of such cultured cells can be confirmed by various methods, e.g., (i) confirming the expression of markers characteristic of pluripotent cells; (ii) production of chimeric animals that contain cells that express the genotype of the pluripotent cells; (iii) injection of cells into animals, e.g., SCID mice, with the production of different differentiated cell types in vivo; and (iv) observation of the differentiation of the cells (e.g., when cultured in the absence of feeder layer or LIF) into embryoid bodies and other differentiated cell types in vitro.

"Diploid cell" refers to a cell, e.g., an oocyte or blastomere, having a diploid DNA content of all male or female origin.

"Haploid cell" refers to a cell, e.g., an oocyte or blastomere, having a haploid DNA content, where the haploid DNA is of all male or female origin.

Activation refers to a process where a fertilized or unfertilized oocyte, for example, but not limited to, in metaphase II of meiosis, undergoes a process typically including separation of the chromatid pairs, extrusion of the second polar body, resulting in an oocyte having a haploid number of chromosomes, each with one chromatid. Activation includes methods whereby a cell containing DNA of all male or female origin is induced to develop into an embryo that has a discernible inner cell mass and trophectoderm, which is useful for producing pluripotent cells but which is itself is likely to be incapable of developing into a viable offspring. Activation may be carried out, for example, under one of the following conditions: (1) conditions that do not cause second polar body extrusion; (ii) conditions that cause polar body extrusion but where the polar body extrusion is inhibited; or (iii) conditions that inhibit first cell division of the haploid oocyte.

"Metaphase II" refers to a stage of cell development where the DNA content of a cell consists of a haploid number of chromosomes with each chromosome represented by two chromatids. For the present invention, the suppression of the second meiotic division after parthenogenetic activation of human metaphase II oocytes and the generation of diploid embryos led to the derivation of MHC-heterozygous phESC.

In general, the oxygen tension in a mammal oviduct and uterus is much less than half of that found in the normal atmosphere (Fischer and Bavister, J Reprod Fertil (1993) 99:673-679; Kaufman et al., Comp. Biochme Physiol Comp Physiol (1994) 107:673-678). For successful culture of human embryos after IVF, oxygen concentrations of 20% as well as 5% have been used. However, increased oxygen can generate reactive oxygen species that can induce apoptosis (Van Soom et al., Theriogeology (2002) 57:1453-1465). It has been reported that low oxygen concentration increases the viability of preimplantation embryos, assists their normal development and gives higher incidence of the formation of healthy blastocysts as indicated by greater cell number and a well formed inner cell mass (ICM) (Dumoulin et al., Hum Reprod (1999) 14:465-469). In previous investigations, human parthenogenetic embryos were developed in vitro using gas mixtures with high (20%) oxygen content (Lin et al., Stem Cells (2003) 21:152-161; Cibelli et al., J Reg Med (2001) 2:25-31).

In one embodiment, methods for ICM isolation and phESC culturing included using human skin fibroblasts were, and cells were propagated with human umbilical cord blood serum (HUCBS) instead of animal serum and used them as feeder cells. Derivation and culture of phESC lines may be performed in VitroHES medium (Vitrolife) designed for hESC culture with the addition of HUCBS. For example, the use of HUCBS in production of hESCs had positive effects on ICM outgrowth and phESC propagation (e.g., the growth of phESC in VitroHES medium was better with the addition of HUCBS than in its absence). Further, the isolation ICMs from whole blastocysts by mechanical slicing from the trophectoderm outgrowth appeared to be a more gentle and preferable method versus immunosurgery and trypsin treatment. Moreover, this method permitted the exclusion of interaction with animal-derived reagents.

Although the phESC lines of the present invention present typical characteristics displayed by hESC lines, they show unique characteristics, including genotypes that are practically identical to those of the oocyte donors, as seen in the parthenogenetically-derived monkey ES cell line Cyno-1 (Vrana et al., 2003, Proc Natl Acad Sci USA (2003) 100: 11911-11916). As such, the creation of hESC lines from parthenogenetic embryos may be a superior way to generate MHC-matched and possibly histocompatible embryonic stem cells in comparison to SCNT.

As previous studies of mouse and monkey parthenogenetic stem cells have shown, these cells can form teratomas with derivatives from all three embryonic germ layers (Lin et al., 2003, supra; Vrana et al., supra). Monkey parthenogenetic embryonic stem cells under selective culture conditions have been differentiated into neural cells and functional dopaminergic and serotonergic neurons (Vrana et al., 2003, supra). phESC of the present invention can also be differentiated into derivatives of all three germ layers in vitro and in vivo and are pluripotent. Moreover, embryoid bodies from phESC were capable of giving rise to beating cardiomyocyte-like cells.

The present invention demonstrates a method of creating parthenogenetic human embryonic stem cells which experimental data shows that the phESC can be differentiated into functional cells that may be of great value in the treatment of human degenerative diseases.

In one embodiment, metaphase II oocytes are activated by incubating oocytes under various $O_2$ tension gas environments. In a related aspect, the low $O_2$ tension gas environment is created by a gas mixture comprising an $O_2$ concentration of about 2%, 3%, 4%, or 5%. In a further related aspect, the gas mixture comprises about 5% $CO_2$. Further, the gas mixture comprises about 90% $N_2$, 91% $N_2$, or 93% $N_2$. This gas mixture is to be distinguished from 5% $CO_2$ air, which is approximately about 5% $CO_2$, 20% $O_2$, and 75% $N_2$.

"O$_2$ tension" refers to the partial pressure (pressure exerted by a single component of a gas mixture) of oxygen in a fluid (i.e., liquid or gas). Low tension is when the partial pressure of oxygen (pO$_2$) is low and high tension is when the pO$_2$ is high.

"Defined-medium conditions" refer to environments for culturing cells where the concentration of components therein required for optimal growth are detailed. For example, depending on the use of the cells (e.g., therapeutic applications), removing cells from conditions that contain xenogenic proteins is important; i.e., the culture conditions are animal-free conditions or free of non-human animal proteins. In a related aspect, "in vitro fertilization (IVF) media" refers to a nutrient system which contains chemically defined substances on or in which fertilized oocytes can be grown.

"Extracellular matrix (ECM) substrates" refer to a surface beneath the cells which supports optimum growth. For example, such ECM substrates include, but are not limited to, Matrigel, laminin, gelatin, and fibronectin substrates. In a related aspect, such substrates may comprise collagen IV, entactin, heparin sulfate proteoglycan, to include various growth factors (e.g., bFGF, epidermal growth factor, insulin-like growth factor-1, platelet derived growth factor, nerve growth factor, and TGF-β-1).

"Embryo" refers to an embryo that results upon activation of a cell, e.g., oocyte or other embryonic cells containing DNA of all male or female origin, which optionally may be modified, that comprises a discernible trophectoderm and inner cell mass, which cannot give rise to a viable offspring and where the DNA is of all male or female origin. The inner cell mass or cells contained therein are useful for the production of pluripotent cells as defined previously.

"Inner cell mass (ICM)" refers to the inner portion of an embryo which gives rise to fetal tissues. Herein, these cells are used to provide a continuous source of pluripotent cells in vitro. Further, the ICM includes the inner portion of the embryo that results from androgenesis or gynogenesis, i.e., embryos that result upon activation of cells containing DNA of all male or female origin. Such DNA, for example, will be human DNA, e.g., human oocyte or spermatozoal DNA, which may or may not have been genetically modified.

"Trophectoderm" refers to another portion of early stage embryo which gives rise to placental tissues, including that tissue of an embryo that results from androgenesis or gynogenesis, i.e., embryos that result from activation of cells that contain DNA of all male or female origin, e.g., human ovarian or spermatozoan.

"Differentiated cell" refers to a non-embryonic cell that possesses a particular differentiated, i.e., non-embryonic, state. The three earliest differentiated cell types are endoderm, mesoderm, and ectoderm.

"Substantially identical" refers to a quality of sameness regarding a particular characteristic that is so close as to be essentially the same within the ability to measure difference (e.g., by HLA typing, SNP analysis, and the like).

"Histocompatible" refers to the extent to which an organism will tolerate a graft of a foreign tissue.

"Genomic imprinting" refers to the mechanism by which a number of genes throughout the genome are monoallelically expressed according to their parental origin.

"Homoplasmy," including grammatical variations thereof, refers to the presence of the same type of the mitochondrial DNA (mtDNA) within a cell or individual.

"Heteroplasmy," including grammatical variations thereof, refers to the presence of a mixture of more than one type of mitochondrial DNA (mtDNA) within a cell or individual.

"Uniparental" refers to one or more cells or individuals from which another arises and to which it remains subsidiary.

"Mechanically isolating" refers to the process of separating cell aggregates by physical forces. For example, such a process would exclude the use of enzymes (or other cell cleavage products) which might contain non-human materials.

In the native environment, immature oocytes (eggs) from the ovary undergo a process of maturation which results in the progression through meiosis to metaphase II of meiosis. The oocytes then arrest at metaphase II. In metaphase II, the DNA content of the cell consists of a haploid number of chromosomes, each represented by two chromatids.

Such oocytes may be maintained indefinitely by cryopreserving by, for example, but not limited to, microinjection with a sugar.

In one embodiment, a method for producing human stem cells from a cryopreserved oocyte or parthenote is provided, including microinjecting into the cytoplasm of the oocyte or parthenote a cryopreservation agent, freezing the oocyte or parthenote to a cryogenic temperature to cause it to enter a dormant state, storing the oocyte or parthenote in the dormant state, thawing the oocyte or parthenote, parthenogeneically activating the oocyte under high O$_2$ tension in the presence or an ionophore followed by contacting the oocyte with a serine-threonine kinase inhibitor under low O$_2$ tension, culturing the activated oocyte or parthenote until blastocyst formation, isolating an inner cell mass (ICM) from the blastocyst, and culturing the cells of the ICM on a layer of human feeder cells, where culturing the ICM cells is carried out under high O$_2$ tension.

In one aspect, oocytes obtained as described are transferred to modified, isotonic IVF covered with embryo-tested mineral oil (Sigma), or any other suitable medium. If desired, the oocytes may be incubated with an extracellular sugar at the same concentration as the amount planned for microinjection. For example, to inject 0.1 M sugar, oocytes may be equilibrated in DMEM/F-12 with 0.1 M sugar. In one aspect, the cryopreservation agent comprises a lower Na$^+$ concentration than standard DMEM (i.e., Na$^+$ low media). In a related aspect, the cryopreservation agent comprises a higher K$^+$ concentration than standard DMEM (i.e., K$^+$ high). In a further related aspect, the cryopreservation agent comprises both a lower Na$^+$ and higher K$^+$ concentration than standard DMEM (i.e., Na$^+$ low/K$^+$ high media). In one aspect, the cryopreservation agent comprises an organic buffer, including but not limited to, HEPES. In another aspect, the cryopreservation agent comprises moieties that inhibit apoptotic protein (e.g., capases).

Alternatively, the oocytes may be optionally equilibrated with any other substantially non-permeable solute, such a NaCl, to decrease their cell volume prior to microinjection. This initial decrease in cell volume may result in a smaller final volume of the microinjected oocytes compared to oocytes not incubated in a hypertonic media prior to microinjection. This smaller final volume may minimize any potential adverse effect from the swelling of the oocytes. This general procedure for the preparation of cells for microinjection may also be used for other cell types (e.g., activated oocytes, hES cells, and the like).

The oocytes are then microinjected with a cryopreservation agent. Microinjection equipment and procedures are well characterized in the art and microinjection equipment known for use in injecting small molecules into cells may be used with the invention. In an exemplary microinjection step, oocytes can be microinjected at a pressure of 10 psi for 30 milliseconds. Another example of a standard microinjection technique is the method described by Nakayama and Yanagimachi (Nature Biotech. 16:639-642, 1998).

A cryopreservation agent useful in this process includes any chemical that has cryo-protective properties and is ordinarily non-permeable. In particular, the cryopreservation agent can include sugars either alone or mixed together with other traditional cryopreservation agents. Carbohydrate sugars such as trehalose, sucrose, fructose, and raffinose, may be microinjected to concentrations less than or equal to about 1.0 M, and more preferably, less than or equal to about 0.4 M. In one aspect, the concentration is between 0.05 and 0.20 M, inclusive. Additionally, an extracellular sugar or traditional cryopreservation agent may be added prior to storage. If the cells were incubated in a hypertonic solution prior to microinjection, the substantially non-permeable solute may be allowed to remain in the media after microinjection or may be removed from the media by washing the cells with media containing a lower concentration, or none, of this solute.

Certain sugars or polysaccharides which ordinarily do not permeate cell membranes because they are too large to pass through the membrane have superior physiochemical and biological properties for cryopreservation purposes. While these sugars ordinarily do not permeate cell membranes on their own, using the method as described, these ordinarily non-permeating sugars may be microinjected intracellularly to result in a beneficial effect.

Non-permeating sugars having a stabilizing or preserving effect on cells that are especially useful as the cryopreservation agent in the present method include sucrose, trehalose, fructose, dextran, and raffinose. Among these sugars, trehalose, a non-reducing disaccharide of glucose, has been shown to be exceptionally effective in stabilizing cell structures at low concentrations. The addition of extracellular glycolipids or glycoproteins may also stabilize the cell membrane.

Following the microinjection of the cryopreservation agent, the cells are prepared for storage. A variety of methods for freezing and/or drying may be employed to prepare the cells for storage. In particular, three approaches are described herein: vacuum or air drying, freeze drying, and freeze-thaw protocols. Drying processes have the advantage that the stabilized biological material may be transported and stored at ambient temperatures.

Typically, oocytes loaded with 1 to 2M DMSO are cooled at a very slow cooling rate (0.3 to 0.5° C./min) to an intermediate temperature (−60° C. to −80° C.) before plunging in liquid nitrogen for storage. The sample can then be stored at this temperature.

The suspended material can then be stored at cryopreservation temperatures, for example, by leaving the vials in liquid nitrogen ($LN_2$), for the desired amount of time.

Protocols for vacuum or air drying and for freeze drying proteins are well characterized in the art (Franks et al., "Materials Science and the Production of Shelf-Stable Biologicals," BioPharm, October 1991, p. 39; Shalaev et al., "Changes in the Physical State of Model Mixtures during Freezing and Drying: Impact on Product Quality," Cryobiol. 33, 14-26 (1996)) and such protocols may be used to prepare cell suspensions for storage with the method as described. In addition to air drying, other convective drying methods that may be used to remove water from cell suspensions include the convective flow of nitrogen or other gases.

An exemplary evaporative vacuum drying protocol useful with the method of the invention may include placing 20 μl each into wells on 12 well plates and vacuum drying for 2 hours at ambient temperature. Of course, other drying methods could be used, including drying the cells in vials. Cells prepared in this manner may be stored dry, and rehydrated by diluting in DMEM or any other suitable media.

A method of the invention using freeze drying to prepare the cells for storage begins with freezing the cell suspension. While methods of freezing known in the art may be employed, the simple plunge freezing method described herein for the freeze-thaw method may also be used for the freezing step in the freeze drying protocol.

After freezing, a two stage drying process may be employed. In the first stage, energy of sublimation is added to vaporize frozen water. Secondary drying is performed after the pure crystalline ice in the sample has been sublimated. Freeze dried cells can be stored and hydrated in the same manner as described above for vacuum drying. Viable cells may then be recovered.

After the recovery of cells from a frozen or dried state, any external cryopreservation agent may be optionally removed from the culture media. For example, the media may be diluted by the addition of the corresponding media with a lower concentration of cryopreservation agent. For example, the recovered cells may be incubated for approximately five minutes in media containing a lower concentration of sugar than that used for cell storage. For this incubation, the media may contain the same sugar that was used as the cryopreservation agent; a different cryopreservation agent, such as galactose; or any other substantially non-permeable solute. To minimize any osmotic shock induced by the decrease in the osmolarity of the media, the concentration of the extracellular cryopreservation agent may be slowly decreased by performing this dilution step multiple times, each time with a lower concentration of cryopreservation agent. These dilution steps may be repeated until there is no extracellular cryopreservation agent present or until the concentration of cryopreservation agent or the osmolarity of the media is reduced to a desired level.

The parthenogenetically activated oocytes, blastocysts, ICM, autologous stem cells and differentiated cells derived from the same can be stored or "banked" in a manner that allows the cells to be revived as needed in the future. An aliquot of the parthenogenetically activated oocytes and autologous or allogenic stem cells can be removed at any time, to be grown into cultures of many undifferentiated cells and then differentiated into a particular cell type or tissue type, and may then be used to treat a disease or to replace malfunctioning tissues in a subject. In one aspect, the cells are parthenogenetically derived from the donor, the cells can be stored so that an individual or close relative can have access to cells for an extended period of time. In another aspect, the cells are parthenogenetically derived from a donor who is homozygous for a HLA-haplotype that is common in a human population, the cells can be stored so that an individual with the same or nearly the same HLA-haplotype can have access to cells for an extended period of time. In one aspect, the cells are parthenogenetically derived from a donor who has a HLA-haplotype that is common in a human population, and the cells can be stored so that an individual with the same or nearly the same HLA-haplotype can have access to cells for an extended period of time.

In one embodiment, a cell bank is provided for storing parthenogenetically activated oocytes, blastocysts, ICM, and/or autologous or allogenic stem cell samples and differentiated derivatives thereof. In another embodiment, methods for administering such a cell bank are provided. U.S. Published Patent Application No. 20030215942, which is incorporated by reference herein in its entirety, provides an example of a stem cell bank system.

Using methods such as those described above, the isolation and in vitro propagation of parthenogenetically activated oocytes, blastocysts, ICM, and autologous or allogenic stem cell samples and differentiated derivatives thereof and their cryopreservation facilitates the establishment of a "bank" of transplantable human stem cells. Because it is possible to store smaller aliquots of cells, the banking procedure could take up a relatively small space. Therefore, the cells of many individuals could be stored or "banked" on a short term or long term basis, with relatively little expense.

In one embodiment, a portion of the sample is made available for testing, either before or after processing and storage.

This invention also provides methods of recording or indexing the parthenogenetically activated oocyte, blastocyst, ICM, and/or autologous or allogenic stem cell samples and differentiated derivatives thereof so that when a sample needs to be located, it can be easily retrieved. Any indexing and retrieval system can be used to fulfill this purpose. Any suitable type of storage system can be used so that the parthenogenetically activated oocytes, blastocysts, ICM, and/or autologous allogenic stem cells and differentiated derivatives thereof can be stored. The samples can be designed to store individual samples, or can be designed to store hundreds, thousands, and even millions of different cell samples.

The stored parthenogenetically activated oocyte, blastocyst, ICM, and/or autologous or allogenic stem cell samples and differentiated derivatives thereof can be indexed for reliable and accurate retrieval. For example, each sample can be marked with alphanumeric codes, bar codes, or any other method or combinations thereof. There may also be an accessible and readable listing of information enabling identification of each parthenogenetically activated oocyte, blastocyst, ICM, and/or autologous allogenic stem cell sample and differentiated derivatives thereof and its location in the bank and enabling identification of the source and/or type the cell sample, which is outside of the bank. This indexing system can be managed in any way known in the art, e.g., manually or non-manually, e.g. a computer and conventional software can be used.

In one embodiment, the cell samples are organized using an indexing system so that the sample will be available for the donor's use whenever needed. In other embodiments, the cell samples can be utilized by individuals related to the original donor. In alternative embodiments, the cell samples can be utilized by individuals with HLA-haplotypes that match the HLA-haplotypes of the cell samples. Once recorded into the indexing system, the cell sample can be made available for matching purposes, e.g., a matching program will identify an individual with matching type information and the individual will have the option of being provided the matching sample.

The storage banking system can comprise a system for storing a plurality of records associated with a plurality of individuals and a plurality of cell samples. Each record may contain type information, genotypic information or phenotypic information associated with the cell samples or specific individuals. In one embodiment, the system will include a cross-match table that matches types of the samples with types of individuals who wish to receive a sample.

In one embodiment, the database system stores information for each parthenogenetically activated oocyte, blastocyst, ICM, and/or autologous or allogenic stem cell sample or differentiated derivatives thereof in the bank. Certain information is stored in association with each sample. The information may be associated with a particular donor, for example, an identification of the donor and the donor's medical history. For example, each sample may be HLA typed and the HLA type information may be stored in association with each sample. The information stored may also be availability information. The information stored with each sample is searchable and identifies the sample in such a way that it can be located and supplied to the client immediately.

Accordingly, embodiments of the invention utilize computer-based systems that contain information such as the donor, date of submission, type of cells submitted, types of cell surface markers present, HLA-type of the cells, genetic information relating to the donor, or other pertinent information, and storage details such as maintenance records and the location of the stored samples, and other useful information.

The term "a computer-based system" refers to the hardware, software, and any database used to store, search, and retrieve information about the stored cells. The computer-based system preferably includes the storage media described above, and a processor for accessing and manipulating the data. The hardware of the computer-based systems of this embodiment comprises a central processing unit (CPU) and a database. A skilled artisan can readily appreciate that any one of the currently available computer-based systems are suitable.

In one embodiment, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. Information relating to the parthenogenetically activated oocyte, blastocyst, ICM, and/or autologous stem cell can be stored in a well known manner in the main memory, any of the secondary storage devices, and/or a removable storage medium. Software for accessing and processing these data (such as search tools, compare tools, etc.) reside in main memory during execution.

As used herein, "a database" refers to memory that can store any useful information relating to the parthenogenetically activated oocyte collections and/or autologous or allogenic stem cell collections, including differentiated derivatives thereof, and the donors.

The data relating to the stored parthenogenetically activated oocyte, blastocyst, ICM, and/or autologous or allogenic stem cells and differentiated derivatives thereof, can be stored and manipulated in a variety of data processor programs in a variety of formats. For example, the data can be stored as text in a word processing file, such as Microsoft WORD or WORDPERFECT, an ASCII file, an html file, or a pdf file in a variety of database programs familiar to those of skill in the art, such as DB2, SYBASE, or ORACLE.

A "search program" refers to one or more programs that are implemented on the computer-based system to search for details or compare information relating to the cryopreserved samples within a database. A "retrieval program" refers to one or more programs that can be implemented on the computer-based system to identify parameters of interest in the database. For example, a retrieval program can be used to find samples that fit a particular profile, samples having specific markers or DNA sequences, or to find the location of samples corresponding to particular individuals.

There is no upper limit on the number of cell samples that can be stored in one cell bank. In one embodiment, hundreds of products from different individuals will be stored at one bank or storage facility. In another embodiment, up to millions of products may be stored in one storage facility. A single storage facility may be used to store parthenogenetically activated oocyte and/or autologous stem cell samples, or multiple storage facilities may be used.

In some embodiments of the present invention, the storage facility may have a means for any method of organizing and indexing the stored cell samples, such as, for example, automated robotic retrieval mechanisms and cell sample manipulation mechanisms. The facility may include micro-manipulation devices for processing cell samples. Known conventional technologies can be used for efficient storage and retrieval of the cell samples. Exemplary technologies include but are not limited to Machine Vision, Robotics, Automated Guided Vehicle System, Automated Storage and Retrieval Systems, Computer Integrated Manufacturing, Computer Aided Process Planning, Statistical Process Control, and the like.

The type information or other information associated with the individual in need of a sample may be recorded into a system that can be used to identify an appropriate matching product, such as, for example, a database system, an indexing system, and the like. Once recorded in the system, a match can be made between the type of the individual and a donor cell sample. In preferred embodiments, the donor sample is from the same individual as the individual in need of the sample. However, similar but not identical donor/recipient matches can also be used. The matching sample is available for the individual possessing the matching type identifier. In one embodiment of this invention, the individual's identification information is stored in connection with the cell sample. In some embodiments, the matching process occurs around the time of harvesting the sample, or can occur at any time during processing, storage, or when a need arises. Accordingly, in some embodiments of the invention, the matching process occurs before the individual is in actual need of the cell sample.

When the parthenogenetically activated oocyte, blastocyst, ICM, and/or autologous or stem cell samples, including differentiated derivatives thereof, are needed by an individual, they may be retrieved and made available for research, transplantation or other purposes within minutes, if desired. The sample may also be further processed to prepare it for transplantation or other needs.

Normally, oocytes in arrest at metaphase II are ovulated and fertilized by the sperm. The sperm initiates the completion of meiosis in a process called activation. During activation, the pairs of chromatids separate, the second polar body is extruded, and the oocyte retains a haploid number of chromosomes, each with one chromatid. The sperm contributes the other haploid complement of chromosomes to make a full diploid cell with single chromatids. The chromosomes then progress through DNA synthesis during the first cell cycle. These cells then develop into embryos.

By contrast, embryos described herein are developed by artificial activation of cells, typically mammalian oocytes or blastomeres containing DNA of all male or female origin. As discussed in the background of the invention, many methods have been reported in the literature for artificial activation of unfertilized oocytes. Such methods include physical methods, e.g., mechanical methods such as pricking, manipulation or oocytes in culture, thermal methods such as cooling and heating, repeated electric pulses, enzymatic treatments, such as trypsin, pronase, hyaluronidase, osmotic treatments, ionic treatments such as with divalent cations and calcium ionophores, such as ionomycin and A23187, the use of anesthetics such as ether, ethanol, tetracaine, lignocaine, procaine, phenothiazine, tranquilizers such as thioridazine, trifluoperazine, fluphenazine, chlorpromazine, the use of protein synthesis inhibitors such as cycloheximide, puromycin, the use of phosphorylation inhibitors, e.g., protein kinase inhibitors such as staurosporine, 2-aminopurine, sphingosine, and DMAP, combinations thereof, as well as other methods.

Such activation methods are well known in the art and are discussed, for example, in U.S. Pat. No. 5,945,577.

In one embodiment, a human cell in metaphase II, typically an oocyte or blastomere comprising DNA of all male or female origin, is artificially activated for effecting artificial activation of oocytes.

In a related aspect, the activated cell, e.g., oocyte, which is diploid, is allowed to develop into an embryo that comprises a trophectoderm and an inner cell mass. This can be effected using known methods and culture media that facilitate blastocyst development.

After the gynogenetic embryos have been cultured to produce a discernable trophectoderm and inner cell mass, the cells of the inner cell mass are then used to produce the desired pluripotent cell lines. This can be accomplished by transferring cells derived from the inner cell mass or the entire inner cell mass onto a culture that inhibits differentiation. This can be effected by transferring the inner cell mass cells onto a feeder layer that inhibits differentiation, e.g., fibroblasts or epithelial cells, such as fibroblasts derived from postnatal human tissues, etc., or other cells that produce LIF. Other factors/components may be employed to provide appropriate culture conditions for maintaining cells in the undifferentiated state including, but not limited to, addition of conditioned media (Amit et al., Developmental Biol (2000) 227:271-278), bFGF and TGF-β1 (with or without LIF) (Amit et al., Biol Reprod (2004) 70:837-845), factors which activate the gp130/STAT3 pathway (Hoffman and Carpenter, Nature Biotech (2005) 23(6):699-708), factors which activate the PI3K/Akt, PKB pathway (Kim et al., FEBS Lett (2005) 579:534-540), factors that are members of the bone morphogenetic protein (BMP) super family (Hoffman and Carpenter (2005), supra), and factors which activate the canonical/β-catenin Wnt signaling pathway (e.g., GSK-3-specific inhibitor; Sato et al., Nat Med (2004) 10:55-63). In a related aspect, such factors may comprise culture conditions that include feeder cells and/or ECM substrates (Hoffman and Carpenter (2005), supra).

In one aspect, the inner cell mass cells are cultured on human postnatal foreskin or dermal fibroblast cells or other cells which produce leukemia inhibitory factor, or in the presence of leukemia inhibitory factor. In a related aspect, feeder cells are inactivated prior to seeding with the ICM. For example, the feeder cells can be mitotically inactivated using an antibiotic. In a related aspect, the antibiotic can be, but is not limited to, mitomycin C. In a related aspect, the feeder cells may be inactivated using radiation.

Culturing will be effected under conditions that maintain the cells in an undifferentiated, pluripotent state, for prolonged periods, theoretically indefinitely. In one embodiment, oocytes are parthenogeneically activated with calcium ionophores under high $O_2$ tension followed by contacting the oocytes with a serine-threonine kinase inhibitor under low $O_2$ tension. The resulting ICM from the parthenogenically activated oocytes is cultured under high $O_2$ tension, where the cells, for example, are maintained using a gas mixture comprising 20% $O_2$. In one aspect, culturable refers to being capable of, or fit for, being cultivated. In a related aspect, ICM isolation is carried out mechanically after four days of blastocyst cultivation, where the cultivation is carried out on feeder cells. Such cultivation, for example, eliminates the need to use materials derived from animal sources, as would be the case for immunosurgery.

In a related aspect, culture media for the ICM is supplemented with non-animal sera, including but not limited to, human umbilical cord serum, where the serum is present in defined media (e.g., IVF, available from MediCult A/S, Denmark; Vitrolife, Sweden; or Zander IVF, Inc., Vero Beach, Fla.). In another aspect, the media and processes as provided are free of animal products. In a related aspect, animal products are those products, including serum, interferons, chemokines, cytokines, hormones, and growth factors, that are from non-human sources.

The pluripotent state of the cells produced by the present invention can be confirmed by various methods. For example, the cells can be tested for the presence or absence of characteristic ES cell markers. In the case of human ES cells, examples of such markers are identified supra, and include SSEA-4, SSEA-3, TRA-1-60, TRA-1-81 and OCT 4, and are known in the art.

Also, pluripotency can be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types. Methods for producing chimeric animals are well known in the art and are described in U.S. Pat. No. 6,642,433.

Yet another method of confirming pluripotency is to observe ES cell differentiation into embryoid bodies and other differentiated cell types when cultured under conditions that favor differentiation (e.g., removal of fibroblast feeder layers). This method has been utilized and it has been confirmed that the subject pluripotent cells give rise to embryoid bodies and different differentiated cell types in tissue culture.

The resultant pluripotent cells and cell lines, preferably human pluripotent cells and cell lines, which are derived from DNA of entirely female original, have numerous therapeutic and diagnostic applications. Such pluripotent cells may be used for cell transplantation therapies or gene therapy (if genetically modified) in the treatment of numerous disease conditions.

In this regard, it is known that mouse embryonic stem (ES) cells are capable of differentiating into almost any cell type. Therefore, human pluripotent (ES) cells produced according to the invention should possess similar differentiation capacity. The pluripotent cells according to the invention will be induced to differentiate to obtain the desired cell types according to known methods. For example, human ES cells produced according to the invention may be induced to differentiate into hematopoietic stem cells, muscle cells, cardiac muscle cells, liver cells, islet cells, retinal cells, cartilage cells, epithelial cells, urinary tract cells, etc., by culturing such cells in differentiation medium and under conditions which provide for cell differentiation. Medium and methods which result in the differentiation of ES cells are known in the art as are suitable culturing conditions.

For example, Palacios et al, Proc. Natl. Acad. Sci., USA, 92:7530-7537 (1995) teach the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferal of cell aggregates to a substrate which provides for cell attachment.

Moreover, Pedersen, J. Reprod. Fertil. Dev., 6:543-552 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al, Dev. Biol., 168:342-357 (1995) teach in vitro differentiation of embryonic stem cells to produce neural cells which possess neuronal properties. These references are exemplary of reported methods for obtaining differentiated cells from embryonic or stem cells. Thus, using known methods and culture medium, one skilled in the art may culture the subject ES cells, including genetically engineered or transgenic ES cells, to obtain desired differentiated cell types, e.g., neural cells, muscle cells, hematopoietic cells, etc. Pluripotent cells produced by the methods described herein may be used to obtain any desired differentiated cell type.

For example, the hpSC-Hhom line's major histocompatibility complex (MHC) homozygosity may be uniquely suitable for therapeutic applications. With proper selection of oocyte donors according to their HLA haplotype and the HLA-haplotype of the donor's biologic parents, and with FDA approved manufacturing protocols, it is possible to generate a bank of cell lines, whose tissue derivatives collectively could be MHC-matched with a significant number of individuals. It has been suggested that a panel of only ten HLA homozygous human embryonic stem cell lines selected for common types can provide a complete HLA-A, HLA-B and HLA-DR match for 37.7% of United Kingdom recipients, and a beneficial match for 67.4%. (Taylor C. J. et al., Lancet (2005) 366(9502):2019-2025). Using the U.S. population calculations suggest that there are close to 200 common haplotypes per racial group (Mori M. et al., Transplantation (1997) 64:1017-1027). The hpSC-Hhom-4 line carries the most common haplotype, potentially providing an MHC match for nearly 5% of individuals within this population. Thus, the hpSC-Hhom lines are ideally suited for establishing a repository of differentiated cells and tissues HLA-matched to the population, which could be available for immediate clinical application. Possible concerns are hematopoietic derivatives which may potentially invoke Graft Versus Host Disease (Billingham, R E., Harv Led (1966) 62:21-78) in a heterozygous recipient, in which case patient-specific parthenogenetic stem cells may provide a solution.

Therapeutic usages of differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by incorporating male or female DNA derived from a male or female cancer or AIDS patient with an enucleated oocyte, obtaining pluripotent cells as described above, and culturing such cells under conditions which favor differentiation, until hematopoietic stem cells are obtained. Such hematopoietic cells may be used in the treatment of diseases including cancer and AIDS.

Alternatively, the subject pluripotent cells may be used to treat a patient with a neurological disorder by culturing such cells under differentiation conditions that produce neural cell lines. Specific diseases treatable by transplantation of such human neural cells include, by way of example, Parkinson's disease, Alzheimer's disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms. In a related aspect, nerve precursors can be used to reanneal severed/damaged nerve fibers to restore movement after hand, leg, and spinal cord injuries.

One object of the subject invention is that it provides an essentially limitless supply of pluripotent, human cells that can be used to produce differentiated cells suitable for autologous transplantation for the oocyte donor or allogenic transplantation for HLA-matched recipients. Human embryonic stem cells and their differentiated progeny derived from blastocysts remaining after infertility treatments, or created using NT, will likely be rejected by a recipient's immune system when used in allogenic cell transplantation therapy. Parthenogeneically derived stem cells should result in differentiated cells that could alleviate the significant problem associated with current transplantation methods, i.e., rejection of the transplanted tissue which may occur because of host-vs-graft or graft-vs-host rejection relative to the oocyte donor. Conventionally, rejection is prevented or reduced by the administration of anti-rejection drugs such as cyclosporin. However, such drugs have significant adverse side-effects, e.g., immunosuppression, carcinogenic properties, as well as being very expensive. Cells produced by the methods as disclosed should eliminate, in some cases, and at least greatly reduce, in others, the need for anti-rejection drugs relative to the oocyte donor.

Another object of the subject invention is that it provides an essentially limitless supply of pluripotent, human cells that can be used to produce differentiated cells suitable for allogenic transplantation to members of the oocyte donor's family (e.g., siblings). The cells will be immunologically and genetically similar to those of the oocytes donor's direct family members and thus less likely to be rejected by the donor's family members.

Another object of this method is that parthenogeneic activation of mammalian oocytes is a relatively simple procedure when compared to SCNT and results in the creation of stem cells with less cell manipulation.

Parthenogeneic activation of mammalian oocytes has shown to be more efficient in the creation of stem cells than methods requiring mechanical manipulation of the oocyte (e.g., SCNT).

One drawback of SCNT is that subjects with deficient mitochondrial respiratory chain activity present phenotypes with striking similarities to abnormalities commonly encountered in SCNT fetuses and offspring (Hiendleder et al, Repro Fertil Dev (2005) 17(1-2):69-83). Cells normally contain only one type of mitochondrial DNA (mtDNA), termed homoplasmy, however, heteroplasmy does exist, usually as a combination of mutant and wild-type mt DNA molecules or form a combination of wild-type variants (Spikings et al., Hum Repro Update (2006) 12(4):401-415). As heteroplasmy can result in mitochondrial disease, various mechanisms exist to ensure maternal-only transmission. However, with the increasing use of protocols which bypass normal mechanisms for homoplasmy maintenance (e.g., cytoplasmic transfer (CT) and SCNT), perturbed mitochondrial function may be intrinsic to stem cells derived from these sources.

In one aspect, as the parthenotes are uniparental, the possibility of heteroplasmy is minimized.

Other diseases and conditions treatable by cell therapy include, by way of example, spinal cord injuries, multiple sclerosis, muscular dystrophy, diabetes, liver diseases Including acute diseases (viral hepatitis, drug overdoses (acetaminophen) and others), chronic diseases (chronic hepatitis and others (generally leading to cirrhosis)), heritable liver defects (hemophilia B, factor IX deficiency, bulirubin metabolism defects, urea cycle defects, lysosomal storage disease, al-antitrypsin deficiency and others), heart diseases, cartilage replacement, burns, foot ulcers, gastrointestinal diseases, vascular diseases, kidney disease, retinal disease, urinary tract disease, and aging related diseases and conditions.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc.

For example, the gene encoding brain derived growth factor may be introduced into human pluripotent cells produced according to the invention, the cells differentiated into neural cells and the cells transplanted into a Parkinson's patient to retard the loss of neural cells during such disease.

Also, the subject pluripotent human ES cells, may be used as an in vitro model of differentiation, in particular for the study of genes which are involved in clinical and biological research. Such research includes, but is not limited to, the regulation of early development, regenerative medicine or drug development. For example, the insertion of reporter genes (e.g., green fluorescent protein (gfp), luciferase and the like) that are transcribed along with genes of interest may be used to study disease, developmental biology, regenerative medicine, or drug development. Also, differentiated cell tissues and organs produced using the subject ES cells may be used in drug studies.

Further, the subject ES cells or differentiated cells derived therefrom may be used as nuclear donors for the production of other ES cells and cell colonies.

Still further, pluripotent cells obtained according to the present disclosure may be used to identify proteins and genes that are involved in embryogenesis. This can be effected, e.g., by differential expression, i.e., by comparing mRNAs that are expressed in pluripotent cells provided according to the invention to mRNAs that are expressed as these cells differentiate into different cell types, e.g., neural cells, myocardiocytes, other muscle cells, skin cells, etc. Thereby, it may be possible to determine what genes are involved in differentiation of specific cell types.

Further, ES cells and/or their differentiated progeny that have specific genetic defects, such as the genetic defect that leads to Duchene's Muscular Dystrophy, may be used as models to study the specific disease associated with the genetic defect.

Also, it is another object of the present disclosure to expose pluripotent cell lines produced according to the described methods to cocktails of different growth factors, at different concentrations and under different cell culture conditions such as cultured on different cell matrices or under different partial pressures of gases so as to identify conditions that induce the production and proliferation of desired differentiated cell types.

The following examples are intended to illustrate but not limit the invention.

EXAMPLES

Production of Human Parthenogeneic Embryogenic Stem Cells

Materials and Methods

Donor Selection and Informed Consent Process

Donors were recruited from a pool of women who first presented to the center for IVF and were found to be eligible for an IVF procedure according to clinical guidelines.

Each potential donor was approached by her doctor and informed and counseled about the study. If the donor chose to participate, the donor was presented with a comprehensive informed consent document (reviewed and approved by an independent US-based ESCRO Committee), written in the Russian language, which outlined the purpose of the study and the procedures. If the potential donor had questions, a medical doctor was made available. Only potential donors who signed the informed consent participated in the study.

Donors voluntarily donated with no financial compensation for oocytes. The signed informed consent stated that all donated material was to be used for research and not for reproductive purposes, namely, the development of methods to derive human ES cells and their differentiated progeny.

Research eligibility was determined according to the FDA's Eligibility Determination for Donors of Human Cells, Tissues, and Cellular and Tissue-Based Products (FDA HCT/Ps, 2004), as well as Order No. 67 (Feb. 26, 2003) of the Russian Public Health Ministry. This included a thorough medical examination with chest X-ray, blood (including liver function tests), and urine analysis. Screening was also performed for *Chlamydia trachomatis, Neisseria gonorrhoeae*, syphilis, HIV, HBV and HCV.

Potential donors and parents were screened further for research participation according to HLA type.

In this protocol, the priority for oocyte harvest was a successful IVF procedure. The best fully developed mature cumulus oocyte complexes were selected for IVF. If the total number of oocytes harvested was less than 11, the woman was automatically excluded from donating for research purposes.

Donor Superovulation

Each donor underwent ovarian stimulation utilizing FSH (Gonal-F, Lab. Serono, Switzerland) from the 3rd to the 13th day of the menstrual cycle. A total of 1500 IU was given. From the 10th to the 14th day of the donor's menstrual cycle, gonadoliberin antagonist Orgalutran (Organon, Holland) was injected at 0.25 mg/day. From the 12th to the 14th day of the donor's menstrual cycle, a daily injection of 75 IU FSH+75 IU LH (Menopur, Ferring GmbH, Germany) was given. If an ultrasound examination displayed follicles between 18 and 20 mm in diameter, a single 8000 IU dose of hCG (Choragon, Ferring GmbH, Germany) was administered on the 14th day of the donor's menstrual cycle.

Transvaginal punction was performed 35 hours after hCG injection on approximately the 16th day. Follicular fluid was collected from the antral follicles of anesthetized donors by ultrasound-guided needle aspiration into sterile test tubes.

Oocyte Activation and Culture Ofparthenogenetic Embryos

Cumulus oocyte complexes (COCs) were picked from the follicular fluid, washed in Flushing Medium (MediCult) and then incubated in Universal IVF medium (MediCult) with Liquid Paraffin (MediCult) overlay for two hours in a 20% $O_2$, 5% $CO_2$, 37° C. humidified atmosphere. Before activation, COCs were treated with SynVitro Hyadase (MediCult) to remove cumulus cells, followed by incubation in Universal IVF medium with Paraffin overlay for 30 minutes. Further culture of oocytes and embryos was performed in a humidified atmosphere at 37° C. with an $O_2$-reduced gas mixture (90% $N_2$+5% $O_2$+5% $CO_2$) with the exception of the A23187 treatment, which was performed at conditions described for culture of COCs. Activation was performed in Universal IVF medium with Paraffin overlay by consecutive exposure of oocytes to 5 µM A23187 (Sigma) for five minutes and 10 µg/ml puromycin (Sigma) or 1mM 6-DMAP (Sigma) for four hours, followed by careful washing of oocytes in Universal IVF medium. Oocytes were then placed in fresh IVF medium with Paraffin overlay following culture. The next day (Day 1), parthenogenetically-activated oocytes were cultivated to the blastocyst stage using sequential BlastAssist System media (MediCult) according to the manufacturer's recommendations. From the derived blastocysts, the inner cell mass (ICM) was isolated on days five through six of culture.

Isolation of Blastocyst Inner Cell Mass and Culture of hpSC-Hhom

The zona pellucida was removed by 0.5% pronase (Sigma) treatment. Whole blastocysts were placed on a feeder layer of mitomycin C mitotically inactivated human neonatal skin fibroblasts (NSF) (Revazova et al, 2007, supra), in medium designed for the culture of hpSC-Hhom. When trophoblast cells spread following blastocyst attachment, the ICM became visible. After three to four days of additional culture, the ICM was isolated by mechanical slicing of the ICM from the trophectoderm outgrowth using a finely drawn glass pipette. The isolated ICM was plated on a fresh feeder layer and cultured for an additional three to four days. The first colony was mechanically cut and replated after five days of culture. All subsequent passages were made after five to six days of culture. Early passage colonies were mechanically divided into clumps and replated. Further passing of hpSC-Hhom was performed with collagenase IV treatment and mechanical dissociation. The propagation of hpSC-Hhom was performed at 37° C., 5% $CO_2$ in a humidified atmosphere.

For the culture of ICM and hpSC-Hhom we used Vitro-HES (Vitrolife) supplemented with 4 ng/ml hrbFGF (Chemicon), 5 ng/ml hrLIF (Chemicon) and 10% human umbilical cord blood serum. The medium for the culture of NSF consisted of 90% DMEM (high glucose, with L-glutamine) (Invitrogen), 10% human umbilical cord blood serum and penicillin-streptomycin (100 U/100 µg) (Invitrogen). Before medium preparation, human umbilical cord blood serum was screened for syphilis, HIV, HBV and HCV.

Characterization of hpSC-Hhom

For immunostaining of embryonic stem cell markers, hpSC-Hhom colonies were fixed at room temperature for 20 minutes with 4% paraformaldehyde to identify SSEA-1, SSEA-3 and SSEA-4; 100% methanol was used for five minutes at minus 20° C. to identify the remaining markers.

Monoclonal antibodies used included: SSEA-1 (MAB4301), SSEA-3 (MAB4303), SSEA-4 (MAB4304), TRA-1-60 (MAB4360) and TRA-1-81 (MAB4381) from Chemicon, as well as OCT-4 (sc-9081) from Santa Cruz Biotechnology, Secondary antibodies included Alexa Fluor 546 (orange-fluorescent) and 488 (green-fluorescent) from Molecular Probes (Invitrogen). Nuclei were stained with DAPI (Sigma). Alkaline phosphatase and telomerase activity were detected with AP kit and TRAPEZE Kit (Chemicon). Chromosomal slides were prepared by the routing method. G-banding was performed according to trypsin-Giemsa technique, and 30-100 metaphases were karyotyped in each instance.

Embryoid Body Formation and Neural Differentiation

The hpSC-Hhom colonies were mechanically divided into clumps and placed in 24-well cluster plates pre-coated with 2% agarose (Sigma) in medium containing 85% Knockout DMEM, 15% human umbilical cord blood serum, 1×MEM NEAA, 1 mM Glutamax, 0.055 mM P-mercaptoethanol, penicillin-streptomycin (50 U/50 μg) (all from Invitrogen, except the serum). Embryoid bodies were cultured in suspension for 14 days, followed by either plating for outgrowth development or additional culturing in suspension for one week.

Neural differentiation was induced by the cultivation of two week old embryoid bodies attached to a culture dish surface over the period of a week in differentiation medium DMEM/F12, B27, 2 mM Glutamax, penicillin-streptomycin (100 U/100 μg) and 20 ng/ml hrbFGF (all from Invitrogen). Some embryoid bodies gave rise to differentiated cells with neural morphology, others were dissected and additionally cultured to produce neurospheres.

Beating embryoid bodies appeared spontaneously following five days of culture after plating on an adhesive surface in the same medium as was used for embryoid body generation.

Immunocytochemistry of hpSC-Hhom Differentiated Derivatives

Embryoid bodies, neurospheres or contractile embryoid bodies were placed on poly-D-lysine (Sigma) treated micro cover glasses (VWR Scientific Inc.) and cultured for approximately one week in the appropriate differentiation medium. For immunostaining, differentiated cells were fixed with 100% methanol for five minutes at minus 20° C.

For the detection of ectodermal markers, we used monoclonal mouse anti-neurofilament 68 antibody (Sigma), anti-human CD56 (NCAM) antibody (Chemicon) and anti-beta III tubulin antibody (Chemicon) to highlight neuronal markers. Anti-glial fibrillary acidic protein (GFAP) antibody (Chemicon) was used to detect the glial cell marker.

For the detection of the mesodermal markers in three Week old embryoid bodies or in contractile embryoid bodies, monoclonal mouse anti-desmin antibody (Chemicon), anti-human alpha actinin antibody (Chemicon) was used as the muscle specific markers, and anti-human CD31/PE-CAM-1 antibody (R&D Systems), anti-human VE-Cadherin (CD 144) antibody (R&D Systems) was used as the endothelial markers.

For the detection of the endodermal markers in embryoid bodies, monoclonal mouse anti-human alpha-fetoprotein antibody (R&D Systems) was used. Secondary antibodies Alexa Fluor 546 (orange-fluorescent) and 488 (green-fluorescent) were from Molecular Probes (Invitrogen). Nuclei were stained with DAPI (Sigma).HLA genotyping Investigation of HLA haplotypes and HLA genotyping was performed for both donors and their parents. Genomic DNA was extracted from blood, cumulus cells, hpSC-Hhom and NSF with Dynabeads DNA Direct Blood from Dynal (Invitrogen). HLA genotyping was performed by PCR with allele-specific sequencing primers (PCR-SSP, Protrans). All tests were performed according to manufacturer's recommendations.

Asymetrix SNP Microarray Analysis

Genomic DNA was isolated from blood, cumulus cells, hpSC-Hhom and NSF by the phenol/chloroform extraction method. DNA samples obtained from three donors, four hpSC-Hhom lines and NSF were all genotyped with Affymetrix Mapping 250K Nsp Arrays. Since the initial data set containing 252,973 binary SNP markers exceeded the number necessary to determine equivalency of genomic samples, it was reduced to simplify computation.

The following criteria were used to select markers based on genetic considerations: 1) The greater the degree of heterozygosity in markers, the more information they provide in identifying the origins of the SNP samples. The heterozygosity of binary SNP markers is capped at a maximum of 0.5. Only SNP markers with heterozygosity greater than 0.375 were chosen (i.e. no allele has a frequency less than 0.25 or greater than 0.75 in the Caucasian population.); 2) All 22 autosomal chromosomes were used; 3) Markers with low reliability were removed, as the identification of samples for common origins is highly sensitive to genotyping errors. In the Affymetrix dataset, high confidence scores correspond to low reliability, so those markers with high confidence scores were removed. At the default setting, no call is made for a marker if its confidence score exceeds 0.25. Even more stringent requirements were applied for reliability by choosing only those markers that have confidence scores less than or equal to 0.02 for all 12 samples.

Applying these criteria, the number of SNP markers was reduced from 252,973 to 4,444. One final step was taken to reduce the number of markers (no random sampling was performed), by selecting only those where the intermarker distances were at least 0.1 cM (1 Mbp=1 cM), since markers very close to each other provide less information due to the presence of tight linkage between them. These steps led to the final selection of 3,993 markers.

The 3,993 markers thus chosen were analyzed with Relcheck (version 0.67, copyright (C) 2000 Karl W. Broman, Johns Hopkins University, Licensed under the GNU General Public License version 2 (June, 1991)). Relcheck provides a method for determining the relationship between a pair of SNP samples. This is based on calculating a likelihood ratio for observing a given configuration of markers according to the genetic relationship between samples. The use of Relcheck is based on the knowledge that since monozygotic twins share the same DNA, the test of equivalency between two samples can be made by checking if those samples may have come from monozygotic twins. Relcheck was run, with the assumption that genotyping error rates are approximately 0.4%. The Relcheck program identifies five types of relationships: monozygotic twins, parent/offspring pair, full siblings (full sibs), half siblings (half sibs) and unrelated (Boehnke M. et al., Am J Hum Genet (1997) 61:423-429; Broman K. W. et al., Am J Hum Genet (1998) 63:1563-1563).

In order to determine proportion of heterozygous SNPs across 15 chromosomes for donor and stem cell samples, 1495 randomly sampled SNP markers used for the earlier analysis were analysed for 6 stem cell lines, 4 donors, and 1 control sample.

The location of the centromere for each chromosome was determined by taking the middle point between the last available p marker (short arm) and the first available q marker (long arm) for each of the chromosomes 1-12. For acrocentric chromosomes 13-15, there was no SNP markers on the p arm, so the centromere was assumed to be at position 0 (start of the q arm).

The following values were used as the position of centromeres for chr 1-15 (in Mbp from end of p arm):

| Chrom. # | Mbp |
|---|---|
| chr1 = | 131.5051 |
| chr2 = | 92.7926 |
| chr3 = | 93.1514 |
| chr4 = | 51.0889 |
| chr5 = | 46.8726 |
| chr6 = | 60.5099 |
| chr7 = | 57.8019 |
| chr8 = | 45.3089 |
| chr9 = | 54.6881 |
| chr10 = | 39.0399 |
| chr11 = | 52.7549 |
| chr12 = | 35.6473 |
| chr13 = | 0 |
| chr14 = | 0 |
| chr15 = | 0 |

For each SNP marker, the absolute distance from the centromere on the specific chromosome was calculated (i.e., both directions from a centromere were treated equivalently, with "negative" distances all converted to positive distances). For the purpose of calculating the proportion of heterozygotes, chromosome distances (from the centromeres) were divided into 15 intervals (called "bins" in the output). Each interval was 10 Mbps in length. The number assigned to each "bin" corresponds to the upper bound on the chromosome distance for that interval. All units are expressed in mega base pairs (Mbp). For example:

Bins=10 corresponds to the interval [0,10] Mbp from the centomeres.
Bins=70 corresponds to the interval [60,70] Mbp from centromeres.
Bins=150 corresponds to the interval [140,150] Mbp from centromeres.

The base pair distances supplied in the original Affiymetrix SNP dataset were used to maintain consistency with the previous data analysis. For each interval, the proportion of heterozygosity was estimated by taking the mean value of the indicator variables for heterozygosity for all SNPs within that interval.

For donor and stem cells, the heterozygosity variable stores the mean value of the heterozygosity indicator variables at each SNP marker location for donor (2,12,10,11) and stem cell samples (3,4,5, 9,6,7,8). Corresponding values for homozygosity proportions can easily be obtained by subtracting the heterozygote values from 1.

Internal controls correctly identified the paired genotype relationship between split cultures derived from the same hpSC-Hhom line as "monozygous twins."

Analysis of Imprinted Genes

Total RNA was extracted as described (Chomcznski and Sacchi, Anal Biochem (1987) 162:156-159) and precipitated with isopropanol. Residual genomic DNA was removed using an RNAse free DNAse treatment (Promega). cDNA was synthesized from 1 µg total RNA using RevertAid M-MuLV reverse transcriptase (Fermentas) in 20 µl of the reaction volume. The PCR reactions were perforated with 1 µl cDNA, using Taq DNA polymerase (Fermentas). All reactions were performed according to the manufacturer's instructions.

The sequence of the primers and PCR conditions were as follows: TSSC5 (Lee et al., Cancer Res (1998) 58:4155-4159) forward primer 5'-GCTCTTCATGGTCATGT-TCTCCA-3' (SEQ ID NO:1) and reverse primer 5'-GGAGCAGTGGTTGTACAGAGG-3' (SEQ ID NO:2), at conditions of 94° C. for 4 min for 1 cycle; 94° C. for 1 min, 55° C. for 1 min, and 72° C. for 1 min for 33 cycles. The product size was 364 bp. H19 (Hashimoto et al., Nat Genet (1995) 9:109-110) forward primer 5'-TACAAC-CACTGCACTACCTG-3'(SEQ ID NO:3) and reverse primer 5'-TGGCCATGAAGATGGAGTCG-3'(SEQ ID NO:4), at conditions of 94° C. for 4 min for 1 cycle; 94° C. for 1 min, 52° C. for 1 min, and 72° C. for 1 min for 38 cycles. The product size was 148 bp. PEG1_1 (Li et al., J Biol Chem (2002) 277:13518-13527) forward primer 5'-GAG TCC TGT AGG CAA GGT CTT ACC T-3' (SEQ ID NO:5) and reverse primer 5'-CTT GCC TGA AGA CTT CCA TGA GTG A-3'(SEQ ID NO:6), at conditions of 94° C. for 4 min for 1 cycle; 94° C. for 1 min, 55° C. for 1 min, and 72° C. for 1 min for 35 cycles. The product size was 155 bp. PEG1_2 (Li et al., 2002, supra) forward primer 5'-GCT GCT GGC CAG CTC TGC ACG GCT G-3' (SEQ ID NO:7) and reverse primer 5'-CTT GCC TGA AGA CTT CCA TGA GTG A-3'(SEQ ID NO:8), at conditions of 94° C. for 4 min for 1 cycle; 94° C. for 1 min, 65° C. for 1 min, and 72° C. for 1 min for 39 cycles. The product size was 230 bp. SNRPN (Glenn et al., Hum Mol Genet (1993) 2:2001-2005) forward primer 5'-CTTAGCTGAGACACCAAGAGG-3' (SEQ ID NO:9) and reverse primer 5'-GCAGCATCTTGC-TACTCTTGC-3'(SEQ ID NO:10), at conditions of 94° C. for 4 min for 1 cycle; 94° C. for 1 min, 55° C. for 1 min, and 72° C. for 1 min for 33 cycles. The product size was 246 bp. GAPDH (Adjaye et al., Gene (1999) 237:373-383) forward primer 5'-ACCACAGTCCATGCCATCAC-3' (SEQ ID NO: 11) and reverse primer 5'-TCCACCACCCTGTTGCTGTA-3'(SEQ ID NO: 12), at conditions of 94° C. for 4 min for 1 cycle; 94° C. for 1 min, 55° C. for 1 min, and 72° C. for 1 min for 21 cycles. The product size was 450 bp.

The PCR products were analyzed by 5% polyacrylamide gel electrophoresis (5 µl/line), stained with ethidium bromide, and documented using BioImaging system (UVP). RT-PCR experiments were performed repeatedly with reproducible results. GAPDH served as a ubiquitously expressed control. Genomic contamination was ruled out by including an RT-negative sample (without reverse transcriptase, at the reverse transcription step) in each PCR set as a control.

Teratoma Formation and Evaluation

All animal procedures were carried out by the Biological Testing Laboratory-Branch of Shemyakin & Ovchinnikov Institute of Bioorganic Chemistry of the Russian Academy of Sciences (Pushchino, Moscow Region, Russia) accredited by the Association for the Assessment and Accreditation of Laboratory Animal Care International (AAALAC).

Immunodeficient SCID-beige mice which were bred from CB17/ICR-PRKDC-SCID CRL mice received from Charles River laboratories Research Model and Services (Germany) were used for teratoma formation. For injection into mice, the hpSC-Hhom were enzymatically separated from culture dishes using collagenase type IV and then resuspended into clumps. Approximately two to five million hpSC-Hhom cells were injected into the upper hind limb subcutaneous space. After approximately two months, established teratomas were removed and fixed with 4% paraformaldehyde. Half of the tissue was cryoprotected in sucrose and the other half was mounted in 5% agar-agar and then sectioned in 60 um slices using a vibratome. Sections were mounted on glass slides and stained with hematoxylin/eosin, Kraberg, Van Gieson and picrofucsin.

About two to five million mitornycinC treated human fibroblasts uses as feeder layers for the phES cells were injected as controls. No teratoma growth was observed in the control animals.

Example 1

Generation of Parthenotes

Five oocyte donors, all over 31 years of age, participated in this study. Oocytes were obtained using hormonal stimulation with the primary intent of in vitro fertilization (IVF). A total of 46 cumulus-oocyte complexes (COCs) were taken from five donors and used for this study (Table 1).

cysts (Kim et al., Stem Cells (2005) 23:1228-1233). Culture media and feeder cells may also contain animal pathogens. To eliminate possible contamination, researchers have used human cells as feeder instead of mouse fibroblasts (Cheng et al., Stem Cells (2003) 21:131-142; Hovatta et al., Hum Repro (2003) 18:1404-1429; Stojkovic et al., Stem Cells (2005) 23:306-314) or have cultured hESCs in feeder-free and serum-free conditions (Amit et al., 2004; Klimanskaya et al., Lancet (2005) 365:1636-1641). Taking into account these previous investigations, culture conditions for isolation of the ICM and phESC were modified.

For the derivation and culture of phESC mitomycin C mitotically inactivated human neonatal skin fibroblasts were used (NSF) as feeder cells. These cells originally, were derived and propagated with medium containing human umbilical cord blood serum instead of animal serum. The phESC culture medium consisted of VitroHES medium

TABLE 1

Generation of parthenotes and parthenogenetic embryonic stem cell lines.

| Donor | Oocytes derived | Oocytes donated | Oocytes activated | Parthenotes created[5] | Blastocysts derived[6] with ICM | Blastocysts derived[6] without visible ICM | Lines generated | Donor destiny |
|---|---|---|---|---|---|---|---|---|
| 1 | 8 | 4 | 4 | 4 | 2 | — | phESC-1 immunosurgery | pregnant |
| 2 | 15 | 8 | 8 | 8 | 3 | 3 | phESC-3 phESC-4 phESC-5 all from whole blastocysts | pregnant twins |
| 3 | 27 | 14 | 14[1,a] | 11 | 3 | 2 | phESC-6 from whole blastocyst | pregnant |
| 4 | 22 | 11 | 11[3] | 10 | 2 | 3 | phESC-7 from whole blastocyst | pregnant |
| 5 | 20 | 9[4] | 7 | 7 | 1 | 4 | no cell line generated | not pregnant |

[1] two oocytes were not activated;
[2] one oocyte degenerated after activation;
[3] one oocyte was not activated;
[4] two oocytes were at metaphase I stage and were discarded;
[5] total pathenogenetically activated oocytes = 40;
[6] total blastocytst derived = 23

Before oocyte activation, COCs were held at atmospheric oxygen tension. After removal of cumulus cells only normal metaphase II oocytes with distinct first polar body were taken for activation procedure. Oocytes were activated with 5 μM ionomycin for five minutes followed by incubation with am 6-DAMP for four hours to prevent the extrusion of the second polar body and produce diploid embryos. Manipulation and culture of oocytes and embryos was performed in Medical media in accordance with manufacturer's recommendations using standard IVF procedures and under reduced oxygen (90% $N_2$+5% $O_2$+5% $CO_2$). Only 40 oocytes were capable of cleavage after parthenogenetic activation. These procedures permitted the production of 23 blastocysts on five or six day of embryo culture. Eleven of the blastocysts had visible ICMs (Table 1).

Derivation of Parthenogenetic hESC Lines

It is very important to minimize if not eliminate components of animal origin in the derivation and culture of hESCs destined for clinical use. To this end, some researchers did not use immunosurgery for ICM isolation, but rather used mechanical means to isolate the ICMs from whole blasto- (Vitrolife) supplemented with human serum derived from umbilical cord blood, hrbFGF and hrLIF. The phESC were propagated in a 37° C., 5% C02, humidified atmosphere.

All derived parthenogenetic blastocysts were initially treated with 0.5% pronase to remove the zona pellucida. Well-formed ICMs from two blastocysts were obtained from the first oocyte donor using trypsin treatment (Li et al., Mol Reprod Dev (2003) 65:429-434) and traditional immunosurgery (Solter and Knowles, Proc Natl Acad Sci USA (1975) 72:5099-5102). The ICMs were further placed on human feeder cells at described conditions to produce phESC. The ICM from trypsin treated blastocyst did not give live cells. The ICM derived after immunosurgery displayed cell outgrowth, resulting in the creation of the phESC-1 cell line. The other 21 whole blastocysts were initially placed on the feeder at described conditions. The ICMs were isolated by mechanical slicing from sprawled trophoblast cells and replaced onto fresh feeder cells. Five phESC lines (from phESC-3 to phESC-7) were generated in this manner (Table 1).

The Characterization of phESC Lines

Figure 2:
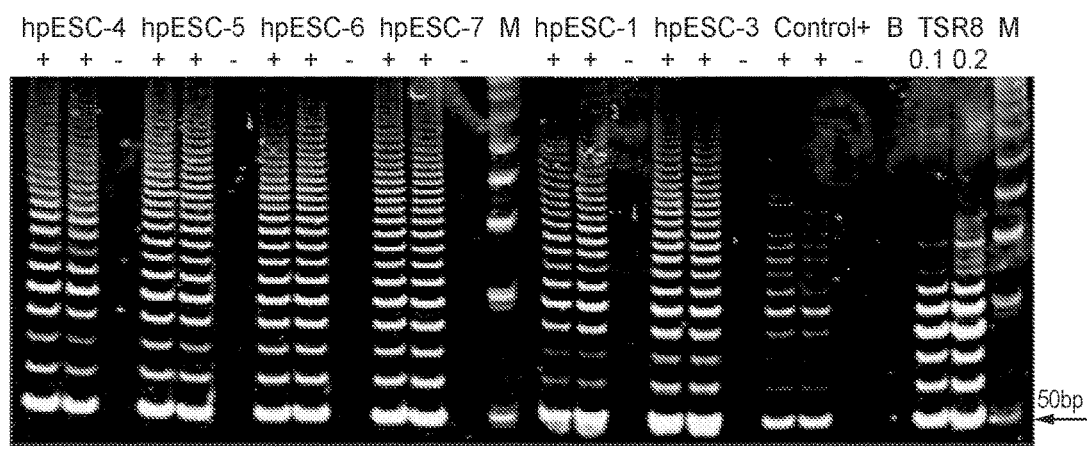
FIG. 2 shows that the phESC demonstrate high level of telomerase activity by comparison with positive control cells: "+"—the extract from 500 cells; "–"—heat-treated cell extract with inactivated telomerase; "Control+"—telomerase positive cell extract (applied with TRAPEZE Kit); "B"—CHAPS lysis buffer, primer-dimer/PCR contamination control; TSR8-telomerase quantitative control template (0.1 and 0.2 amole/μl); "M"—marker, DNA ladder.

The phESC lines display a morphology expected in hESCs and form colonies with tightly packed cells, prominent nucleoli and a small cytoplasm to nucleus ratio (FIG. 1). These cells express traditional hES cell markers SSEA-3, SSEA-4, (FIG. 1) TRA-1-60, TRA-1-81 and OCT-4, (FIG. 1 cont.) and do not express SSEA-1, a positive marker for undifferentiated mouse embryonic stem cells (FIG. 1). The cells derived from all lines demonstrate high levels of alkaline phosphatase (FIG. 1 cont.) and telomerase activity (FIG. 2).

Figure 3:
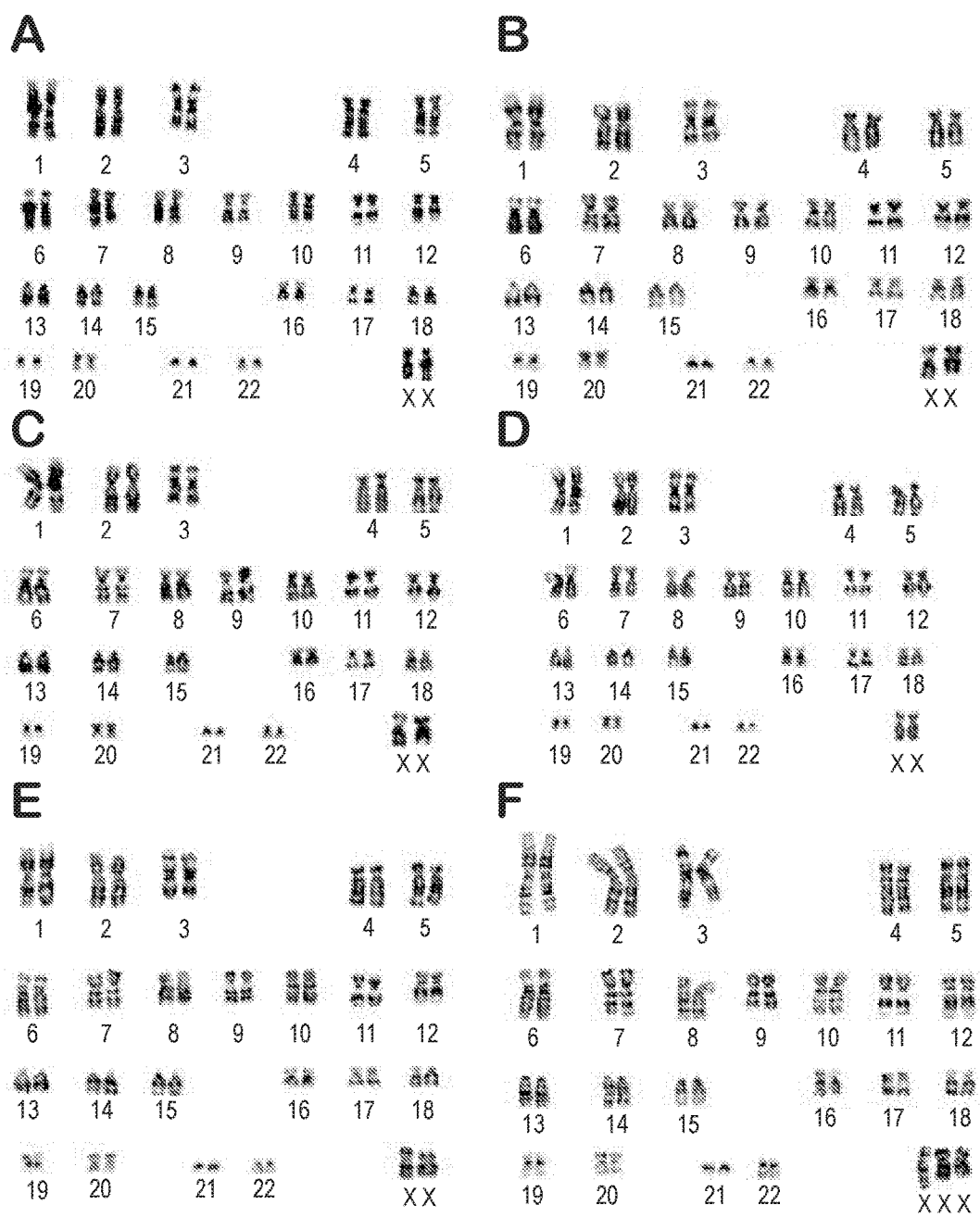
FIG. 3 shows the G-banded karyotyping for phESC lines. The phESC-1 (A), phESC-3 (B), phESC-4 (C), phESC-5 (D) and phESC-6 (E) lines have a normal 46, XX karyotype. The phESC-7 line has 47,XXX karyotype (F).

G-banded karyotyping showed that phESC lines have a normal human 46,XX karyotype, with the exception of the phESC-7 line (FIG. 3). Approximately 91% of cells from the phESC-7 line have a 47,XXX karyotype and 9% of the cells have a 48,XXX,+6 karyotype. A different degree of X chromosome heteromorphism was observed by analysis of 100 metaphases in the cell lines: approximately 12% of cells for the phESC-1 and phESC-6 lines showed X chromosome heteromorphism; 42% of cells for the phESC-5 line and in 70%, 80%, and 86% for the cell lines phESC-7, phESC-3 and phESC-4 respectively showed X chromosome heteromorphism (FIG. 3).

Differentiation Capacity of phESC

Figure 4:
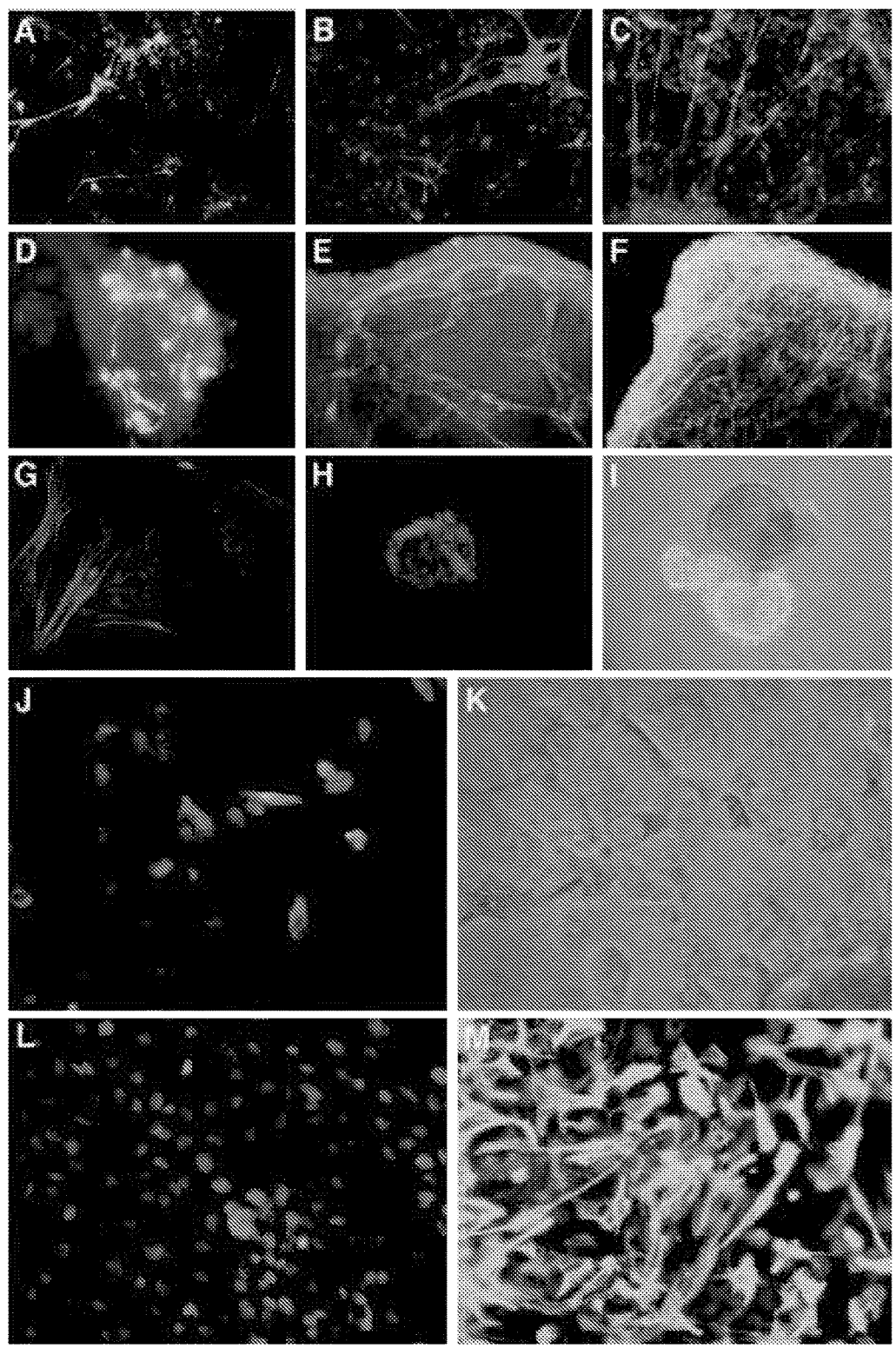
FIG. 4 shows the in vitro differentiation of phESC into derivatives of all three germ layers. Ectoderm differentiation is presented by positive immunocytochemical staining for neuron specific markers neurofilament 68 (A), NCAM (B), beta III tubulin (C) and glial cell marker GFAP (D, M). Differentiated cells were positive for mesoderm markers: muscle specific alpha-actinin (G) and desmin (J), endothelial markers PECAM-1 (E) and VE-Cadherin (F). Endoderm differentiation is presented by positive staining for alpha-fetoprotein (H, L). The phESC produce pigmented epithelial-like cells (I, K). Magnification (I) ×100; (A-H, J-M) ×400.
Figure 5:
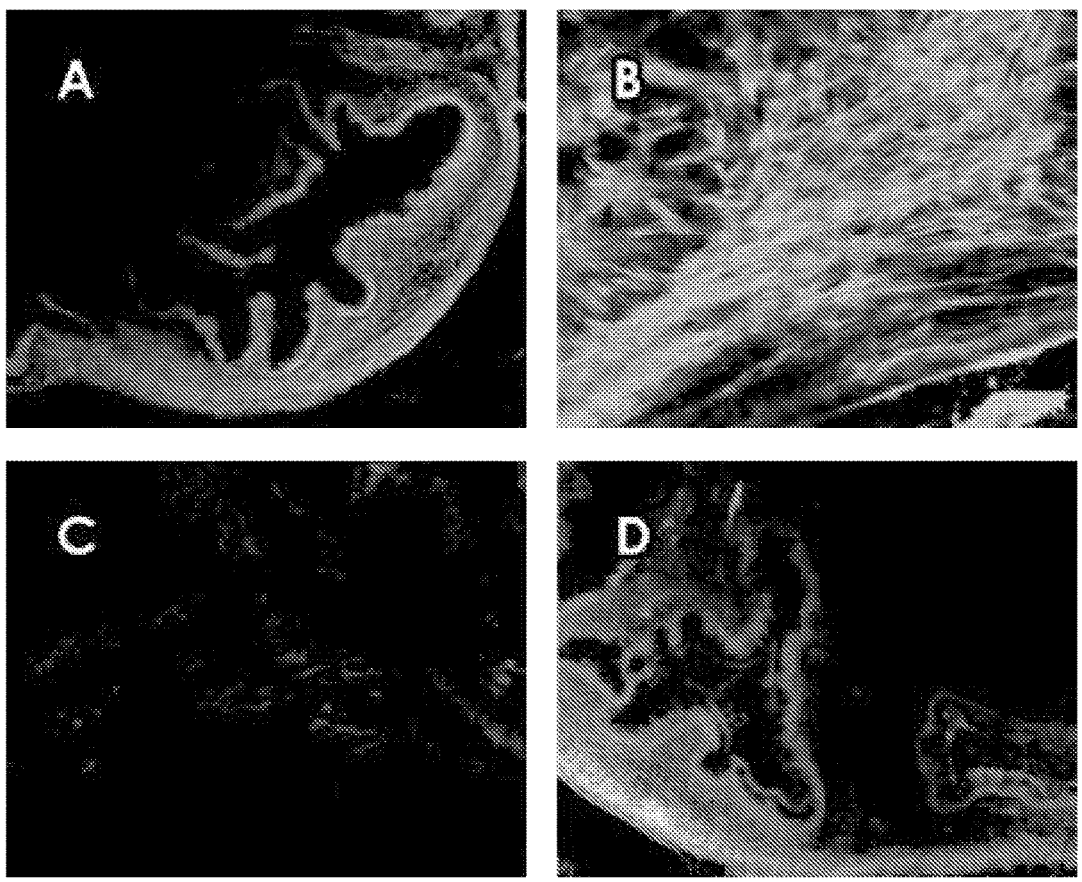
FIG. 5 shows the in vivo differentiation of phESC and teratoma formation in SCID mice. Immunofluorescence staining for the markers of three germ layers. The muscle actin, a mesodermal cell marker, is organized surrounding other components and is clearly identifiable (A). The presence of fibronectin in higher quantities is specific for connective tissue of mesodermal origin (B). The areas of neural differentiated cells (ectodermal origin) are extensive and labeled intensively with antibodies for beta tubulin (C). Alpha-fetoprotein, an immature endodermal cell marker, can be retrieved in areas of glandular appearance (D). The nuclei were stained with DAPI-(A), (D). Magnification (A), (C), (D) ×100; (B) ×200.

The phESC-1 line remained undifferentiated during ten months of culture spanning 35 passages. The other cell lines were successfully cultivated over at least 21 passages. The cells from all phESC lines formed cystic embryoid bodies in suspension culture and gave rise to derivatives of all three germ layers, ectoderm, mesoderm and endoderm, after differentiation in vitro (FIG. 4). Approximately 5% of embryoid bodies from the phESC-1 line gave rise to beating cells five days following plating. The phESC-6 line produced pigmented epithelial-like cells (FIG. 4 L, K). Ectoderm differentiation is presented by positive immunocytochemical staining for neuron specific markers neurofilament 68 (FIG. 4A), NCAM (FIG. 4B), beta III-tubulin (FIG. 4C) and the glial cell marker GFAP (FIG. 4D, M). Differentiated cells were positive for mesoderm markers including alpha-actinin (FIG. 4G) and desmin (FIG. 4J), which are muscle-specific markers, and the endothelial markers PEC AM-1 (FIG. 4E) and VE-Cadherin (FIG. 4F). Endoderm differentiation is presented by positive staining of differentiated derivatives for alpha-fetoprotein (FIG. 4H, L). The ability of phESC lines to form derivatives from all three germ layers was investigated in vivo by subcutaneous injection of phESC into immunodeficient mice and rats (FIG. 5). Cells from all phESC lines were capable of forming teratomas approximately two months after injection. Histological examination demonstrated the presence of organized structures, including: epithelia; capsula; smooth muscle; adipose tissue; hematogenic tissue; neural tubes and glandular epithelia. Immunohistochemical analysis revealed positive staining for beta-tubulin (FIG. 5C)—ectoderm marker; fibronectin (FIG. 5B) and muscle actin (FIG. 5A)—mesoderm markers; and alpha-fetoprotein (FIG. 5D)—endoderm marker. These data demonstrate that phESC can be differentiated in vivo into the three germ layers that lead to all cell types found in a human body.

DNA-Profiling of phESC Lines

Comparative DNA-profiling of all the phESC lines, the donor somatic cells and the feeder cells was performed. These studies used Affymetrix single-nucleotide polymorphism (SNP) microarrays (Mapping 50K Hind 240 Arrays) to confirm the genetic similarity of the phESC to the donor's somatic cells. A total of 1459 SNP markers across 15 autosomes (chromosomes 1-15) were chosen with median intermarker distance of 1.12 Mbp. All paired genotype relationships between phESC lines and their associated donor somatic cells were identified as "full siblings" (genetically matched), and all the other combinations of pairs were identified as "unrelated". Internal controls identified the paired genotype relationship between split cultures derived from the same phESC line as "monozygous twins" (Table 2).

TABLE 2

Identifying DNA samples from phESC and related donors.

| geno-type 1 | geno-type 2 | putative relationship | inferred relationship | IBS 0 | IBS 1 | IBS 2 | n_typed | MZtwins | par/off | fullsibs | halfsibs | unrelated |
|---|---|---|---|---|---|---|---|---|---|---|---|---|
| 1 | 2 | unrelated | unrelated | 166 | 662 | 631 | 1459 | −1503.03 | −300.45 | −23.15 | −8.41 | 0 |
| 1 | 3 | unrelated | unrelated | 241 | 616 | 602 | 1459 | −1560.65 | −434.85 | −28.04 | −12.22 | 0 |
| 1 | 4 | unrelated | unrelated | 225 | 623 | 611 | 1459 | −1535.94 | −400.61 | −31.39 | −14.39 | 0 |
| 1 | 5 | unrelated | unrelated | 225 | 623 | 611 | 1459 | −1535.94 | −400.61 | −31.39 | −14.39 | 0 |
| 1 | 6 | unrelated | unrelated | 243 | 644 | 572 | 1459 | −1642.35 | −445.78 | −31.74 | −14.54 | 0 |
| 1 | 7 | unrelated | unrelated | 252 | 638 | 569 | 1459 | −1641.11 | −453.5 | −29.25 | −12.86 | 0 |
| 1 | 8 | unrelated | unrelated | 250 | 643 | 566 | 1459 | −1656.02 | −460.02 | −32.86 | −15.32 | 0 |
| 1 | 9 | unrelated | unrelated | 219 | 657 | 583 | 1459 | −1605.31 | −382.39 | −27.37 | −11.58 | 0 |
| 1 | 10 | unrelated | unrelated | 158 | 707 | 594 | 1459 | −1591.43 | −279.21 | −26.37 | −10..89 | 0 |
| 1 | 11 | unrelated, | unrelated | 193 | 668 | 598 | 1459 | −1584.71 | −354.76 | −29.65 | −13..31 | 0 |
| 1 | 12 | unrelated | unrelated | 166 | 671 | 622 | L459 | −1523.1 | −300.5 | −30.53 | −13..92 | 0 |
| 2 | 3 | unrelated | fullsibs | 0 | 282 | 1177 | 1459 | −440.02 | −146.3 | 0 | −167.42 | −363.63 |
| 2 | 4 | unrelated | unrelated | 233 | 627 | 599 | 1459 | −1569.66 | −423.24 | −28.24 | −12.91 | 0 |
| 2 | 5 | unrelated | unrelated | 233 | 627 | 599 | 1459 | −1569.66 | −423.24 | −28.24 | −12.91 | 0 |
| 2 | 6 | unrelated | unrelated | 217 | 650 | 592 | 1459 | −1584.75 | −388.44 | −22.62 | −8.53 | 0 |
| 2 | 7 | unrelated | unrelated. | 243 | 650 | 566 | 1459 | −1645.94 | −437.91 | −23.23 | −8.72 | 0 |
| 2 | 8 | unrelated | unrelated | 225 | 649 | 585 | 1459 | −1603.18 | −404.41 | −27.04 | −11.97 | 0 |
| 2 | 9 | unrelated | unrelated | 210 | 639 | 610 | 1459 | −1532.75 | −360.46 | −24.72 | −9.89 | 0 |
| 2 | 10 | unrelated | unrelated | 144 | 683 | 632 | 1459 | −1491.18 | −243.56 | −16.82 | −4.51 | 0 |
| 2 | 11 | unrelated | unrelated | 172 | 680 | 607 | 1459 | −1556.46 | −310.03 | −23.5 | −9.7 | 0 |
| 2 | 12 | unrelated | unrelated | 176 | 667 | 616 | 1459 | −1538.57 | −327.95 | −27.31 | −12..06 | 0 |
| 3 | 4 | unrelated | unrelated | 336 | 457 | 666 | 1459 | −1391.57 | −599.92 | −30.6 | −14.62 | 0 |
| 3 | 5 | unrelated | unrelated | 336 | 457 | 666 | 1459 | −1391.57 | −599.92 | −30.6 | −14.62 | 0 |
| 3 | 6 | unrelated | unrelated | 322 | 482 | 655 | 1459 | −1415.98 | −571.23 | −26.08 | −11.86 | 0 |
| 3 | 7 | unrelated | unrelated | 369 | 442 | 648 | 1459 | −1432.05 | −664.95 | −27.39 | −11.93 | 0 |
| 3 | 8 | unrelated | unrelated | 334 | 483 | 642 | 1459 | −1449.86 | −597.75 | −31.68 | −15.14 | 0 |
| 3 | 9 | unrelated | unrelated | 307 | 493 | 659 | 1459 | −1395.19 | −530.45 | −24.56 | −10 | 0 |

TABLE 2-continued

Identifying DNA samples from phESC and related donors.

| geno-type 1 | geno-type 2 | putative relationship | inferred relationship | IBS 0 | IBS 1 | IBS 2 | n_typed | LOD MZtwins | LOD par/off | LOD fullsibs | LOD halfsibs | LOD unrelated |
|---|---|---|---|---|---|---|---|---|---|---|---|---|
| 3 | 10 | unrelated | unrelated | 215 | 623 | 621 | 1459 | −1503.92 | −364.97 | −17.26 | −4.43 | 0 |
| 3 | 11 | unrelated | unrelated | 264 | 582 | 613 | 1459 | −1531.91 | −473.48 | −28.41 | −12..81 | 0 |
| 3 | 12 | unrelated | unrelated | 254 | 595 | 610 | 1459 | −1544.73 | −460.57 | −29.92 | −13..88 | 0 |
| 4 | 5 | unrelated | MZ twins | 0 | 0 | 1459 | 1459 | 0 | −379.58 | −45.47 | −401.67 | −677.74 |
| 4 | 6 | unrelated | unrelated | 334 | 475 | 650 | 1459 | −1436.59 | −599.55 | −32.73 | −15.19 | 0 |
| 4 | 7 | unrelated | unrelated | 365 | 439 | 655 | 1459 | −1418.34 | −656.01 | −31.6 | −14.56 | 0 |
| 4 | 8 | unrelated | unrelated | 329 | 486 | 644 | 1459 | −1450.75 | −586.4 | −32.06 | −14.88 | 0 |
| 4 | 9 | unrelated | unrelated | 332 | 466 | 661 | 1459 | −1395.18 | −590.12 | −28.69 | −12.94 | 0 |
| 4 | 10 | unrelated | unrelated | 245 | 606 | 608 | 1459 | −1542.32 | −438.93 | −28.75 | −12..74 | 0 |
| 4 | 11 | unrelated | unrelated | 273 | 569 | 617 | 1459 | −1530.97 | −492.84 | −29.03 | −12..34 | 0 |
| 4 | 12 | unrelated | full sibs | 0 | 224 | 1235 | 1459 | −326.17 | −162.34 | 0 | −183.44 | −393.46 |
| 5 | 6 | unrelated | unrelated | 334 | 475 | 650 | 1459 | −1436.59 | −599.55 | −32.73 | −15.19 | 0 |
| 5 | 7 | unrelated | unrelated | 365 | 439 | 655 | 1459 | −1418.34 | −656.01 | −31.6 | −14.56 | 0 |
| 5 | 8 | unrelated | unrelated | 329 | 486 | 644 | 1459 | −1450.75 | −586.4 | −32.06 | −14.88 | 0 |
| 5 | 9 | unrelated | unrelated | 332 | 466 | 661 | 1459 | −1395.18 | −590.12 | −28.69 | −12.94 | 0 |
| 5 | 10 | unrelated | unrelated | 245 | 606 | 608 | 1459 | −1542.32 | −438.93 | −28.75 | −12..74 | 0 |
| 5 | 11 | unrelated | unrelated | 273 | 569 | 617 | 1459 | −1530.97 | −492.84 | −29.03 | −12..34 | 0 |
| 5 | 12 | unrelated | full sibs | 0 | 224 | 1235 | 1459 | −326.17 | −162.34 | 0 | −183.44 | −393.46 |
| 6 | 7 | unrelated | full sibs | 45 | 176 | 1238 | 1459 | −277.78 | −217.21 | 0 | −165.72 | −390.62 |
| 6 | 8 | unrelated | fullsibs | 44 | 187 | 1228 | 1459 | −289.8 | −201.32 | 0 | −153.75 | −365.51 |
| 6 | 9 | unrelated | unrelated | 333 | 481 | 645 | 1459 | −1436.5 | −595.4 | −30.3 | −13.77 | 0 |
| 6 | 10 | unrelated | unrelated | 240 | 601 | 618 | 1459 | −1518.17 | −425.03 | −27.11 | −11..53 | 0 |
| 6 | 11 | unrelated | full sibs | 0 | 164 | 1295 | 1459 | −209.27 | −191.66 | 0 | −213.25 | −440.56 |
| 6 | 12 | unrelated | unrelated | 234 | 615 | 610 | 1459 | −1547.15 | −416.14 | −30.21 | −13..64 | 0 |
| 7 | 8 | unrelated | full sibs | 38 | 225 | 1196 | 1459 | −326.62 | −150.16 | 0 | −121.55 | −334.09 |
| 7 | 9 | unrelated | unrelated | 359 | 473 | 627 | 1459 | −1479.28 | −642.41 | −30.61 | −14.47 | 0 |
| 7 | 10 | unrelated | unrelated | 252 | 623 | 584 | 1459 | −1598.35 | −443.81 | −28.88 | −13..09 | 0 |
| 7 | 11 | unrelated | fullsibs | 0 | 230 | 1229 | 1459 | −318.49 | −137.93 | 0 | −159.55 | −389.58 |
| 7 | 12 | unrelated | unrelated | 265 | 583 | 611 | 1459 | −1539.33 | −472.91 | −30.55 | −13..87 | 0 |
| 8 | 9 | unrelated | unrelated | 347 | 480 | 632 | 1459 | −1472.41 | −625.68 | −30.93 | −14.31 | 0 |
| 8 | 10 | unrelated | unrelated | 244 | 614 | 601 | 1459 | −1561.3 | −434 | −28.07 | −12..37 | 0 |
| 8 | 11 | unrelated | full sibs | 0 | 175 | 1284 | 1459 | −223.73 | −178.56 | 0 | −200.12 | −428.04 |
| 8 | 12 | unrelated | unrelated | 236 | 610 | 613 | 1459 | −1539.08 | −417.14 | −29.32 | −13..14 | 0 |
| 9 | 10 | unrelated | fullsibs | 0 | 228 | 1231 | 1459 | −315.15 | −152.88 | 0 | −174.27 | −392.91 |
| 9 | 11 | unrelated | unrelated | 269 | 567 | 623 | 1459 | −1502.69 | −479.57 | −28.47 | −12..55 | 0 |
| 9 | 12 | unrelated | unrelated | 245 | 612 | 602 | 1459 | −1557.25 | −438.53 | −26.07 | −11..15 | 0 |
| 10 | 11 | unrelated | unrelated | 187 | 635 | 637 | 1459 | −1478.7 | −328.06 | −25.52 | −10.6 | 0 |
| 10 | 12 | unrelated | unrelated | 181 | 662 | 616 | 1459 | −1534.36 | −329 | −25.2 | −10.6 | 0 |
| 11 | 12 | unrelated | unrelated | 189 | 645 | 625 | 1459 | −1520.01 | −337.88 | −27.33 | −11.72 | 0 |

DNA samples analyzed were numbered as follows: 1- human neonatal skin fibroblasts, 2- phESC-7 line donor, 3-phESC-7 line, 4- phESC-1 line, 5- phESC-1 line, 6- phESC-3 line, 7- phESC-4 line, 8- phESC-5 line, 9- phESC-6 line, 10- phESC-6 line donor, 11- phESC-3 to phESC-5 lines donor, 12-phESC-1 line donor. The IBS columns in the output display the number of markers at which the pair are both typed and share 0, 1, or 2 alleles identical by state. (For MZ twins under the ideal condition of no genotyping errors, all markers must be placed under IBS = 2.)
The output does not display P (observed markers l given relationship) directly, but it displays LOD score = $\log_{10}$ {P(observed markers l putative relationship)/P(observed markers l relationship for which maximum likelihood was obtained and thus the call was made)} as a measure of similarity. The smaller this LOD score is, the less likely is the putative relationship between two samples.

Comparative analysis of SNP markers revealed, that on the whole, donor cells do not seem to exhibit a clear pattern of heterozygosity trend across distances from centromeres, whereas stem cells display somewhat lower proportions of heterozygosity near centromeres and telomeres in comparison to heterozygosity proportions in the middle as a result of probable chromosome recombination (Tables A-I).

TABLE A

Heterozygous Donor/Stem Chromosome Bins.
hetero donor stem chr bin

| chr | Bins | freq | Donorhetero | Stemhetero |
|---|---|---|---|---|
|  |  | 1459 | 0.37 | 0.207 |
|  | 10 | 91 | 0.407 | 0.053 |
|  | 20 | 135 | 0.33 | 0.111 |
|  | 30 | 185 | 0.358 | 0.19 |
|  | 40 | 169 | 0.408 | 0.285 |
|  | 50 | 157 | 0.385 | 0.268 |
|  | 60 | 153 | 0.353 | 0.204 |
|  | 70 | 123 | 0.354 | 0.188 |
|  | 80 | 113 | 0.345 | 0.239 |
|  | 90 | 118 | 0.371 | 0.228 |

TABLE A-continued

Heterozygous Donor/Stem Chromosome Bins.
hetero donor stem chr bin

| chr | Bins | freq | Donorhetero | Stemhetero |
|---|---|---|---|---|
|  | 100 | 88 | 0.398 | 0.24 |
|  | 110 | 49 | 0.393 | 0.233 |
|  | 120 | 29 | 0.302 | 0.222 |
|  | 130 | 26 | 0.365 | 0.231 |
|  | 140 | 20 | 0.4 | 0.193 |
|  | 150 | 3 | 0.5 | 0.048 |
| 1 |  | 142 | 0.373 | 0.198 |
| 2 |  | 150 | 0.327 | 0.187 |
| 3 |  | 111 | 0.41 | 0.229 |
| 4 |  | 133 | 0.346 | 0.179 |
| 5 |  | 121 | 0.39 | 0.263 |
| 6 |  | 115 | 0.387 | 0.205 |
| 7 |  | 103 | 0.379 | 0.205 |
| 8 |  | 93 | 0.401 | 0.187 |
| 9 |  | 66 | 0.314 | 0.171 |
| 10 |  | 88 | 0.375 | 0.273 |
| 11 |  | 78 | 0.385 | 0.19 |
| 12 |  | 77 | 0.403 | 0.161 |
| 13 |  | 78 | 0.324 | 0.192 |

TABLE A-continued

Heterozygous Donor/Stem Chromosome Bins.
hetero donor stem chr bin

| chr | Bins | freq | Donorhetero | Stemhetero |
|---|---|---|---|---|
| 14 |  | 62 | 0.379 | 0.279 |
| 15 |  | 42 | 0.345 | 0.194 |
| 1 | 20 | 9 | 0.361 | 0.063 |
| 1 | 30 | 14 | 0.357 | 0.153 |
| 1 | 40 | 12 | 0.354 | 0.214 |
| 1 | 50 | 15 | 0.35 | 0.229 |
| 1 | 60 | 21 | 0.369 | 0.211 |
| 1 | 70 | 19 | 0.461 | 0.211 |
| 1 | 80 | 9 | 0.333 | 0.175 |
| 1 | 90 | 13 | 0.288 | 0.176 |
| 1 | 100 | 13 | 0.327 | 0.198 |
| 1 | 110 | 8 | 0.469 | 0.214 |
| 1 | 120 | 6 | 0.333 | 0.19 |
| 1 | 130 | 3 | 0.667 | 0.571 |
| 2 | 10 | 3 | 0.333 | 0 |
| 2 | 20 | 11 | 0.386 | 0.182 |
| 2 | 30 | 13 | 0.269 | 0.176 |
| 2 | 40 | 6 | 0.25 | 0.167 |
| 2 | 50 | 19 | 0.303 | 0.263 |
| 2 | 60 | 13 | 0.423 | 0.308 |
| 2 | 70 | 10 | 0.275 | 0.171 |
| 2 | 80 | 13 | 0.327 | 0.176 |
| 2 | 90 | 19 | 0.342 | 0.226 |
| 2 | 100 | 7 | 0.214 | 0.082 |
| 2 | 110 | 4 | 0.375 | 0.143 |
| 2 | 120 | 7 | 0.25 | 0.122 |
| 2 | 130 | 11 | 0.318 | 0.143 |
| 2 | 140 | 11 | 0.386 | 0.156 |
| 2 | 150 | 3 | 0.5 | 0.048 |
| 3 | 10 | 9 | 0.417 | 0.016 |
| 3 | 20 | 15 | 0.333 | 0.057 |
| 3 | 30 | 12 | 0.354 | 0.167 |
| 3 | 40 | 11 | 0.455 | 0.351 |
| 3 | 50 | 3 | 0.083 | 0.143 |
| 3 | 60 | 12 | 0.438 | 0.286 |
| 3 | 70 | 12 | 0.458 | 0.202 |
| 3 | 80 | 14 | 0.5 | 0.347 |
| 3 | 90 | 12 | 0.375 | 0.25 |
| 3 | 100 | 9 | 0.472 | 0.429 |
| 3 | 110 | 2 | 0.375 | 0.286 |
| 4 | 10 | 13 | 0.423 | 0.121 |
| 4 | 20 | 9 | 0.25 | 0.143 |
| 4 | 30 | 15 | 0.283 | 0.152 |
| 4 | 40 | 15 | 0.367 | 0.2 |
| 4 | 50 | 11 | 0.409 | 0.195 |
| 4 | 60 | 8 | 0.375 | 0.179 |
| 4 | 70 | 7 | 0.286 | 0.163 |
| 4 | 80 | 9 | 0.278 | 0.206 |
| 4 | 90 | 9 | 0.389 | 0.222 |
| 4 | 100 | 7 | 0.321 | 0.204 |
| 4 | 110 | 8 | 0.375 | 0.196 |
| 4 | 120 | 7 | 0.321 | 0.184 |
| 4 | 130 | 8 | 0.313 | 0.179 |
| 4 | 140 | 7 | 0.429 | 0.204 |
| 5 | 10 | 12 | 0.417 | 0.083 |
| 5 | 20 | 12 | 0.292 | 0.119 |
| 5 | 30 | 11 | 0.409 | 0.325 |
| 5 | 40 | 14 | 0.411 | 0.306 |
| 5 | 50 | 10 | 0.45 | 0.257 |
| 5 | 60 | 8 | 0.219 | 0.107 |
| 5 | 70 | 8 | 0.344 | 0.25 |
| 5 | 80 | 8 | 0.406 | 0.339 |
| 5 | 90 | 8 | 0.375 | 0.214 |
| 5 | 100 | 7 | 0.536 | 0.286 |
| 5 | 110 | 9 | 0.5 | 0.508 |
| 5 | 120 | 8 | 0.344 | 0.393 |
| 5 | 130 | 4 | 0.375 | 0.321 |
| 5 | 140 | 2 | 0.375 | 0.357 |
| 6 | 10 | 13 | 0.404 | 0.022 |
| 6 | 20 | 14 | 0.286 | 0.082 |
| 6 | 30 | 11 | 0.364 | 0.208 |
| 6 | 40 | 12 | 0.542 | 0.488 |
| 6 | 50 | 10 | 0.4 | 0.329 |
| 6 | 60 | 18 | 0.347 | 0.19 |
| 6 | 70 | 8 | 0.344 | 0.161 |
| 6 | 80 | 8 | 0.25 | 0.179 |
| 6 | 90 | 7 | 0.429 | 0.245 |
| 6 | 100 | 10 | 0.55 | 0.229 |
| 6 | 110 | 4 | 0.313 | 0.143 |
| 7 | 10 | 6 | 0.292 | 0.024 |
| 7 | 20 | 12 | 0.333 | 0.071 |
| 7 | 30 | 16 | 0.313 | 0.143 |
| 7 | 40 | 14 | 0.429 | 0.337 |
| 7 | 50 | 16 | 0.484 | 0.402 |
| 7 | 60 | 15 | 0.433 | 0.171 |
| 7 | 70 | 9 | 0.389 | 0.19 |
| 7 | 80 | 5 | 0.3 | 0.171 |
| 7 | 90 | 7 | 0.214 | 0.061 |
| 7 | 100 | 3 | 0.5 | 0.381 |
| 8 | 10 | 8 | 0.313 | 0.036 |
| 8 | 20 | 10 | 0.425 | 0.129 |
| 8 | 30 | 15 | 0.483 | 0.162 |
| 8 | 40 | 13 | 0.346 | 0.253 |
| 8 | 50 | 11 | 0.364 | 0.208 |
| 8 | 60 | 4 | 0.25 | 0.143 |
| 8 | 70 | 10 | 0.45 | 0.314 |
| 8 | 80 | 6 | 0.375 | 0.167 |
| 8 | 90 | 11 | 0.455 | 0.169 |
| 8 | 100 | 5 | 0.4 | 0.257 |
| 9 | 20 | 9 | 0.25 | 0.016 |
| 9 | 30 | 15 | 0.35 | 0.133 |
| 9 | 40 | 10 | 0.45 | 0.229 |
| 9 | 50 | 13 | 0.269 | 0.209 |
| 9 | 60 | 9 | 0.278 | 0.254 |
| 9 | 70 | 6 | 0.25 | 0.167 |
| 9 | 80 | 4 | 0.313 | 0.214 |
| 10 | 10 | 7 | 0.5 | 0.163 |
| 10 | 20 | 15 | 0.367 | 0.181 |
| 10 | 30 | 19 | 0.289 | 0.248 |
| 10 | 40 | 12 | 0.375 | 0.298 |
| 10 | 50 | 6 | 0.5 | 0.381 |
| 10 | 60 | 9 | 0.333 | 0.349 |
| 10 | 70 | 2 | 0.375 | 0.286 |
| 10 | 80 | 8 | 0.406 | 0.393 |
| 10 | 90 | 7 | 0.357 | 0.286 |
| 10 | 100 | 3 | 0.5 | 0.238 |
| 11 | 10 | 7 | 0.357 | 0.02 |
| 11 | 20 | 8 | 0.375 | 0.161 |
| 11 | 30 | 15 | 0.45 | 0.267 |
| 11 | 40 | 15 | 0.4 | 0.219 |
| 11 | 50 | 16 | 0.469 | 0.268 |
| 11 | 60 | 7 | 0.143 | 0.061 |
| 11 | 70 | 6 | 0.333 | 0.119 |
| 11 | 80 | 4 | 0.313 | 0.179 |
| 12 | 10 | 13 | 0.481 | 0.011 |
| 12 | 20 | 9 | 0.306 | 0.143 |
| 12 | 30 | 13 | 0.385 | 0.132 |
| 12 | 40 | 12 | 0.458 | 0.226 |
| 12 | 50 | 9 | 0.5 | 0.238 |
| 12 | 60 | 5 | 0.25 | 0.114 |
| 12 | 70 | 7 | 0.214 | 0.163 |
| 12 | 80 | 3 | 0.333 | 0.333 |
| 12 | 90 | 4 | 0.563 | 0.393 |
| 12 | 100 | 2 | 0.5 | 0.071 |
| 13 | 20 | 1 | 0.25 | 0 |
| 13 | 30 | 4 | 0.375 | 0.179 |
| 13 | 40 | 10 | 0.325 | 0.214 |
| 13 | 50 | 7 | 0.393 | 0.306 |
| 13 | 60 | 9 | 0.25 | 0.048 |
| 13 | 70 | 8 | 0.344 | 0.143 |
| 13 | 80 | 9 | 0.25 | 0.27 |
| 13 | 90 | 7 | 0.464 | 0.429 |
| 13 | 100 | 11 | 0.341 | 0.208 |
| 13 | 110 | 11 | 0.295 | 0.065 |
| 13 | 120 | 1 | 0 | 0 |
| 14 | 20 | 1 | 0.25 | 0.143 |
| 14 | 30 | 7 | 0.429 | 0.265 |
| 14 | 40 | 8 | 0.531 | 0.518 |
| 14 | 50 | 8 | 0.344 | 0.321 |
| 14 | 60 | 9 | 0.444 | 0.27 |

TABLE A-continued

Heterozygous Donor/Stem Chromosome Bins.
hetero donor stem chr bin

| chr | Bins | freq | Donorhetero | Stemhetero |
|---|---|---|---|---|
| 14 | 70 | 6 | 0.333 | 0.119 |
| 14 | 80 | 8 | 0.219 | 0.125 |
| 14 | 90 | 7 | 0.286 | 0.184 |
| 14 | 100 | 6 | 0.417 | 0.333 |
| 14 | 110 | 2 | 0.5 | 0-571 |
| 15 | 30 | 5 | 0.3 | 0.171 |
| 15 | 40 | 5 | 0.4 | 0.286 |
| 15 | 50 | 3 | 0.167 | 0.143 |
| 15 | 60 | 6 | 0.5 | 0.19 |
| 15 | 70 | 5 | 0.1 | 0.086 |
| 15 | 80 | 5 | 0.5 | 0.257 |
| 15 | 90 | 7 | 0.429 | 0.245 |
| 15 | 100 | 5 | 0.25 | 0.171 |
| 15 | 110 | 1 | 0.25 | 0 |

TABLE B

Chromosome Bins, Hetero/
Frequency at Chromosome 01.
hetero 01 chr bin

| Chr | bins | freq | Hetero01 |
|---|---|---|---|
|  |  | 1459 | 0.402 |
|  | 10 | 91 | 0.429 |
|  | 20 | 135 | 0.393 |
|  | 30 | 185 | 0.357 |
|  | 40 | 169 | 0.438 |
|  | 50 | 157 | 0.376 |
|  | 60 | 153 | 0.425 |
|  | 70 | 123 | 0.407 |
|  | 80 | 113 | 0.442 |
|  | 90 | 118 | 0.373 |
|  | 100 | 88 | 0.42 |
|  | 110 | 49 | 0.449 |
|  | 120 | 29 | 0.448 |
|  | 130 | 26 | 0.346 |
|  | 140 | 20 | 0.25 |
|  | 150 | 3 | 0.333 |
| 1 |  | 142 | 0.352 |
| 2 |  | 150 | 0.373 |
| 3 |  | 111 | 0.45 |
| 4 |  | 133 | 0.391 |
| 5 |  | 121 | 0.347 |
| 6 |  | 115 | 0.435 |
| 7 |  | 103 | 0.427 |
| 8 |  | 93 | 0.409 |
| 9 |  | 66 | 0.439 |
| 10 |  | 88 | 0.341 |
| 11 |  | 78 | 0.436 |
| 12 |  | 77 | 0.39 |
| 13 |  | 78 | 0.474 |
| 14 |  | 62 | 0.452 |
| 15 |  | 42 | 0.405 |
|  | 20 | 9 | 0.333 |
|  | 30 | 14 | 0.429 |
|  | 40 | 12 | 0.167 |
|  | 50 | 15 | 0.067 |
|  | 60 | 21 | 0.333 |
|  | 70 | 19 | 0.579 |
|  | 80 | 9 | 0.333 |
|  | 90 | 13 | 0.538 |
|  | 100 | 13 | 0.308 |
|  | 110 | 8 | 0.5 |
|  | 120 | 6 | 0.333 |
|  | 130 | 3 | 0 |
| 2 | 10 | 3 | 0.667 |
| 2 | 20 | 11 | 0.273 |
| 2 | 30 | 13 | 0.308 |
| 2 | 40 | 6 | 0.5 |
| 2 | 50 | 19 | 0.421 |
| 2 | 60 | 13 | 0.462 |

TABLE B-continued

Chromosome Bins, Hetero/
Frequency at Chromosome 01.
hetero 01 chr bin

| Chr | bins | freq | Hetero01 |
|---|---|---|---|
| 2 | 70 | 10 | 0.3 |
| 2 | 80 | .13 | 0.538 |
| 2 | 90 | 19 | 0.263 |
| 2 | 100 | .7 | 0.286 |
| 2 | 110 | 4 | 0.5 |
| 2 | 120 | 7 | 0.429 |
| 2 | 130 | 11 | 0.455 |
| 2 | 140 | 11 | 0.182 |
| 2 | 150 | 3 | 0.333 |
| 3 | 10 | 9 | 0.444 |
| 3 | 20 | 15 | 0.6 |
| 3 | 30 | 12 | 0.333 |
| 3 | 40 | 11 | 0.545 |
| 3 | 50 | 3 | 0.333 |
| 3 | 60 | 12 | 0.333 |
| 3 | 70 | 12 | 0.417 |
| 3 | 80 | 14 | 0.357 |
| 3 | 90 | 12 | 0.5 |
| 3 | 100 | 9 | 0.667 |
| 3 | 110 | 2 | 0 |
| 4 | 10 | 13 | 0.385 |
| 4 | 20 | 9 | 0.333 |
| 4 | 30 | 15 | 0.333 |
| 4 | 40 | 15 | 0.467 |
| 4 | 50 | 11 | 0.273 |
| 4 | 60 | 8 | 0.5 |
| 4 | 70 | 7 | 0.286 |
| 4 | 80 | 9 | 0.556 |
| 4 | 90 | 9 | 0.111 |
| 4 | 100 | 7 | 0.571 |
| 4 | 110 | 8 | 0.625 |
| 4 | 120 | 7 | 0.429 |
| 4 | 130 | 8 | 0.375 |
| 4 | 140 | 7 | 0.286 |
| 5 | 10 | 12 | 0.417 |
| 5 | 20 | 12 | 0.25 |
| 5 | 30 | 11 | 0.182 |
| 5 | 40 | 14 | 0.357 |
| 5 | 50 | 10 | 0.1 |
| 5 | 60 | 8 | 0.625 |
| 5 | 70 | 8 | 0.25 |
| 5 | 80 | 8 | 0.625 |
| 5 | 90 | 8 | 0.375 |
| 5 | 100 | 7 | 0 |
| 5 | 110 | 9 | 0.556 |
| 5 | 120 | 8 | 0.5 |
| 5 | 130 | 4 | 0.25 |
| 5 | 140 | 2 | 0.5 |
| 6 | 10 | 13 | 0.385 |
| 6 | 20 | 14 | 0.214 |
| 6 | 30 | 11 | 0.636 |
| 6 | 40 | 12 | 0.5 |
| 6 | 50 | 10 | 0.3 |
| 6 | 60 | 18 | 0.444 |
| 6 | 70 | 8 | 0.75 |
| 6 | 80 | 8 | 0.5 |
| 6 | 90 | 7 | 0.429 |
| 6 | 100 | 10 | 0.3 |
| 6 | 110 | 4 | 0.5 |
| 7 | 10 | 6 | 0.833 |
| 7 | 20 | 12 | 0.417 |
| 7 | 30 | 16 | 0.188 |
| 7 | 40 | 14 | 0.429 |
| 7 | 50 | 16 | 0.5 |
| 7 | 60 | 15 | 0.467 |
| 7 | 70 | 9 | 0.333 |
| 7 | 80 | 5 | 0.4 |
| 7 | 90 | 7 | 0.429 |
| 7 | 100 | 3 | 0.667 |
| 8 | 10 | 8 | 0.25 |
| 8 | 20 | 10 | 0.5 |
| 8 | 30 | 15 | 0.333 |
| 8 | 40 | 13 | 0.385 |
| 8 | 50 | 11 | 0.364 |

TABLE B-continued

Chromosome Bins, Hetero/Frequency at Chromosome 01.
hetero 01 chr bin

| Chr | bins | freq | Hetero01 |
|---|---|---|---|
| 8 | 60 | 4 | 0.5 |
| 8 | 70 | 10 | 0.5 |
| 8 | 80 | 6 | 0.5 |
| 8 | 90 | 11 | 0.364 |
| 8 | 100 | 5 | 0.6 |
| 9 | 20 | 9 | 0.444 |
| 9 | 30 | 15 | 0.4 |
| 9 | 40 | 10 | 0.7 |
| 9 | 50 | 13 | 0.385 |
| 9 | 60 | 9 | 0.444 |
| 9 | 70 | 6 | 0.333 |
| 9 | 80 | 4 | 0.25 |
| 10 | 10 | 7 | 0.429 |
| 10 | 20 | 15 | 0.4 |
| 10 | 30 | 19 | 0.316 |
| 10 | 40 | 12 | 0.333 |
| 10 | 50 | 6 | 0.333 |
| 10 | 60 | 9 | 0.444 |
| 10 | 70 | 2 | 0 |
| 10 | 80 | 8 | 0.25 |
| 10 | 90 | 7 | 0.286 |
| 10 | 100 | 3 | 0.333 |
| 11 | 10 | 7 | 0.429 |
| 11 | 20 | 8 | 0.375 |
| 11 | 30 | 15 | 0.533 |
| 11 | 40 | 15 | 0.467 |
| 11 | 50 | 16 | 0.438 |
| 11 | 60 | 7 | 0.286 |
| 11 | 70 | 6 | 0.5 |
| 11 | 80 | 4 | 0.25 |
| 12 | 10 | 13 | 0.385 |
| 12 | 20 | 9 | 0.556 |
| 12 | 30 | 13 | 0.231 |
| 12 | 40 | 12 | 0.5 |
| 12 | 50 | 9 | 0.444 |
| 12 | 60 | 5 | 0.4 |
| 12 | 70 | 7 | 0.429 |
| 12 | 80 | 3 | 0 |
| 12 | 90 | 4 | 0.25 |
| 12 | 100 | 2 | 0.5 |
| 13 | 20 | 1 | 1 |
| 13 | 30 | 4 | 0.5 |
| 13 | 40 | 10 | 0.5 |
| 13 | 50 | 7 | 0.714 |
| 13 | 60 | 9 | 0.333 |
| 13 | 70 | 8 | 0.125 |
| 13 | 80 | 9 | 0.667 |
| 13 | 90 | 7 | 0.571 |
| 13 | 100 | 11 | 0.545 |
| 13 | 110 | 11 | 0.273 |
| 13 | 120 | 1 | 1 |
| 14 | 20 | 1 | 0 |
| 14 | 30 | 7 | 0.571 |
| 14 | 40 | 8 | 0.25 |
| 14 | 50 | 8 | 0.5 |
| 14 | 60 | 9 | 0.556 |
| 14 | 70 | 6 | 0.333 |
| 14 | 80 | 8 | 0.5 |
| 14 | 90 | 7 | 0.429 |
| 14 | 100 | 6 | 0.5 |
| 14 | 110 | 2 | 0.5 |
| 15 | 30 | 5 | 0.2 |
| 15 | 40 | 5 | 0.6 |
| 15 | 50 | 3 | 1 |
| 15 | 60 | 6 | 0.333 |
| 15 | 70 | 5 | 0.4 |
| 15 | 80 | 5 | 0.4 |
| 15 | 90 | 7 | 0.286 |
| 15 | 100 | 5 | 0.4 |
| 15 | 110 | 1 | 0 |

TABLE C

Chromosome Bins, Hetero/Frequency at Chromosomes 02 and 03.
hetero 02 03 chr bin

| Chr | bins | freq | hetero02 | hetero03 |
|---|---|---|---|---|
|  |  | 1459 | 0.408 | 0.215 |
|  | 10 | 91 | 0.407 | 0 |
|  | 20 | 135 | 0.37 | 0.096 |
|  | 30 | 185 | 0.389 | 0.141 |
|  | 40 | 169 | 0.444 | 0.26 |
|  | 50 | 157 | 0.484 | 0.35 |
|  | 60 | 153 | 0.366 | 0.235 |
|  | 70 | 123 | 0.423 | 0.26 |
|  | 80 | 113 | 0.381 | 0.265 |
|  | 90 | 118 | 0.458 | 0.314 |
|  | 100 | 88 | 0.352 | 0.239 |
|  | 110 | 49 | 0.449 | 0.224 |
|  | 120 | 29 | 0.31 | 0.138 |
|  | 130 | 26 | 0.346 | 0.038 |
|  | 140 | 20 | 0.4 | 0.15 |
|  | 150 | 3 | 0.333 | 0 |
| 1 |  | 142 | 0.423 | 0.07 |
| 2 |  | 150 | 0.38 | 0.18 |
| 3 |  | 111 | 0.486 | 0.261 |
| 4 |  | 133 | 0.398 | 0.173 |
| 5 |  | 121 | 0.405 | 0.306 |
| 6 |  | 115 | 0.443 | 0.278 |
| 7 |  | 103 | 0.447 | 0.165 |
| 8 |  | 93 | 0.43 | 0.28 |
| 9 |  | 66 | 0.333 | 0.076 |
| 10 |  | 88 | 0.375 | 0.295 |
| 11 |  | 78 | 0.423 | 0.218 |
| 12 |  | 77 | 0.403 | 0.234 |
| 13 |  | 78 | 0.282 | 0.218 |
| 14 |  | 62 | 0.452 | 0.452 |
| 15 |  | 42 | 0.381 | 0.024 |
| 1 | 20 | 9 | 0.222 | 0 |
| 1 | 30 | 14 | 0.429 | 0 |
| 1 | 40 | 12 | 0.417 | 0 |
| 1 | 50 | 15 | 0.4 | 0 |
| 1 | 60 | 21 | 0.381 | 0 |
| 1 | 70 | 19 | 0.684 | 0 |
| 1 | 80 | 9 | 0.556 | 0.111 |
| 1 | 90 | 13 | 0.462 | 0.231 |
| 1 | 100 | 13 | 0.154 | 0.077 |
| 1 | 110 | 8 | 0.5 | 0.375 |
| 1 | 120 | 6 | 0.333 | 0.333 |
| 1 | 130 | 3 | 0.333 | 0 |
| 2 | 10 | 3 | 0.667 | 0 |
| 2 | 20 | 11 | 0.364 | 0.273 |
| 2 | 30 | 13 | 0.231 | 0.154 |
| 2 | 40 | 6 | 0.667 | 0.5 |
| 2 | 50 | 19 | 0.316 | 0.316 |
| 2 | 60 | 13 | 0.231 | 0.231 |
| 2 | 70 | 10 | 0.4 | 0.4 |
| 2 | 80 | 13 | 0.385 | 0.077 |
| 2 | 90 | 19 | 0.421 | 0.263 |
| 2 | 100 | 7 | 0.286 | 0 |
| 2 | 110 | 4 | 1 | 0 |
| 2 | 120 | 7 | 0.286 | 0 |
| 2 | 130 | 11 | 0.364 | 0 |
| 2 | 140 | 11 | 0.455 | 0 |
| 2 | 150 | 3 | 0.333 | 0 |
| 3 | 10 | 9 | 0.556 | 0 |
| 3 | 20 | 15 | 0.4 | 0 |
| 3 | 30 | 12 | 0.333 | 0 |
| 3 | 40 | 11 | 0.455 | 0.364 |
| 3 | 50 | 3 | 0 | 0 |
| 3 | 60 | 12 | 0.667 | 0.583 |
| 3 | 70 | 12 | 0.583 | 0.25 |
| 3 | 80 | 14 | 0.5 | 0.357 |
| 3 | 90 | 12 | 0.583 | 0.417 |
| 3 | 100 | 9 | 0.444 | 0.444 |
| 3 | 110 | 2 | 0.5 | 0.5 |
| 4 | 10 | 13 | 0.385 | 0 |
| 4 | 20 | 9 | 0.333 | 0.111 |
| 4 | 30 | 15 | 0.333 | 0.133 |
| 4 | 40 | 15 | 0.4 | 0.267 |
| 4 | 50 | 11 | 0.364 | 0.273 |

TABLE C-continued

Chromosome Bins, Hetero/
Frequency at Chromosomes 02 and 03.
hetero 02 03 chr bin

| Chr | bins | freq | hetero02 | hetero03 |
|---|---|---|---|---|
| 4 | 60 | 8 | 0.375 | 0.375 |
| 4 | 70 | 7 | 0.857 | 0.857 |
| 4 | 80 | 9 | 0.222 | 0.222 |
| 4 | 90 | 9 | 0.444 | 0 |
| 4 | 100 | 7 | 0.429 | 0 |
| 4 | 110 | 8 | 0.5 | 0 |
| 4 | 120 | 7 | 0.429 | 0 |
| 4 | 130 | 8 | 0.375 | 0 |
| 4 | 140 | 7 | 0.286 | 0.286 |
| 5 | 10 | 12 | 0.417 | 0 |
| 5 | 20 | 12 | 0.5 | 0.167 |
| 5 | 30 | 11 | 0.455 | 0.364 |
| 5 | 40 | 14 | 0.429 | 0.286 |
| 5 | 50 | 10 | 0.5 | 0.5 |
| 5 | 60 | 8 | 0.125 | 0.125 |
| 5 | 70 | 8 | 0.375 | 0.375 |
| 5 | 80 | 8 | 0.5 | 0.5 |
| 5 | 90 | 8 | 0.625 | 0.625 |
| 5 | 100 | 7 | 0.286 | 0.286 |
| 5 | 110 | 9 | 0.333 | 0.333 |
| 5 | 120 | 8 | 0.25 | 0.25 |
| 5 | 130 | 4 | 0.25 | 0.25 |
| 5 | 140 | 2 | 0.5 | 0.5 |
| 6 | 10 | 13 | 0.538 | 0 |
| 6 | 20 | 14 | 0.5 | 0 |
| 6 | 30 | 11 | 0.455 | 0 |
| 6 | 40 | 12 | 0.5 | 0.5 |
| 6 | 50 | 10 | 0.5 | 0.5 |
| 6 | 60 | 18 | 0.389 | 0.389 |
| 6 | 70 | 8 | 0.375 | 0.375 |
| 6 | 80 | 8 | 0.25 | 0.25 |
| 6 | 90 | 7 | 0.429 | 0.429 |
| 6 | 100 | 10 | 0.4 | 0.4 |
| 6 | 110 | 4 | 0.5 | 0.5 |
| 7 | 10 | 6 | 0.167 | 0 |
| 7 | 20 | 12 | 0.333 | 0 |
| 7 | 30 | 16 | 0.438 | 0.25 |
| 7 | 40 | 14 | 0.429 | 0.143 |
| 7 | 50 | 16 | 0.688 | 0.438 |
| 7 | 60 | 15 | 0.533 | 0.133 |
| 7 | 70 | 9 | 0.333 | 0 |
| 7 | 80 | 5 | 0.2 | 0 |
| 7 | 90 | 7 | 0.286 | 0 |
| 7 | 100 | 3 | 1 | 0.667 |
| 8 | 10 | 8 | 0.25 | 0 |
| 8 | 20 | 10 | 0.4 | 0.2 |
| 8 | 30 | 15 | 0.467 | 0.267 |
| 8 | 40 | 13 | 0.462 | 0.231 |
| 8 | 50 | 11 | 0.636 | 0.273 |
| 8 | 60 | 4 | 0.25 | 0.25 |
| 8 | 70 | 10 | 0.4 | 0.4 |
| 8 | 80 | 6 | 0.5 | 0.5 |
| 8 | 90 | 11 | 0.455 | 0.455 |
| 8 | 100 | 5 | 0.2 | 0.2 |
| 9 | 20 | 9 | 0.333 | 0 |
| 9 | 30 | 15 | 0.467 | 0 |
| 9 | 40 | 10 | 0.5 | 0 |
| 9 | 50 | 13 | 0.231 | 0.077 |
| 9 | 60 | −9 | 0.222 | 0.222 |
| 9 | 70 | 6 | 0.167 | 0.167 |
| 9 | 80 | 4 | 0.25 | 0.25 |
| 10 | 10 | 7 | 0.286 | 0 |
| 10 | 20 | 15 | 0.333 | 0.2 |
| 10 | 30 | 19 | 0.158 | 0.053 |
| 10 | 40 | 12 | 0.5 | 0.417 |
| 10 | 50 | 6 | 0.667 | 0.667 |
| 10 | 60 | 9 | 0.333 | 0.333 |
| 10 | 70 | 2 | 0.5 | 0.5 |
| 10 | 80 | 8 | 0.5 | 0.5 |
| 10 | 90 | 7 | 0.286 | 0.286 |
| 10 | 100 | 3 | 1 | 1 |
| 11 | 10 | 7 | 0.143 | 0 |
| 11 | 20 | 8 | 0.25 | 0.125 |
| 11 | 30 | 15 | 0.6 | 0.2 |
| 11 | 40 | 15 | 0.6 | 0.267 |
| 11 | 50 | 16 | 0.625 | 0.438 |
| 11 | 60 | 7 | 0.143 | 0.143 |
| 11 | 70 | 6 | 0 | 0 |
| 11 | 80 | 4 | 0.25 | 0.25 |
| 12 | 10 | 13 | 0.538 | 0 |
| 12 | 20 | 9 | 0.333 | 0 |
| 12 | 30 | 13 | 0.462 | 0.231 |
| 12 | 40 | 12 | 0.167 | 0.167 |
| 12 | 50 | 9 | 0.778 | 0.778 |
| 12 | 60 | 5 | 0.2 | 0.2 |
| 12 | 70 | 7 | 0.286 | 0.286 |
| 12 | 80 | 3 | 0.333 | 0.333 |
| 12 | 90 | 4 | 0.5 | 0.5 |
| 12 | 100 | 2 | 0 | 0 |
| 13 | 20 | 1 | 0 | 0 |
| 13 | 30 | 4 | 0.5 | 0.25 |
| 13 | 40 | 10 | 0.4 | 0.4 |
| 13 | 50 | 7 | 0.429 | 0.429 |
| 13 | 60 | 9 | 0 | 0 |
| 13 | 70 | 8 | 0.25 | 0.25 |
| 13 | 80 | 9 | 0.222 | 0.222 |
| 13 | 90 | 7 | 0.571 | 0.571 |
| 13 | 100 | 11 | 0.273 | 0.091 |
| 13 | 110 | 11 | 0.182 | 0 |
| 13 | 120 | 1 | 0 | 0 |
| 14 | 20 | 1 | 1 | 1 |
| 14 | 30 | 7 | 0.286 | 0.286 |
| 14 | 40 | 8 | 0.375 | 0.375 |
| 14 | 50 | 8 | 0.5 | 0.5 |
| 14 | 60 | 9 | 0.556 | 0.556 |
| 14 | 70 | 6 | 0.5 | 0.5 |
| 14 | 80 | 8 | 0.375 | 0.375 |
| 14 | 90 | 7 | 0.429 | 0.429 |
| 14 | 100 | 6 | 0.333 | 0.333 |
| 14 | 110 | 2 | 1 | 1 |
| 15 | 30 | 5 | 0.2 | 0 |
| 15 | 40 | 5 | 0.4 | 0 |
| 15 | 50 | 3 | 0.333 | 0 |
| 15 | 60 | 6 | 0.833 | 0 |
| 15 | 70 | 5 | 0 | 0 |
| 15 | 80 | 5 | 0.4 | 0 |
| 15 | 90 | 7 | 0.429 | 0 |
| 15 | 100 | 5 | 0.4 | 0.2 |
| 15 | 110 | 1 | 0 | 0 |

TABLE D

Chromosome Bins, Hetero/
Frequency at Chromosomes 12 and 04.
Hetero 12 04 chr bin

| chr | Bins | freq | hetero12 | hetero04 |
|---|---|---|---|---|
|  |  | 1459 | 0.367 | 0.214 |
|  | 10 | 91 | 0.418 | 0.066 |
|  | 20 | 135 | 0.311 | 0.081 |
|  | 30 | 185 | 0.384 | 0.2 |
|  | 40 | 169 | 0.355 | 0.314 |
|  | 50 | 157 | 0.357 | 0.35 |
|  | 60 | 153 | 0.346 | 0.209 |
|  | 70 | 123 | 0.358 | 0.163 |
|  | 80 | 113 | 0.292 | 0.195 |
|  | 90 | 118 | 0.398 | 0.254 |
|  | 100 | 88 | 0.477 | 0.273 |
|  | 110 | 49 | 0.388 | 0.224 |
|  | 120 | 29 | 0.241 | 0.172 |
|  | 130 | 26 | 0.385 | 0.192 |
|  | 140 | 20 | 0.6 | 0.05 |
|  | 150 | 3 | 0.667 | 0 |
| 1 | . | 142 | 0.366 | 0.324 |

TABLE D-continued

Chromosome Bins, Hetero/
Frequency at Chromosomes 12 and 04.
Hetero 12 04 chr bin

| chr | Bins | freq | hetero12 | hetero04 |
|---|---|---|---|---|
| 2 | 150 | 0.3 | 0.193 |  |
| 3 | 111 | 0.459 | 0.261 |  |
| 4 | 133 | 0.301 | 0.211 |  |
| 5 | 121 | 0.388 | 0.273 |  |
| 6 | 115 | 0.443 | 0.217 |  |
| 7 | 103 | 0.369 | 0.136 |  |
| 8 | 93 | 0.43 | 0.172 |  |
| 9 | 66 | 0.273 | 0.167 |  |
| 10 | 88 | 0.352 | 0.284 |  |
| 11 | 78 | 0.372 | 0.154 |  |
| 12 | 77 | 0.39 | 0.143 |  |
| 13 | 78 | 0.346 | 0.167 |  |
| 14 | 62 | 0.403 | 0.274 |  |
| 15 | 42 | 0.286 | 0.071 |  |
| 1 | 20 | 9 | 0.333 | 0.111 |
| 1 | 30 | 14 | 0.214 | 0.214 |
| 1 | 40 | 12 | 0.333 | 0.333 |
| 1 | 50 | 15 | 0.4 | 0.4 |
| 1 | 60 | 21 | 0.381 | 0.381 |
| 1 | 70 | 19 | 0.421 | 0.421 |
| 1 | 80 | 9 | 0.333 | 0.333 |
| 1 | 90 | 13 | 0.385 | 0.385 |
| 1 | 100 | 13 | 0.308 | 0.231 |
| 1 | 110 | 8 | 0.5 | 0.25 |
| 1 | 120 | 6 | 0.167 | 0 |
| 1 | 130 | 3 | 1 | 1 |
| 2 | 10 | 3 | 0.333J | 0 |
| 2 | 20 | 11 | 0.364 | 0.182 |
| 2 | 30 | 13 | 0.231 | 0.231 |
| 2 | 40 | 6 | 0.333 | 0.333 |
| 2 | 50 | 19 | 0.421 | 0.421 |
| 2 | 60 | 13 | 0.385 | 0.385 |
| 2 | 70 | 10 | 0.2 | 0.2 |
| 2 | 80 | 13 | 0.154 | 0.154 |
| 2 | 90 | 19 | 0.158 | 0.158 |
| 2 | 100 | 7 | 0 | 0 |
| 2 | 110 | 4 | 0.25 | 0.25 |
| 2 | 120 | 7 | 0.286 | 0.143 |
| 2 | 130 | 11 | 0.364 | 0 |
| 2 | 140 | 11 | 0.545 | 0 |
| 2 | 150 | 3 | 0.667 | 0 |
| 3 | 10 | 9 | 0.444 | 0 |
| 3 | 20 | 15 | 0.467 | 0.133 |
| 3 | 30 | 12 | 0.5 | 0.25 |
| 3 | 40 | 11 | 0.182 | 0 |
| 3 | 50 | 3 | 0 | 0 |
| 3 | 60 | 12 | 0.583 | 0.333 |
| 3 | 70 | 12 | 0.5 | 0.083 |
| 3 | 80 | 14 | 0.429 | 0.429 |
| 3 | 90 | 12 | 0.5 | 0.5 |
| 3 | 100 | 9 | 0.667 | 0.667 |
| 3 | 110 | 2 | 0.5 | 0.5 |
| 4 | 10 | 13 | 0.385 | 0.231 |
| 4 | 20 | 9 | 0.333 | 0.222 |
| 4 | 30 | 15 | 0.267 | 0.133 |
| 4 | 40 | 15 | 0.333 | 0.267 |
| 4 | 50 | 11 | 0.455 | 0.455 |
| 4 | 60 | 8 | 0.25 | 0.25 |
| 4 | 70 | 7 | 0 | 0 |
| 4 | 80 | 9 | 0.333 | 0.333 |
| 4 | 90 | 9 | 0.333 | 0.333 |
| 4 | 100 | 7 | 0.286 | 0.286 |
| 4 | 110 | 8 | 0.25 | 0.25 |
| 4 | 120 | 7 | 0 | 0 |
| 4 | 130 | 8 | 0.125 | 0 |
| 4 | 140 | 7 | 0.714 | 0 |
| 5 | 10 | 12 | 0.5 | 0.167 |
| 5 | 20 | 12 | 0.333 | 0.167 |
| 5 | 30 | 11 | 0.273 | 0.273 |
| 5 | 40 | 14 | 0.429 | 0.429 |
| 5 | 50 | 10 | 0.1 | 0.1 |
| 5 | 60 | 8 | 0.25 | 0.25 |
| 5 | 70 | 8 | 0.375 | 0.375 |
| 5 | 80 | 8 | 0.375 | 0.25 |
| 5 | 90 | 8 | 0.25 | 0 |
| 5 | 100 | 7 | 0.714 | 0 |
| 5 | 110 | 9 | 0.556 | 0.556 |
| 5 | 120 | 8 | 0.5 | 0.5 |
| 5 | 130 | 4 | 0.5 | 0.5 |
| 5 | 140 | 2 | 0.5 | 0.5 |
| 6 | 10 | 13 | 0.385 | 0 |
| 6 | 20 | 14 | 0.214 | 0 |
| 6 | 30 | 11 | 0.455 | 0.364 |
| 6 | 40 | 12 | 0.75 | 0.75 |
| 6 | 50 | 10 | 0.5 | 0.5 |
| 6 | 60 | 18 | 0.389 | 0.111 |
| 6 | 70 | 8 | 0.5 | 0 |
| 6 | 80 | 8 | 0.125 | 0 |
| 6 | 90 | 7 | 0.429 | 0.429 |
| 6 | 100 | 10 | 0.7 | 0.2 |
| 6 | 110 | 4 | 0.5 | 0 |
| 7 | 10 | 6 | 0.333 | 0 |
| 7 | 20 | 12 | 0.5 | 0 |
| 7 | 30 | 16 | 0.25 | 0 |
| 7 | 40 | 14 | 0.357 | 0.357 |
| 7 | 50 | 16 | 0.438 | 0.438 |
| 7 | 60 | 15 | 0.267 | 0 |
| 7 | 70 | 9 | 0.333 | 0 |
| 7 | 80 | 5 | 0.4 | 0 |
| 7 | 90 | 7 | 0.429 | 0 |
| 7 | 100 | 3 | 0.667 | 0.667 |
| 8 | 10 | 8 | 0.25 | 0 |
| 8 | 20 | 10 | 0.2 | 0 |
| 8 | 30 | 15 | 0.667 | 0 |
| 8 | 40 | 13 | 0.385 | 0.385 |
| 8 | 50 | 11 | 0.273 | 0.273 |
| 8 | 60 | 4 | 0.25 | 0.25 |
| 8 | 70 | 10 | 0.5 | 0.5 |
| 8 | 80 | 6 | 0.333 | 0.167 |
| 8 | 90 | 11 | 0.636 | 0 |
| 8 | 100 | 5 | 0.6 | 0.2 |
| 9 | 20 | 9 | 0.111 | 0 |
| 9 | 30 | 15 | 0.4 | 0.2 |
| 9 | 40 | 10 | 0.1 | 0.1 |
| 9 | 50 | 13 | 0.385 | 0.385 |
| 9 | 60 | 9 | 0.222 | 0.222 |
| 9 | 70 | 6 | 0.333 | 0 |
| 9 | 80 | 4 | 0.25 | 0 |
| 10 | 10 | 7 | 0.571 | 0.143 |
| 10 | 20 | 15 | 0.267 | 0.133 |
| 10 | 30 | 19 | 0.368 | 0.368 |
| 10 | 40 | 12 | 0.167 | 0.167 |
| 10 | 50 | 6 | 0.333 | 0.333 |
| 10 | 60 | 9 | 0.333 | 0.333 |
| 10 | 70 | 2 | 0.5 | 0.5 |
| 10 | 80 | 8 | 0.375 | 0.375 |
| 10 | 90 | 7 | 0.571 | 0.571 |
| 10 | 100 | 3 | 0.333 | 0 |
| 11 | 10 | 7 | 0.286 | 0 |
| 11 | 20 | 8 | 0.375 | 0 |
| 11 | 30 | 15 | 0.4 | 0.2 |
| 11 | 40 | 15 | 0.467 | 0.2 |
| 11 | 50 | 16 | 0.313 | 0.313 |
| 11 | 60 | 7 | 0.143 | 0.143 |
| 11 | 70 | 6 | 0.5 | 0 |
| 11 | 80 | 4 | 0.5 | 0 |
| 12 | 10 | 13 | 0.538 | 0 |
| 12 | 20 | 9 | 0.222 | 0 |
| 12 | 30 | 13 | 0.462 | 0.077 |
| 12 | 40 | 12 | 0.333 | 0.333 |
| 12 | 50 | 9 | 0.444 | 0.444 |
| 12 | 60 | 5 | 0.2 | 0.2 |
| 12 | 70 | 7 | 0 | 0 |
| 12 | 80 | 3 | 0.333 | 0.333 |
| 12 | 90 | 4 | 0.75 | 0 |
| 12 | 100 | 2 | 1 | 0 |
| 13 | 20 | 1 | 0 | 0 |
| 13 | 30 | 4 | 0.5 | 0.5 |

TABLE D-continued

Chromosome Bins, Hetero/Frequency at Chromosomes 12 and 04.
Hetero 12 04 chr bin

| chr | Bins | freq | hetero12 | hetero04 |
|---|---|---|---|---|
| 13 | 40 | 10 | 0.2 | 0.2 |
| 13 | 50 | 7 | 0.286 | 0.143 |
| 13 | 60 | 9 | 0.444 | 0 |
| 13 | 70 | 8 | 0.5 | 0 |
| 13 | 80 | 9 | 0.111 | 0.111 |
| 13 | 90 | 7 | 0.429 | 0.429 |
| 13 | 100 | 11 | 0.455 | 0.364 |
| 13 | 110 | 11 | 0.364 | 0 |
| 13 | 120 | 1 | 0 | 0 |
| 14 | 20 | 1 | 0 | 0 |
| 14 | 30 | 7 | 0.714 | 0.429 |
| 14 | 40 | 8 | 0.625 | 0.625 |
| 14 | 50 | 8 | 0.375 | 0.375 |
| 14 | 60 | 9 | 0.333 | 0.111 |
| 14 | 70 | 6 | 0.333 | 0 |
| 14 | 80 | 8 | 0.125 | 0 |
| 14 | 90 | 7 | 0.286 | 0.286 |
| 14 | 100 | 6 | 0.667 | 0.5 |
| 14 | 110 | 2 | 0 | 0 |
| 15 | 30 | 5 | 0.2 | 0 |
| 15 | 40 | 5 | 0.2 | 0.2 |
| 15 | 50 | 3 | 0 | 0 |
| 15 | 60 | 6 | 0.5 | 0 |
| 15 | 70 | 5 | 0.2 | 0 |
| 15 | 80 | 5 | 0.4 | 0 |
| 15 | 90 | 7 | 0.429 | 0.143 |
| 15 | 100 | 5 | 0.2 | 0.2 |
| 15 | 110 | 1 | 0 | 0 |

TABLE E

Chromosome Bins, Hetero/Frequency at Chromosomes 12 and 05.
hetero 12 05 chr bin

| Chr | bins | freq | hetero12 | hetero05 |
|---|---|---|---|---|
|  |  | 1459 | 0.367 | 0.214 |
|  | 10 | 91 | 0.418 | 0.066 |
|  | 20 | 135 | 0.311 | 0.081 |
|  | 30 | 185 | 0.384 | 0.2 |
|  | 40 | 169 | 0.355 | 0.314 |
|  | 50 | 157 | 0.357 | 0.35 |
|  | 60 | 153 | 0.346 | 0.209 |
|  | 70 | 123 | 0.358 | 0.163 |
|  | 80 | 113 | 0.292 | 0.195 |
|  | 90 | 118 | 0.398 | 0.254 |
|  | 100 | 88 | 0.477 | 0.273 |
|  | 110 | 49 | 0.388 | 0.224 |
|  | 120 | 29 | 0.241 | 0.172 |
|  | 130 | 26 | 0.385 | 0.192 |
|  | 140 | 20 | 0.6 | 0.05 |
|  | 150 | 3 | 0.667 | 0 |
| 1 |  | 142 | 0.366 | 0.324 |
| 2 |  | 150 | 0.3 | 0.193 |
| 3 |  | 111 | 0.459 | 0.261 |
| 4 |  | 133 | 0.301 | 0.211 |
| 5 |  | 121 | 0.388 | 0.273 |
| 6 |  | 115 | 0.443 | 0.217 |
| 7 |  | 103 | 0.369 | 0.136 |
| 8 |  | 93 | 0.43 | 0.172 |
| 9 |  | 66 | 0.273 | 0.167 |
| 10 |  | 88 | 0.352 | 0.284 |
| 11 |  | 78 | 0.372 | 0.154 |
| 12 |  | 77 | 0.39 | 0.143 |
| 13 |  | 78 | 0.346 | 0.167 |
| 14 |  | 62 | 0.403 | 0.274 |
| 15 |  | 42 | 0.286 | 0.071 |
| 1 | 20 | 9 | 0.333 | 0.111 |
| 1 | 30 | 14 | 0.214 | 0.214 |
| 1 | 40 | 12 | 0.333 | 0.333 |
| 1 | 50 | 15 | 0.4 | 0.4 |
| 1 | 60 | 21 | 0.381 | 0.381 |
| 1 | 70 | 19 | 0.421 | 0.421 |
| 1 | 80 | 9 | 0.333 | 0.333 |
| 1 | 90 | 13 | 0.385 | 0.385 |
| 1 | 100 | 13 | 0.308 | 0.231 |
| 1 | 110 | 8 | 0.5 | 0.25 |
| 1 | 120 | 6 | 0.167 | 0 |
| 1 | 130 | 3 | 1 | 1 |
| 2 | 10 | 3 | 0.333 | 0 |
| 2 | 20 | 11 | 0.364 | 0.182 |
| 2 | 30 | 13 | 0.231 | 0.231 |
| 2 | 40 | 6 | 0.333 | 0.333 |
| 2 | 50 | 19 | 0.421 | 0.421 |
| 2 | 60 | 13 | 0.385 | 0.385 |
| 2 | 70 | 10 | 0.2 | 0.2 |
| 2 | 80 | 13 | 0.154 | 0.154 |
| 2 | 90 | 19 | 0.158 | 0.158 |
| 2 | 100 | 7 | 0 | 0 |
| 2 | 110 | 4 | 0.25 | 0.25 |
| 2 | 120 | 7 | 0.286 | 0.143 |
| 2 | 130 | 11 | 0.364 | 0 |
| 2 | 140 | 11 | 0.545 | 0 |
| 2 | 150 | 3 | 0.667 | 0 |
| 3 | 10 | 9 | 0.444 | 0 |
| 3 | 20 | 15 | 0.467 | 0.133 |
| 3 | 30 | 12 | 0.5 | 0.25 |
| 3 | 40 | 11 | 0.182 | 0 |
| 3 | 50 | 3 | 0 | 0 |
| 3 | 60 | 12 | 0.583 | 0.333 |
| 3 | 70 | 12 | 0.5 | 0.083 |
| 3 | 80 | 14 | 0.429 | 0.429 |
| 3 | 90 | 12 | 0.5 | 0.5 |
| 3 | 100 | 9 | 0.667 | 0.667 |
| 3 | 110 | 2 | 0.5 | 0.5 |
| 4 | 10 | 13 | 0.385 | 0.231 |
| 4 | 20 | 9 | 0.333 | 0.222 |
| 4 | 30 | 15 | 0.267 | 0.133 |
| 4 | 40 | 15 | 0.333 | 0.267 |
| 4 | 50 | 11 | 0.455 | 0.455 |
| 4 | 60 | 8 | 0.25 | 0.25 |
| 4 | 70 | 7 | 0 | 0 |
| 4 | 80 | 9 | 0.333 | 0.333 |
| 4 | 90 | 9 | 0.333 | 0.333 |
| 4 | 100 | 7 | 0.286 | 0.286 |
| 4 | 110 | 8 | 0.25 | 0.25 |
| 4 | 120 | 7 | 0 | 0 |
| 4 | 130 | 8 | 0.125 | 0 |
| 4 | 140 | 7 | 0.714 | 0 |
| 5 | 10 | 12 | 0.5 | 0.167 |
| 5 | 20 | 12 | 0.333 | 0.167 |
| 5 | 30 | 11 | 0.273 | 0.273 |
| 5 | 40 | 14 | 0.429 | 0.429 |
| 5 | 50 | 10 | 0.1 | 0.1 |
| 5 | 60 | 8 | 0.25 | 0.25 |
| 5 | 70 | 8 | 0.375 | 0.375 |
| 5 | 80 | 8 | 0.375 | 0.25 |
| 5 | 90 | 8 | 0.25 | 0 |
| 5 | 100 | 7 | 0.714 | 0 |
| 5 | 110 | 9 | 0.556 | 0.556 |
| 5 | 120 | 8 | 0.5 | 0.5 |
| 5 | 130 | 4 | 0.5 | 0.5 |
| 5 | 140 | 2 | 0.5 | 0.5 |
| 6 | 10 | 13 | 0.385 | 0 |
| 6 | 20 | 14 | 0.214 | .0 |
| 6 | 30 | 11 | 0.455 | 0.364 |
| 6 | 40 | 12 | 0.75 | 0.75 |
| 6 | 50 | 10 | 0.5 | 0.5 |
| 6 | 60 | 18 | 0.389 | 0.111 |
| 6 | 70 | 8 | 0.5 | 0 |
| 6 | 80 | 8 | 0.125 | 0 |
| 6 | 90 | 7 | 0.429 | 0.429 |
| 6 | 100 | 10 | 0.7 | 0.2 |
| 6 | 110 | 4 | 0.5 | 0 |

TABLE E-continued

Chromosome Bins, Hetero/
Frequency at Chromosomes 12 and 05.
hetero 12 05 chr bin

| Chr | bins | freq | hetero12 | hetero05 |
|---|---|---|---|---|
| 7 | 10 | 6 | 0.333 | 0 |
| 7 | 20 | 12 | 0.5 | 0 |
| 7 | 30 | 16 | 0.25 | 0 |
| 7 | 40 | 14 | 0.357 | 0.357 |
| 7 | 50 | 16 | 0.438 | 0.438 |
| 7 | 60 | 15 | 0.267 | 0 |
| 7 | 70 | 9 | 0.333 | 0 |
| 7 | 80 | 5 | 0.4 | 0 |
| 7 | 90 | 7 | 0.429 | 0 |
| 7 | 100 | 3 | 0.667 | 0.667 |
| 8 | 10 | 8 | 0.25 | 0 |
| 8 | 20 | 10 | 0.2 | 0 |
| 8 | 30 | 15 | 0.667 | 0 |
| 8 | 40 | 13 | 0.385 | 0.385 |
| 8 | 50 | 11 | 0.273 | 0.273 |
| 8 | 60 | 4 | 0.25 | 0.25 |
| 8 | 70 | 10 | 0.5 | 0.5 |
| 8 | 80 | 6 | 0.333 | 0.167 |
| 8 | 90 | 11 | 0.636 | 0 |
| 8 | 100 | 5 | 0.6 | 0.2 |
| 9 | 20 | 9 | 0.111 | 0 |
| 9 | 30 | 15 | 0.4 | 0.2 |
| 9 | 40 | 10 | 0.1 | 0.1 |
| 9 | 50 | 13 | 0.385 | 0.385 |
| 9 | 60 | 9 | 0.222 | 0.222 |
| 9 | 70 | 6 | 0.333 | 0 |
| 9 | 80 | 4 | 0.25 | 0 |
| 10 | 10 | 7 | 0.571 | 0.143 |
| 10 | 20 | 15 | 0.267 | 0.133 |
| 10 | 30 | 19 | 0.368 | 0.368 |
| 10 | 40 | 12 | 0.167 | 0.167 |
| 10 | 50 | 6 | 0.333 | 0.333 |
| 10 | 60 | 9 | 0.333 | 0.333 |
| 10 | 70 | 2 | 0.5 | 0.5 |
| 10 | 80 | 8 | 0.375 | 0.375 |
| 10 | 90 | 7 | 0.571 | 0.571 |
| 10 | 100 | 3 | 0.333 | 0 |
| 11 | 10 | 7 | 0.286 | 0 |
| 11 | 20 | 8 | 0.375 | 0 |
| 11 | 30 | 15 | 0.4 | 0.2 |
| 11 | 40 | 15 | 0.467 | 0.2 |
| 11 | 50 | 16 | 0.313 | 0.313 |
| 11 | 60 | 7 | 0.143 | 0.143 |
| 11 | 70 | 6 | 0.5 | 0 |
| 11 | 80 | 4 | 0.5 | 0 |
| 12 | 10 | 13 | 0.538 | 0 |
| 12 | 20 | 9 | 0.222 | 0 |
| 12 | 30 | 13 | 0.462 | 0.077 |
| 12 | 40 | 12 | 0.333 | 0.333 |
| 12 | 50 | 9 | 0.444 | 0.444 |
| 12 | 60 | 5 | 0.2 | 0.2 |
| 12 | 70 | 7 | 0 | 0 |
| 12 | 80 | 3 | 0.333 | 0.333 |
| 12 | 90 | 4 | 0.75 | 0 |
| 12 | 100 | 2 | 1 | 0 |
| 13 | 20 | 1 | 0 | 0 |
| 13 | 30 | 4 | 0.5 | 0.5 |
| 13 | 40 | 10 | 0.2 | 0.2 |
| 13 | 50 | 7 | 0.286 | 0.143 |
| 13 | 60 | 9 | 0.444 | 0 |
| 13 | 70 | 8 | 0.5 | 0 |
| 13 | 80 | 9 | 0.111 | 0.111 |
| 13 | 90 | 7 | 0.429 | 0.429 |
| 13 | 100 | 11 | 0.455 | 0.364 |
| 13 | 110 | 11 | 0.364 | 0 |
| 13 | 120 | 1 | 0 | 0 |
| 14 | 20 | 1 | 0 | 0 |
| 14 | 30 | 7 | 0.714 | 0.429 |
| 14 | 40 | 8 | 0.625 | 0.625 |
| 14 | 50 | 8 | 0.375 | 0.375 |
| 14 | 60 | 9 | 0.333 | 0.111 |
| 14 | 70 | 6 | 0.333 | 0 |
| 14 | 80 | 8 | 0.125 | 0 |
| 14 | 90 | 7 | 0.286 | 0.286 |
| 14 | 100 | 6 | 0.667 | 0.5 |
| 14 | 110 | 2 | 0 | 0 |
| 15 | 30 | 5 | 0.2 | 0 |
| 15 | 40 | 5 | 0.2 | 0.2 |
| 15 | 50 | 3 | 0 | 0 |
| 15 | 60 | 6 | 0.5 | 0 |
| 15 | 70 | 5 | 0.2 | 0 |
| 15 | 80 | 5 | 0.4 | 0 |
| 15 | 90 | 7 | 0.429 | 0.143 |
| 15 | 100 | 5 | 0.2 | 0.2 |
| 15 | 110 | 1 | 0 | 0 |

TABLE F

Chromosome Bins, Hetero/
Frequency at Chromosomes 11 and 16.
Hetero 11 06 chr bin

| Chr | bins | freq | hetero11 | hetero06 |
|---|---|---|---|---|
|  |  | 1459 | 0.326 | 0.213 |
|  | 10 | 91 | 0.33 | 0.077 |
|  | 20 | 135 | 0.319 | 0.096 |
|  | 30 | 185 | 0.346 | 0.2 |
|  | 40 | 169 | 0.367 | 0.243 |
|  | 50 | 157 | 0.344 | 0.223 |
|  | 60 | 153 | 0.294 | 0.222 |
|  | 70 | 123 | 0.276 | 0.252 |
|  | 80 | 113 | 0.345 | 0.292 |
|  | 90 | 118 | 0.254 | 0.212 |
|  | 100 | 88 | 0.33 | 0.193 |
|  | 110 | 49 | 0.327 | 0.245 |
|  | 120 | 29 | 0.345 | 0.345 |
|  | 130 | 26 | 0.423 | 0.346 |
|  | 140 | 20 | 0.4 | 0.35 |
|  | 150 | 3 | 0 | 0 |
| 1 |  | 142 | 0.317 | 0.197 |
| 2 |  | 150 | 0.273 | 0.207 |
| 3 |  | 111 | 0.288 | 0.234 |
| 4 |  | 133 | 0.338 | 0.173 |
| 5 |  | 121 | 0.355 | 0.331 |
| 6 |  | 115 | 0.252 | 0.096 |
| 7 |  | 103 | 0.34 | 0.204 |
| 8 |  | 93 | 0.344 | 0.204 |
| 9 |  | 66 | 0.318 | 0.167 |
| 10 |  | 88 | 0.432 | 0.307 |
| 11 |  | 78 | 0.372 | 0:167 |
| 12 |  | 77 | 0.39 | 0.169 |
| 13 |  | 78 | 0.244 | 0.154 |
| 14 |  | 62 | 0.323 | 0.323 |
| 15 | , | 42 | 0.381 | 0.381 |
| 1 | 20 | 9 | 0.333 | 0 |
| 1 | 30 | 14 | 0.429 | 0.286 |
| 1 | 40 | 12 | 0.333 | 0.167 |
| 1 | 50 | 15 | 0.333 | 0.267 |
| 1 | 60 | 21 | 0.286 | 0.286 |
| 1 | 70 | 19 | 0.211 | 0.211 |
| 1 | 80 | 9 | 0.222 | 0.111 |
| 1 | 90 | 13 | 0.231 | 0 |
| 1 | 100 | 13 | 0.462 | 0.308 |
| 1 | 110 | 8 | 0.25 | 0.125 |
| 1 | 120 | 6 | 0.333 | 0.333 |
| 1 | 130 | 3 | 0.667 | 0 |
| 2 | 10 | 3 | 0 | 0 |
| 2 | 20 | 11 | 0.455 | 0 |
| 2 | 30 | 13 | 0.308 | 0 |
| 2 | 40 | 6 | 0 | 0 |
| 2 | 50 | 19 | 0.211 | 0.211 |
| 2 | 60 | 13 | 0.462 | 0.462 |
| 2 | 70 | 10 | 0.2 | 0.2 |
| 2 | 80 | 13 | 0.231 | 0.231 |

TABLE F-continued

Chromosome Bins, Hetero/
Frequency at Chromosomes 11 and 16.
Hetero 11 06 chr bin

| Chr | bins | freq | hetero11 | hetero06 |
|---|---|---|---|---|
| 2 | 90 | 19 | 0.368 | 0.316 |
| 2 | 100 | 7 | 0 | 0 |
| 2 | 110 | 4 | 0.25 | 0.25 |
| 2 | 120 | 7 | 0.143 | 0.143 |
| 2 | 130 | 11 | 0.364 | 0.364 |
| 2 | 140 | 11 | 0.364 | 0.364 |
| 2 | 150 | 3 | 0 | 0 |
| 3 | 10 | 9 | 0.333 | 0 |
| 3 | 20 | 15 | 0.067 | 0 |
| 3 | 30 | 12 | 0.25 | 0.083 |
| 3 | 40 | 11 | 0.545 | 0.545 |
| 3 | 50 | 3 | 0.333 | 0.333 |
| 3 | 60 | 12 | 0.167 | 0.167 |
| 3 | 70 | 12 | 0.333 | 0.333 |
| 3 | 80 | 14 | 0.5 | 0.5 |
| 3 | 90 | 12 | 0.167 | 0.167 |
| 3 | 100 | 9 | 0.333 | 0.333 |
| 3 | 110 | 2 | 0 | 0 |
| 4 | 10 | 13 | 0.308 | 0.154 |
| 4 | 20 | 9 | 0.222 | 0.111 |
| 4 | 30 | 15 | 0.333 | 0.267 |
| 4 | 40 | 15 | 0.467 | 0.2 |
| 4 | 50 | 11 | 0.273 | 0 |
| 4 | 60 | 8 | 0.5 | 0 |
| 4 | 70 | 7 | 0.286 | 0 |
| 4 | 80 | 9 | 0.333 | 0 |
| 4 | 90 | 9 | 0.111 | 0 |
| 4 | 100 | 7 | 0.286 | 0.286 |
| 4 | 110 | 8 | 0.25 | 0.25 |
| 4 | 120 | 7 | 0.429 | 0.429 |
| 4 | 130 | 8 | 0.5 | 0.5 |
| 4 | 140 | 7 | 0.429 | 0.286 |
| 5 | 10 | 12 | 0.333 | 0.083 |
| 5 | 20 | 12 | 0.083 | 0.083 |
| 5 | 30 | 11 | 0.455 | 0.455 |
| 5 | 40 | 14 | 0.286 | 0.286 |
| 5 | 50 | 10 | 0.5 | 0.5 |
| 5 | 60 | 8 | 0.125 | 0.125 |
| 5 | 70 | 8 | 0.375 | 0.375 |
| 5 | 80 | 8 | 0.375 | 0.375 |
| 5 | 90 | 8 | 0.125 | 0.125 |
| 5 | 100 | 7 | 0.571 | 0.571 |
| 5 | 110 | 9 | 0.667 | 0.667 |
| 5 | 120 | 8 | 0.5 | 0.5 |
| 5 | 130 | 4 | 0.25 | 0.25 |
| 5 | 140 | 2 | 0.5 | 0.5 |
| 6 | 10 | 13 | 0.231 | 0 |
| 6 | 20 | 14 | 0.143 | 0.143 |
| 6 | 30 | 11 | 0.182 | 0.091 |
| 6 | 40 | 12 | 0.333 | 0.167 |
| 6 | 50 | 10 | 0.3 | 0.1 |
| 6 | 60 | 18 | 0.333 | 0.056 |
| 6 | 70 | 8 | 0.125 | 0.125 |
| 6 | 80 | 8 | 0.25 | 0.25 |
| 6 | 90 | 7 | 0.143 | 0.143 |
| 6 | 100 | 10 | 0.4 | 0 |
| 6 | 110 | 4 | 0.25 | 0 |
| 7 | 10 | 6 | 0.167 | 0 |
| 7 | 20 | 12 | 0.25 | 0 |
| 7 | 30 | 16 | 0.25 | 0.063 |
| 7 | 40 | 14 | 0.357 | 0.286 |
| 7 | 50 | 16 | 0.563 | 0.313 |
| 7 | 60 | 15 | 0.333 | 0.2 |
| 7 | 70 | 9 | 0.444 | 0.444 |
| 7 | 80 | 5 | 0.4 | 0.4 |
| 7 | 90 | 7 | 0.143 | 0.143 |
| 7 | 100 | 3 | 0.333 | 0.333 |
| 8 | 10 | 8 | 0.5 | 0 |
| 8 | 20 | 10 | 0.7 | 0.1 |
| 8 | 30 | 15 | 0.333 | 0.333 |
| 8 | 40 | 13 | 0.231 | 0.231 |
| 8 | 50 | 11 | 0.182 | 0.182 |
| 8 | 60 | 4 | 0 | 0 |
| 8 | 70 | 10 | 0.4 | 0.4 |
| 8 | 80 | 6 | 0.167 | 0.167 |
| 8 | 90 | 11 | 0.273 | 0.273 |
| 8 | 100 | 5 | 0.6 | 0 |
| 9 | 20 | 9 | 0.222 | 0 |
| 9 | 30 | 15 | 0.4 | 0.067 |
| 9 | 40 | 10 | 0.6 | 0.3 |
| 9 | 50 | 13 | 0.077 | 0.077 |
| 9 | 60 | 9 | 0.333 | 0.333 |
| 9 | 70 | 6 | 0.333 | 0.333 |
| 9 | 80 | 4 | 0.25 | 0.25 |
| 10 | 10 | 7 | 0.571 | 0.571 |
| 10 | 20 | 15 | 0.6 | 0.267 |
| 10 | 30 | 19 | 0.368 | 0.316 |
| 10 | 40 | 12 | 0.417 | 0.25 |
| 10 | 50 | 6 | 0.833 | 0.333 |
| 10 | 60 | 9 | 0.444 | 0.444 |
| 10 | 70 | 2 | 0 | 0 |
| 10 | 80 | 8 | 0.375 | 0.375 |
| 10 | 90 | 7 | 0 | 0 |
| 10 | 100 | 3 | 0.333 | 0.333 |
| 11 | 10 | 7 | 0.429 | 0 |
| 11 | 20 | 8 | 0.625 | 0.125 |
| 11 | 30 | 15 | 0.467 | 0.267 |
| 11 | 40 | 15 | 0.267 | 0.2 |
| 11 | 50 | 16 | 0.375 | 0.25 |
| 11 | 60 | 7 | 0 | 0 |
| 11 | 70 | 6 | 0.333 | 0.167 |
| 11 | 80 | 4 | 0.5 | 0 |
| 12 | 10 | 13 | 0.308 | 0 |
| 12 | 20 | 9 | 0.333 | 0.333 |
| 12 | 30 | 13 | 0.462 | 0.154 |
| 12 | 40 | 12 | 0.583 | 0.083 |
| 12 | 50 | 9 | 0.333 | 0 |
| 12 | 60 | 5 | 0.2 | 0.2 |
| 12 | 70 | 7 | 0.286 | 0.286 |
| 12 | 80 | 3 | 0.333 | 0.333 |
| 12 | 90 | 4 | 0.75 | 0.75 |
| 12 | 100 | 2 | 0 | 0 |
| 13 | 20 | 1 | 0 | 0 |
| 13 | 30 | 4 | 0.25 | 0 |
| 13 | 40 | 10 | 0 | 0 |
| 13 | 50 | 7 | 0.429 | 0.286 |
| 13 | 60 | 9 | 0.111 | 0.111 |
| 13 | 70 | 8 | 0.25 | 0.25 |
| 13 | 80 | 9 | 0.444 | 0.444 |
| 13 | 90 | 7 | 0.429 | 0.429 |
| 13 | 100 | 11 | 0.273 | 0 |
| 13 | 110 | 11 | 0.182 | 0 |
| 13 | 120 | 1 | 0 | 0 |
| 14 | 20 | 1 | 0 | 0 |
| 14 | 30 | 7 | 0.143 | 0.143 |
| 14 | 40 | 8 | 0.625 | 0.625 |
| 14 | 50 | 8 | 0.375 | 0.375 |
| 14 | 60 | 9 | 0.444 | 0.444 |
| 14 | 70 | 6 | 0.167 | 0.167 |
| 14 | 80 | 8 | 0.25 | 0.25 |
| 14 | 90 | 7 | 0.143 | 0.143 |
| 14 | 100 | 6 | 0.167 | 0.167 |
| 14 | 110 | 2 | 1 | 1 |
| 15 | 30 | 5 | 0.4 | 0.4 |
| 15 | 40 | 5 | 0.4 | 0.4 |
| 15 | 50 | 3 | 0.333 | 0.333 |
| 15 | 60 | 6 | 0.333 | 0.333 |
| 15 | 70 | 5 | 0.2 | 0.2 |
| 15 | 80 | 5 | 0.6 | 0.6 |
| 15 | 90 | 7 | 0.571 | 0.571 |
| 15 | 100 | 5 | 0.2 | 0.2 |
| 15 | 110 | 1 | 0 | 0 |

TABLE G

Chromosome Bins, Hetero/
Frequency at Chromosomes 11 and 07.
Hetero 11 07 chr bin

| chr | bins | Freq | hetero11 | hetero07 |
|---|---|---|---|---|
|  |  | 1459 | 0.326 | 0.168 |
|  | 10 | 91 | 0.33 | 0.033 |
|  | 20 | 135 | 0.319 | 0.081 |
|  | 30 | 185 | 0.346 | 0.092 |
|  | 40 | 169 | 0.367 | 0.16 |
|  | 50 | 157 | 0.344 | 0.185 |
|  | 60 | 153 | 0.294 | 0.176 |
|  | 70 | 123 | 0.276 | 0.154 |
|  | 80 | 113 | 0.345 | 0.274 |
|  | 90 | 118 | 0.254 | 0.186 |
|  | 100 | 88 | 0.33 | 0.239 |
|  | 110 | 49 | 0.327 | 0.265 |
|  | 120 | 29 | 0.345 | 0.276 |
|  | 130 | 26 | 0.423 | 0.346 |
|  | 140 | 20 | 0.4 | 0.4 |
|  | 150 | 3 | 0 | 0 |
| 1 |  | 142 | 0.317 | 0.085 |
| 2 |  | 150 | 0.273 | 0.093 |
| 3 |  | 111 | 0.288 | 0.189 |
| 4 |  | 133 | 0.338 | 0.12 |
| 5 |  | 121 | 0.355 | 0.215 |
| 6 |  | 115 | 0.252 | 0.217 |
| 7 |  | 103 | 0.34 | 0.282 |
| 8 |  | 93 | 0.344 | 0.097 |
| 9 |  | 66 | 0.318 | 0.061 |
| 10 |  | 88 | 0.432 | 0.239 |
| 11 |  | 78 | 0.372 | 0.218 |
| 12 |  | 77 | 0.39 | 0.091 |
| 13 |  | 78 | 0.244 | 0.154 |
| 14 |  | 62 | 0.323 | 0.258 |
| 15 |  | 42 | 0.381 | 0.381 |
| 1 | 20 | 9 | 0.333 | 0 |
| 1 | 30 | 14 | 0.429 | 0 |
| 1 | 40 | 12 | 0.333 | 0 |
| 1 | 50 | 15 | 0.333 | 0 |
| 1 | 60 | 21 | 0.286 | 0 |
| 1 | 70 | 19 | 0.211 | 0.053 |
| 1 | 80 | 9 | 0.222 | 0.111 |
| 1 | 90 | 13 | 0.231 | 0.231 |
| 1 | 100 | 13 | 0.462 | 0.154 |
| 1 | 110 | 8 | 0.25 | 0.25 |
| 1 | 120 | 6 | 0.333 | 0.167 |
| 1 | 130 | 3 | 0.667 | 0.667 |
| 2 | 10 | 3 | 0 | 0 |
| 2 | 20 | 11 | 0.455 | 0 |
| 2 | 30 | 13 | 0.308 | 0 |
| 2 | 40 | 6 | 0 | 0 |
| 2 | 50 | 19 | 0.211 | 0. |
| 2 | 60 | 13 | 0.462 | 0.231 |
| 2 | 70 | 10 | 0.2 | 0 |
| 2 | 80 | 13 | 0.231 | 0.154 |
| 2 | 90 | 19 | 0.368 | 0.158 |
| 2 | 100 | 7 | 0 | 0 |
| 2 | 110 | 4 | 0.25 | 0 |
| 2 | 120 | 7 | 0.143 | 0 |
| 2 | 130 | 11 | 0.364 | 0.182 |
| 2 | 140 | 11 | 0.364 | 0.364 |
| 2 | 150 | 3 | 0 | 0 |
| 3 | 10 | 9 | 0.333 | 0.111 |
| 3 | 20 | 15 | 0.067 | 0 |
| 3 | 30 | 12 | 0.25 | 0.083 |
| 3 | 40 | 11 | 0.545 | 0.364 |
| 3 | 50 | 3 | 0.333 | 0.333 |
| 3 | 60 | 12 | 0.167 | 0.167 |
| 3 | 70 | 12 | 0.333 | 0.333 |
| 3 | 80 | 14 | 0.5 | 0.357 |
| 3 | 90 | 12 | 0.167 | 0 |
| 3 | 100 | 9 | 0.333 | 0.333 |
| 3 | 110 | 2 | 0 | 0 |
| 4 | 10 | 13 | 0.308 | 0 |
| 4 | 20 | 9 | 0.222 | 0 |
| 4 | 30 | 15 | 0.333 | 0 |
| 4 | 40 | 15 | 0.467 | 0.067 |
| 4 | 50 | 11 | 0.273 | 0 |
| 4 | 60 | 8 | 0.5 | 0 |
| 4 | 70 | 7 | 0.286 | 0 |
| 4 | 80 | 9 | 0.333 | 0 |
| 4 | 90 | 9 | 0.111 | 0.111 |
| 4 | 100 | 7 | 0.286 | 0.286 |
| 4 | 110 | 8 | 0.25 | 0.25 |
| 4 | 120 | 7 | 0.429 | 0.429 |
| 4 | 130 | 8 | 0.5 | 0.5 |
| 4 | 140 | 7 | 0.429 | 0.429 |
| 5 | 10 | 12 | 0.333 | 0 |
| 5 | 20 | 12 | 0.083 | 0 |
| 5 | 30 | 11 | 0.455 | 0 |
| 5 | 40 | 14 | 0.286 | 0.071 |
| 5 | 50 | 10 | 0.5 | 0.3 |
| 5 | 60 | 8 | 0.125 | 0 |
| 5 | 70 | 8 | 0.375 | 0.25 |
| 5 | 80 | 8 | 0.375 | 0.375 |
| 5 | 90 | 8 | 0.125 | 0.125 |
| 5 | 100 | 7 | 0.571 | 0.571 |
| 5 | 110 | 9 | 0.667 | 0.667 |
| 5 | 120 | 8 | 0.5 | 0.5 |
| 5 | 130 | 4 | 0.25 | 0.25 |
| 5 | 140 | 2 | 0.5 | 0.5 |
| 6 | 10 | 13 | 0.231 | 0 |
| 6 | 20 | 14 | 0.143 | 0.143 |
| 6 | 30 | 11 | 0.182 | 0.091 |
| 6 | 40 | 12 | 0.333 | 0.333 |
| 6 | 50 | 10 | 0.3 | 0.3 |
| 6 | 60 | 18 | 0.333 | 0.333 |
| 6 | 70 | 8 | 0.125 | 0.125 |
| 6 | 80 | 8 | 0.25 | 0.25 |
| 6 | 90 | 7 | 0.143 | 0.143 |
| 6 | 100 | 10 | 0.4 | 0.4 |
| 6 | 110 | 4 | 0.25 | 0.25 |
| 7 | 10 | 6 | 0.167 | 0 |
| 7 | 20 | 12 | 0.25 | 0.083 |
| 7 | 30 | 16 | 0.25 | 0.125 |
| 7 | 40 | 14 | 0.357 | 0.286 |
| 7 | 50 | 16 | 0.563 | 0.563 |
| 7 | 60 | 15 | 0.333 | 0.333 |
| 7 | 70 | 9 | 0.444 | 0.444 |
| 7 | 80 | 5 | 0.4 | 0.4 |
| 7 | 90 | 7 | 0.143 | 0.143 |
| 7 | 100 | 3 | 0.333 | 0.333 |
| 8 | 10 | 8 | 0.5 | 0 |
| 8 | 20 | 10 | 0.7 | 0 |
| 8 | 30 | 15 | 0.333 | 0 |
| 8 | 40 | 13 | 0.231 | 0.154 |
| 8 | 50 | 11 | 0.182 | 0.182 |
| 8 | 60 | 4 | 0 | 0 |
| 8 | 70 | 10 | 0.4 | 0 |
| 8 | 80 | 6 | 0.167 | 0 |
| 8 | 90 | 11 | 0.273 | 0.182 |
| 8 | 100 | 5 | 0.6 | 0.6 |
| 9 | 20 | 9 | 0.222 | 0 |
| 9 | 30 | 15 | 0.4 | 0 |
| 9 | 40 | 10 | 0.6 | 0 |
| 9 | 50 | 13 | 0.077 | 0.077 |
| 9 | 60 | 9 | 0.333 | 0.111 |
| 9 | 70 | 6 | 0.333 | 0.167 |
| 9 | 80 | 4 | 0.25 | 0.25 |
| 10 | 10 | 7 | 0.571 | 0.286 |
| 10 | 20 | 15 | 0.6 | 0.267 |
| 10 | 30 | 19 | 0.368 | 0.316 |
| 10 | 40 | 12 | 0.417 | 0.25 |
| 10 | 50 | 6 | 0.833 | 0 |
| 10 | 60 | 9 | 0.444 | 0.333 |
| 10 | 70 | 2 | 0 | 0 |
| 10 | 80 | 8 | 0.375 | 0.375 |
| 10 | 90 | 7 | 0 | 0 |
| 10 | 100 | 3 | 0.333 | 0 |
| 11 | 10 | 7 | 0.429 | 0 |
| 11 | 20 | 8 | 0.625 | 0.5 |
| 11 | 30 | 15 | 0.467 | 0.2 |

TABLE G-continued

Chromosome Bins, Hetero/
Frequency at Chromosomes 11 and 07.
Hetero 11 07 chr bin

| chr | bins | Freq | hetero11 | hetero07 |
|---|---|---|---|---|
| 11 | 40 | 15 | 0.267 | 0.2 |
| 11 | 50 | 16 | 0.375 | 0.188 |
| 11 | 60 | 7 | 0 | 0 |
| 11 | 70 | 6 | 0.333 | 0.333 |
| 11 | 80 | 4 | 0.5 | 0.5 |
| 12 | 10 | 13 | 0.308 | 0 |
| 12 | 20 | 9 | 0.333 | 0 |
| 12 | 30 | 13 | 0.462 | 0.154 |
| 12 | 40 | 12 | 0.583 | 0.083 |
| 12 | 50 | 9 | 0.333 | 0 |
| 12 | 60 | 5 | 0.2 | 0 |
| 12 | 70 | 7 | 0.286 | 0 |
| 12 | 80 | 3 | 0.333 | 0.333 |
| 12 | 90 | 4 | 0.75 | 0.75 |
| 12 | 100 | 2 | 0 | 0 |
| 13 | 20 | 1 | 0 | 0 |
| 13 | 30 | 4 | 0.25 | 0 |
| 13 | 40 | 10 | 0 | 0 |
| 13 | 50 | 7 | 0.429 | 0.429 |
| 13 | 60 | 9 | 0.111 | 0.111 |
| 13 | 70 | 8 | 0.25 | 0.25 |
| 13 | 80 | 9 | 0.444 | 0.444 |
| 13 | 90 | 7 | 0.429 | 0.286 |
| 13 | 100 | 11 | 0.273 | 0 |
| 13 | 110 | 11 | 0.182 | 0 |
| 13 | 120 | 1 | 0 | 0 |
| 14 | 20 | 1 | 0 | 0 |
| 14 | 30 | 7 | 0.143 | 0 |
| 14 | 40 | 8 | 0.625 | 0.25 |
| 14 | 50 | 8 | 0.375 | 0.375 |
| 14 | 60 | 9 | 0.444 | 0.444 |
| 14 | 70 | 6 | 0.167 | 0.167 |
| 14 | 80 | 8 | 0.25 | 0.25 |
| 14 | 90 | 7 | 0.143 | 0.143 |
| 14 | 100 | 6 | 0.167 | 0.167 |
| 14 | 110 | 2 | 1 | 1 |
| 15 | 30 | 5 | 0.4 | 0.4 |
| 15 | 40 | 5 | 0.4 | 0.4 |
| 15 | 50 | 3 | 0.333 | 0.333 |
| 15 | 60 | 6 | 0.333 | 0.333 |
| 15 | 70 | 5 | 0.2 | 0.2 |
| 15 | 80 | 5 | 0.6 | 0.6 |
| 15 | 90 | 7 | 0.571 | 0.571 |
| 15 | 100 | 5 | 0.2 | 0.2 |
| 15 | 110 | 1 | 0 | 0 |

TABLE H

Chromosome Bins, Hetero/
Frequency at Chromosomes 11 and 08.
Hetero 11 08 chr bin

| chr | bins | freq | hetero11 | hetero08 |
|---|---|---|---|---|
|  |  | 1459 | 0.326 | 0.206 |
|  | 10 | 91 | 0.33 | 0.066 |
|  | 20 | 135 | 0.319 | 0.163 |
|  | 30 | 185 | 0.346 | 0.27 |
|  | 40 | 169 | 0.367 | 0.302 |
|  | 50 | 157 | 0.344 | 0.21 |
|  | 60 | 153 | 0.294 | 0.157 |
|  | 70 | 123 | 0.276 | 0.187 |
|  | 80 | 113 | 0.345 | 0.195 |
|  | 90 | 118 | 0.254 | 0.136 |
|  | 100 | 88 | 0.33 | 0.25 |
|  | 110 | 49 | 0.327 | 0.265 |
|  | 120 | 29 | 0.345 | 0.241 |
|  | 130 | 26 | 0.423 | 0.231 |
|  | 140 | 20 | 0.4 | 0.25 |
|  | 150 | 3 | 0 | 0 |
| 1 |  | 142 | 0.317 | 0.169 |
| 2 |  | 150 | 0.273 | 0.187 |
| 3 |  | 111 | 0.288 | 0.153 |
| 4 |  | 133 | 0.338 | 0.15 |
| 5 |  | 121 | 0.355 | 0.248 |
| 6 |  | 115 | 0.252 | 0.165 |
| 7 |  | 103 | 0.34 | 0.282 |
| 8 |  | 93 | 0.344 | 0.269 |
| 9 |  | 66 | 0.318 | 0.288 |
| 10 |  | 88 | 0.432 | 0.227 |
| 11 |  | 78 | 0.372 | 0.256 |
| 12 |  | 77 | 0.39 | 0.169 |
| 13 |  | 78 | 0.244 | 0.231 |
| 14 |  | 62 | 0.323 | 0.145 |
| 15 |  | 42 | 0.381 | 0.214 |
| 1 | 20 | 9 | 0.333 | 0 |
| 1 | 30 | 14 | 0.429 | 0.286 |
| 1 | 40 | 12 | 0.333 | 0.333 |
| 1 | 50 | 15 | 0.333 | 0.333 |
| 1 | 60 | 21 | 0.286 | 0.143 |
| 1 | 70 | 19 | 0.211 | 0.105 |
| 1 | 80 | 9 | 0.222 | 0 |
| 1 | 90 | 13 | 0.231 | 0 |
| 1 | 100 | 13 | 0.462 | 0.077 |
| 1 | 110 | 8 | 0.25 | 0.125 |
| 1 | 120 | 6 | 0.333 | 0.333 |
| 1 | 130 | 3 | 0.667 | 0.667 |
| 2 | 10 | 3 | 0 | 0 |
| 2 | 20 | 11 | 0.455 | 0.273 |
| 2 | 30 | 13 | 0.308 | 0.308 |
| 2 | 40 | 6 | 0 | 0 |
| 2 | 50 | 19 | 0.211 | 0.211 |
| 2 | 60 | 13 | 0.462 | 0.231 |
| 2 | 70 | 10 | 0.2 | 0 |
| 2 | 80 | 13 | 0.231 | 0.077 |
| 2 | 90 | 19 | 0.368 | 0.158 |
| 2 | 100 | 7 | 0 | 0 |
| 2 | 110 | 4 | 0.25 | 0.25 |
| 2 | 120 | 7 | 0.143 | 0.143 |
| 2 | 130 | 11 | 0.364 | 0.364 |
| 2 | 140 | 11 | 0.364 | 0.364 |
| 2 | 150 | 3 | 0 | 0 |
| 3 | 10 | 9 | 0.333 | 0 |
| 3 | 20 | 15 | 0.067 | 0.067 |
| 3 | 30 | 12 | 0.25 | 0.25 |
| 3 | 40 | 11 | 0.545 | 0.545 |
| 3 | 50 | 3 | 0.333 | 0.333 |
| 3 | 60 | 12 | 0.167 | 0.167 |
| 3 | 70 | 12 | 0.333 | 0.083 |
| 3 | 80 | 14 | 0.5 | 0 |
| 3 | 90 | 12 | 0.167 | 0 |
| 3 | 100 | 9 | 0.333 | 0.333 |
| 3 | 110 | 2 | 0 | 0 |
| 4 | 10 | 13 | 0.308 | 0.077 |
| 4 | 20 | 9 | 0.222 | 0.222 |
| 4 | 30 | 15 | 0.333 | 0.333 |
| 4 | 40 | 15 | 0.467 | 0.2 |
| 4 | 50 | 11 | 0.273 | 0 |
| 4 | 60 | 8 | 0.5 | 0 |
| 4 | 70 | 7 | 0.286 | 0.286 |
| 4 | 80 | 9 | 0.333 | 0.333 |
| 4 | 90 | 9 | 0.111 | 0.111 |
| 4 | 100 | 7 | 0.286 | 0.286 |
| 4 | 110 | 8 | 0.25 | 0 |
| 4 | 120 | 7 | 0.429 | 0 |
| 4 | 130 | 8 | 0.5 | 0 |
| 4 | 140 | 7 | 0.429 | 0.143 |
| 5 | 10 | 12 | 0.333 | 0.167 |
| 5 | 20 | 12 | 0.083 | 0.083 |
| 5 | 30 | 11 | 0.455 | 0.455 |
| 5 | 40 | 14 | 0.286 | 0.286 |
| 5 | 50 | 10 | 0.5 | 0.1 |
| 5 | 60 | 8 | 0.125 | 0 |
| 5 | 70 | 8 | 0.375 | 0 |
| 5 | 80 | 8 | 0.375 | 0.25 |

TABLE H-continued

Chromosome Bins, Hetero/
Frequency at Chromosomes 11 and 08.
Hetero 11 08 chr bin

| chr | bins | freq | hetero11 | hetero08 |
|---|---|---|---|---|
| 5 | 90 | 8 | 0.125 | 0.125 |
| 5 | 100 | 7 | 0.571 | 0.571 |
| 5 | 110 | 9 | 0.667 | 0.667 |
| 5 | 120 | 8 | 0.5 | 0.5 |
| 5 | 130 | 4 | 0.25 | 0 |
| 5 | 140 | 2 | 0.5 | 0 |
| 6 | 10 | 13 | 0.231 | 0 |
| 6 | 20 | 14 | 0.143 | 0.143 |
| 6 | 30 | 11 | 0.182 | 0.182 |
| 6 | 40 | 12 | 0.333 | 0.333 |
| 6 | 50 | 10 | 0.3 | 0.1 |
| 6 | 60 | 18 | 0.333 | 0.056 |
| 6 | 70 | 8 | 0.125 | 0.125 |
| 6 | 80 | 8 | 0.25 | 0.25 |
| 6 | 90 | 7 | 0.143 | 0.143 |
| 6 | 100 | 10 | 0.4 | 0.4 |
| 6 | 110 | 4 | 0.25 | 0.25 |
| 7 | 10 | 6 | 0.167 | 0 |
| 7 | 20 | 12 | 0.25 | 0.167 |
| 7 | 30 | 16 | 0.25 | 0.25 |
| 7 | 40 | 14 | 0.357 | 0.357 |
| 7 | 50 | 16 | 0.563 | 0.375 |
| 7 | 60 | 15 | 0.333 | 0.333 |
| 7 | 70 | 9 | 0.444 | 0.444 |
| 7 | 80 | 5 | 0.4 | 0.4 |
| 7 | 90 | 7 | 0.143 | 0.143 |
| 7 | 100 | 3 | 0.333 | 0 |
| 8 | 10 | 8 | 0.5 | 0.25 |
| 8 | 20 | 10 | 0.7 | 0.3 |
| 8 | 30 | 15 | 0.333 | 0.333 |
| 8 | 40 | 13 | 0.231 | 0.231 |
| 8 | 50 | 11 | 0.182 | 0.091 |
| 8 | 60 | 4 | 0 | 0 |
| 8 | 70 | 10 | 0.4 | 0.4 |
| 8 | 80 | 6 | 0.167 | 0.167 |
| 8 | 90 | 11 | 0.273 | 0.273 |
| 8 | 100 | 5 | 0.6 | 0.6 |
| 9 | 20 | 9 | 0.222 | 0 |
| 9 | 30 | 15 | 0.4 | 0.4 |
| 9 | 40 | 10 | 0.6 | 0.6 |
| 9 | 50 | 13 | 0.077 | 0.077 |
| 9 | 60 | 9 | 0.333 | 0.333 |
| 9 | 70 | 6 | 0.333 | 0.333 |
| 9 | 80 | 4 | 0.25 | 0.25 |
| 10 | 10 | 7 | 0.571 | 0 |
| 10 | 20 | 15 | 0.6 | 0.133 |
| 10 | 30 | 19 | 0.368 | 0.053 |
| 10 | 40 | 12 | 0.417 | 0.417 |
| 10 | 50 | 6 | 0.833 | 0.833 |
| 10 | 60 | 9 | 0.444 | 0.444 |
| 10 | 70 | 2 | 0 | 0 |
| 10 | 80 | 8 | 0.375 | 0.375 |
| 10 | 90 | 7 | 0 | 0 |
| 10 | 100 | 3 | 0.333 | 0 |
| 11 | 10 | 7 | 0.429 | 0 |
| 11 | 20 | 8 | 0.625 | 0.375 |
| 11 | 30 | 15 | 0.467 | 0.467 |
| 11 | 40 | 15 | 0.267 | 0.2 |
| 11 | 50 | 16 | 0.375 | 0.188 |
| 11 | 60 | 7 | 0 | 0 |
| 11 | 70 | 6 | 0.333 | 0.333 |
| 11 | 80 | 4 | 0.5 | 0.5 |
| 12 | 10 | 13 | 0.308 | 0.077 |
| 12 | 20 | 9 | 0.333 | 0.333 |
| 12 | 30 | 13 | 0.462 | 0.154 |
| 12 | 40 | 12 | 0.583 | 0.083 |
| 12 | 50 | 9 | 0.333 | 0 |
| 12 | 60 | 5 | 0.2 | 0 |
| 12 | 70 | 7 | 0.286 | 0.286 |
| 12 | 80 | 3 | 0.333 | 0.333 |
| 12 | 90 | 4 | 0.75 | 0.75 |
| 12 | 100 | 2 | 0 | 0 |
| 13 | 20 | 1 | 0 | 0 |
| 13 | 30 | 4 | 0.25 | 0 |
| 13 | 40 | 10 | 0 | 0 |
| 13 | 50 | 7 | 0.429 | 0.429 |
| 13 | 60 | 9 | 0.111 | 0.111 |
| 13 | 70 | 8 | 0.25 | 0.25 |
| 13 | 80 | 9 | 0.444 | 0.444 |
| 13 | 90 | 7 | 0.429 | 0.429 |
| 13 | 100 | 11 | 0.273 | 0.273 |
| 13 | 110 | 11 | 0.182 | 0.182 |
| 13 | 120 | 1 | 0 | 0 |
| 14 | 20 | 1 | 0 | 0 |
| 14 | 30 | 7 | 0.143 | 0 |
| 14 | 40 | 8 | 0.625 | 0.625 |
| 14 | 50 | 8 | 0.375 | 0.125 |
| 14 | 60 | 9 | 0.444 | 0 |
| 14 | 70 | 6 | 0.167 | 0 |
| 14 | 80 | 8 | 0.25 | 0 |
| 14 | 90 | 7 | 0.143 | 0 |
| 14 | 100 | 6 | 0.167 | 0.167 |
| 14 | 110 | 2 | 1 | 1 |
| 15 | 30 | 5 | 0.4 | 0.4 |
| 15 | 40 | 5 | 0.4 | 0.4 |
| 15 | 50 | 3 | 0.333 | 0.333 |
| 15 | 60 | 6 | 0.333 | 0.333 |
| 15 | 70 | 5 | 0.2 | 0.2 |
| 15 | 80 | 5 | 0.6 | 0 |
| 15 | 90 | 7 | 0.571 | 0 |
| 15 | 100 | 5 | 0.2 | 0.2 |
| 15 | 110 | 1 | 0 | 0 |

TABLE I

Chromosome Bins, Hetero/
Frequency at Chromosomes 10 and 09.
hetero 10 09 chr bin

| Chr | bins | Freq | hetero10 | hetero09 |
|---|---|---|---|---|
|  |  | 1459 | 0.378 | 0.222 |
|  | 10 | 91 | 0.473 | 0.066 |
|  | 20 | 135 | 0.319 | 0.178 |
|  | 30 | 185 | 0.314 | 0.227 |
|  | 40 | 169 | 0.467 | 0.402 |
|  | 50 | 157 | 0.357 | 0.21 |
|  | 60 | 153 | 0.405 | 0.216 |
|  | 70 | 123 | 0.358 | 0.138 |
|  | 80 | 113 | 0.363 | 0.257 |
|  | 90 | 118 | 0.373 | 0.237 |
|  | 100 | 88 | 0.432 | 0.216 |
|  | 110 | 49 | 0.408 | 0.184 |
|  | 120 | 29 | 0.31 | 0.207 |
|  | 130 | 26 | 0.308 | 0.269 |
|  | 140 | 20 | 0.2 | 0.1 |
|  | 150 | 3 | 1 | 0.333 |
| 1 |  | 142 | 0.387 | 0.218 |
| 2 |  | 150 | 0.353 | 0.253 |
| 3 |  | 111 | 0.405 | 0.243 |
| 4 |  | 133 | 0.346 | 0.218 |
| 5 |  | 121 | 0.413 | 0.198 |
| 6 |  | 115 | 0.409 | 0.243 |
| 7 |  | 103 | 0.359 | 0.233 |
| 8 |  | 93 | 0.398 | 0:118 |
| 9 |  | 66 | 0.333 | 0.273 |
| 10 |  | 88 | 0.341 | 0.273 |
| 11 |  | 78 | 0.372 | 0.167 |
| 12 |  | 77 | 0.429 | 0.182 |
| 13 |  | 78 | 0.423 | 0.256 |
| 14 |  | 62 | 0.339 | 0.226 |
| 15 |  | 42 | 0.333 | 0.214 |
| 1 | 20 | 9 | 0.556 | 0.222 |
| 1 | 30 | 14 | 0.357 | 0.071 |
| 1 | 40 | 12 | 0.333 | 0.333 |

TABLE I-continued

Chromosome Bins, Hetero/
Frequency at Chromosomes 10 and 09.
hetero 10 09 chr bin

| Chr | bins | Freq | hetero10 | hetero09 |
|---|---|---|---|---|
| 1 | 50 | 15 | 0.267 | 0.2 |
| 1 | 60 | 21 | 0.429 | 0.286 |
| 1 | 70 | 19 | 0.526 | 0.263 |
| 1 | 80 | 9 | 0.222 | 0.222 |
| 1 | 90 | 13 | 0.077 | 0 |
| 1 | 100 | 13 | 0.385 | 0.308 |
| 1 | 110 | 8 | 0.625 | 0.125 |
| 1 | 120 | 6 | 0.5 | 0.167 |
| 1 | 130 | 3 | 0.667 | 0.667 |
| 2 | 10 | 3 | 0.333 | 0 |
| 2 | 20 | 11 | 0.364 | 0.364 |
| 2 | 30 | 13 | 0.308 | 0.308 |
| 2 | 40 | 6 | 0 | 0 |
| 2 | 50 | 19 | 0.263 | 0.263 |
| 2 | 60 | 13 | 0.615 | 0.231 |
| 2 | 70 | 10 | 0.3 | 0.2 |
| 2 | 80 | 13 | 0.538 | 0.385 |
| 2 | 90 | 19 | 0.421 | 0.368 |
| 2 | 100 | 7 | 0.571 | 0.571 |
| 2 | 110 | 4 | 0 | 0 |
| 2 | 120 | 7 | 0.286 | 0.286 |
| 2 | 130 | 11 | 0.182 | 0.091 |
| 2 | 140 | 11 | 0.182 | 0 |
| 2 | 150 | 3 | 1 | 0.333 |
| 3 | 10 | 9 | 0.333 | 0 |
| 3 | 20 | 15 | 0.4 | 0.067 |
| 3 | 30 | 12 | 0.333 | 0.25 |
| 3 | 40 | 11 | 0.636 | 0.636 |
| 3 | 50 | 3 | 0 | 0 |
| 3 | 60 | 12 | 0.333 | 0.25 |
| 3 | 70 | 12 | 0.417 | 0.25 |
| 3 | 80 | 14 | 0.571 | 0.357 |
| 3 | 90 | 12 | 0.25 | 0.167 |
| 3 | 100 | 9 | 0.444 | 0.222 |
| 3 | 110 | 2 | 0.5 | 0.5 |
| 4 | 10 | 13 | 0.615 | 0.154 |
| 4 | 20 | 9 | 0.111 | 0.111 |
| 4 | 30 | 15 | 0.2 | 0.067 |
| 4 | 40 | 15 | 0.267 | 0.133 |
| 4 | 50 | 11 | 0.545 | 0.182 |
| 4 | 60 | 8 | 0.375 | 0.375 |
| 4 | 70 | 7 | 0 | 0 |
| 4 | 80 | 9 | 0.222 | 0.222 |
| 4 | 90 | 9 | 0.667 | 0.667 |
| 4 | 100 | 7 | 0.286 | 0 |
| 4 | 110 | 8 | 0.5 | 0.375 |
| 4 | 120 | 7 | 0.429 | 0.429 |
| 4 | 130 | 8 | 0.25 | 0.25 |
| 4 | 140 | 7 | 0.286 | 0.286 |
| 5 | 10 | 12 | 0.417 | 0 |
| 5 | 20 | 12 | 0.25 | 0.167 |
| 5 | 30 | 11 | 0.455 | 0.455 |
| 5 | 40 | 14 | 0.5 | 0.357 |
| 5 | 50 | 10 | 0.7 | 0.2 |
| 5 | 60 | 8 | 0.375 | 0 |
| 5 | 70 | 8 | 0.25 | 0 |
| 5 | 80 | 8 | 0.375 | 0.375 |
| 5 | 90 | 8 | 0.5 | 0.5 |
| 5 | 100 | 7 | 0.571 | 0 |
| 5 | 110 | 9 | 0.444 | 0.111 |
| 5 | 120 | 8 | 0.125 | 0 |
| 5 | 130 | 4 | 0.5 | 0.5 |
| 5 | 140 | 2 | 0 | 0 |
| 6 | 10 | 13 | 0.462 | 0.154 |
| 6 | 20 | 14 | 0.286 | 0.143 |
| 6 | 30 | 11 | 0.364 | 0.364 |
| 6 | 40 | 12 | 0.583 | 0.583 |
| 6 | 50 | 10 | 0.3 | 0.3 |
| 6 | 60 | 18 | 0.278 | 0.278 |
| 6 | 70 | 8 | 0.375 | 0.375 |
| 6 | 80 | 8 | 0.375 | 0.25 |
| 6 | 90 | 7 | 0.714 | 0 |
| 6 | 100 | 10 | 0.7 | 0 |
| 6 | 110 | 4 | 0 | 0 |
| 7 | 10 | 6 | 0.5 | 0.167 |
| 7 | 20 | 12 | 0.25 | 0.25 |
| 7 | 30 | 16 | 0.313 | 0.313 |
| 7 | 40 | 14 | 0.571 | 0.571 |
| 7 | 50 | 16 | 0.25 | 0.25 |
| 7 | 60 | 15 | 0.6 | 0.2 |
| 7 | 70 | 9 | 0.444 | 0 |
| 7 | 80 | 5 | 0.2 | 0 |
| 7 | 90 | 7 | 0 | 0 |
| 7 | 100 | 3 | 0 | 0 |
| 8 | 10 | 8 | 0.25 | 0 |
| 8 | 20 | 10 | 0.4 | 0.3 |
| 8 | 30 | 15 | 0.467 | 0.2 |
| 8 | 40 | 13 | 0.308 | 0.154 |
| 8 | 50 | 11 | 0.364 | 0.182 |
| 8 | 60 | 4 | 0.5 | 0.25 |
| 8 | 70 | 10 | 0.5 | 0 |
| 8 | 80 | 6 | 0.5 | 0 |
| 8 | 90 | 11 | 0.455 | 0 |
| 8 | 100 | 5 | 0.2 | 0 |
| 9 | 20 | 9 | 0.333 | 0.111 |
| 9 | 30 | 15 | 0.133 | 0.067 |
| 9 | 40 | 10 | 0.6 | 0.5 |
| 9 | 50 | 13 | 0.385 | 0.385 |
| 9 | 60 | 9 | 0.333 | 0.333 |
| 9 | 70 | 6 | 0.167 | 0.167 |
| 9 | 80 | 4 | 0.5 | 0.5 |
| 10 | 10 | 7 | 0.571 | 0 |
| 10 | 20 | 15 | 0.267 | 0.133 |
| 10 | 30 | 19 | 0.263 | 0.263 |
| 10 | 40 | 12 | 0.417 | 0.417 |
| 10 | 50 | 6 | 0.167 | 0.167 |
| 10 | 60 | 9 | 0.222 | 0.222 |
| 10 | 70 | 2 | 0.5 | 0.5 |
| 10 | 80 | 8 | 0.375 | 0.375 |
| 10 | 90 | 7 | 0.571 | 0.571 |
| 10 | 100 | 3 | 0.333 | 0.333 |
| 11 | 10 | 7 | 0.571 | 0.143 |
| 11 | 20 | 8 | 0.25 | 0 |
| 11 | 30 | 15 | 0.333 | 0.333 |
| 11 | 40 | 15 | 0.267 | 0.267 |
| 11 | 50 | 16 | 0.563 | 0.188 |
| 11 | 60 | 7 | 0.286 | 0 |
| 11 | 70 | 6 | 0.5 | 0 |
| 11 | 80 | 4 | 0 | 0 |
| 12 | 10 | 13 | 0.538 | 0 |
| 12 | 20 | 9 | 0.333 | 0.333 |
| 12 | 30 | 13 | 0.154 | 0.077 |
| 12 | 40 | 12 | 0.75 | 0.5 |
| 12 | 50 | 9 | 0.444 | 0 |
| 12 | 60 | 5 | 0.4 | 0 |
| 12 | 70 | 7 | 0.286 | 0.286 |
| 12 | 80 | 3 | 0.333 | 0.333 |
| 12 | 90 | 4 | 0.25 | 0 |
| 12 | 100 | 2 | 1 | 0.5 |
| 13 | 20 | 1 | 1 | 0 |
| 13 | 30 | 4 | 0.25 | 0 |
| 13 | 40 | 10 | 0.7 | 0.7 |
| 13 | 50 | 7 | 0.429 | 0.286 |
| 13 | 60 | 9 | 0.444 | 0 |
| 13 | 70 | 8 | 0.375 | 0 |
| 13 | 80 | 9 | 0.222 | 0.111 |
| 13 | 90 | 7 | 0.429 | 0.429 |
| 13 | 100 | 11 | 0.364 | 0.364 |
| 13 | 110 | 11 | 0.455 | 0.273 |
| 13 | 120 | 1 | 0 | 0 |
| 14 | 20 | 1 | 0 | 0 |
| 14 | 30 | 7 | 0.571 | 0.571 |
| 14 | 40 | 8 | 0.5 | 0.5 |
| 14 | 50 | 8 | 0.125 | 0.125 |
| 14 | 60 | 9 | 0.444 | 0.222 |
| 14 | 70 | 6 | 0.333 | 0 |
| 14 | 80 | 8 | 0.125 | 0 |
| 14 | 90 | 7 | 0.286 | 0 |

TABLE I-continued

Chromosome Bins, Hetero/
Frequency at Chromosomes 10 and 09.
hetero 10 09 chr bin

| Chr | bins | Freq | hetero10 | hetero09 |
|---|---|---|---|---|
| 14 | 100 | 6 | 0.5 | 0.5 |
| 14 | 110 | 2 | 0 | 0 |
| 15 | 30 | 5 | 0.4 | 0 |
| 15 | 40 | 5 | 0.6 | 0.4 |
| 15 | 50 | 3 | 0 | 0 |
| 15 | 60 | 6 | 0.333 | 0.333 |
| 15 | 70 | 5 | 0 | 0 |
| 15 | 80 | 5 | 0.6 | 0.6 |
| 15 | 90 | 7 | 0.286 | 0.286 |
| 15 | 100 | 5 | 0.2 | 0 |
| 15 | 110 | 1 | 1 | 0 |

Chr = chromosome number considered; Bins = specific interval, with number given for the upper bound of 10 Mbp interval from the centromere; Freq = number of SNP markers for each combination of chromosome and interval considered; The other columns are for the proportion of heterozygosity for each combination of chromosome and interval considered; chr=., bins=.
Line: Overall summary for all 1459 markers in the sample; chr=., bins =  Lines: interval-by-interval summary, summed up across all chromosomes; chr = , bins=.
Lines: chromosome-by-chromosome summary, summed up across all intervals; chr = , bins =  Lines: Summary for each combination of chromosome and interval.

In all 7 pairs, stem cells exhibit lower proportions of heterozygosity than their donor cell counterparts. On the whole, donor cells do not seem to exhibit a clear pattern of heterozygosity trend across distances from centromeres, whereas stem cells display somewhat lower proportions of heterozygosity near centromeres and telomeres in comparison to heterozygosity proportions in the middle.

Based on the HLA-typing results, stem cells derived of all phESC lines appeared MHC-matched with the oocyte donors, making this a possible method to create cells for therapeutic use (Table 3). HLA-analysis of the genetic material from the human fibroblasts used as feeder cells revealed no contamination of the phESC lines with material from the human fibroblasts (Table 3).

TABLE 3

HLA-typing results.

| | MHCI | | | MHCH | | |
|---|---|---|---|---|---|---|
| | HLA-A | HLA-B | HLA-C | DRB1 | DQB1 | DQA1 |
| phESC-1 | A*01 | B*15(63) | Cw*04 | DRB1*12 | DQB1*06 | DQA1*01 |
|  | A*02 | B*35 | Cw*0708 | DRB1*13 | DQB1*03 | DQA1*0505 |
| phESC-1 donor | A*01 | B*15(63) | Cw*04 | DRB1*12 | DQB1*06 | DQA1*01 |
|  | A*02 | B*35 | Cw*0708 | DRBP*13 | DQB1*03 | DQA1*0505 |
| phESC-3,4,5 | A*02 | B*52 | Cw*03 | DRB1*01 | DQB1*05 | DQA1*0101 |
|  | A*03 | B*22 | Cw*04 | DRB1*03 | DQB1*02 | DQA1*05 |
| phESC-3,4,5 donor | A*02 | B*52 | Cw*03 | DRB1*01 | DQB1*05 | DQA1*0101 |
|  | A*03 | B*22 | Cw*04 | DRB1*03 | DQB1*02 | DQA1*05 |
| phESC-6 | A*02 | B*07 | Cw*04 | DRB1*04 | DQB1*06 | DQA1*01 |
|  | A*03 | B*27 | Cw*07 | DRB1*15 | DQB1*03 | DQA1*03 |
| phESC-6 donor | A*02 | B*07 | Cw*04 | DRBP*04 | DQB1*06 | DQA1*01 |
|  | A*03 | B*27 | Cw*07 | DRB1*15 | DQB1*03 | DQA1*03 |
| phESC-7 | A*01 | B*38 | Cw*06 | DRB1*13 | DQB1*06 | DQA1*0106 |
|  | A*02 | B*57 | Cw*12 | DRB1*14 | DQB1*06 | DQA1*0103 |
| phESC-7 donor | A*01 | B*38 | Cw*06 | DRB1*13 | DQB1*06 | DQA1*0106 |
|  | A*02 | B*57 | Cw*12 | DRB1*14 | DQB1*06 | DQA1*0103 |
| NSF | A*25 | B*15(62) | Cw*12 | DRB1*04 | DQB1*06 | DQA1*01 |
|  | A*32 | B*18 | Cw*12 | DRB1*15 | DQBl*O3 | DQA1*03 |

Analysis of Imprinted Genes

Figure 6:
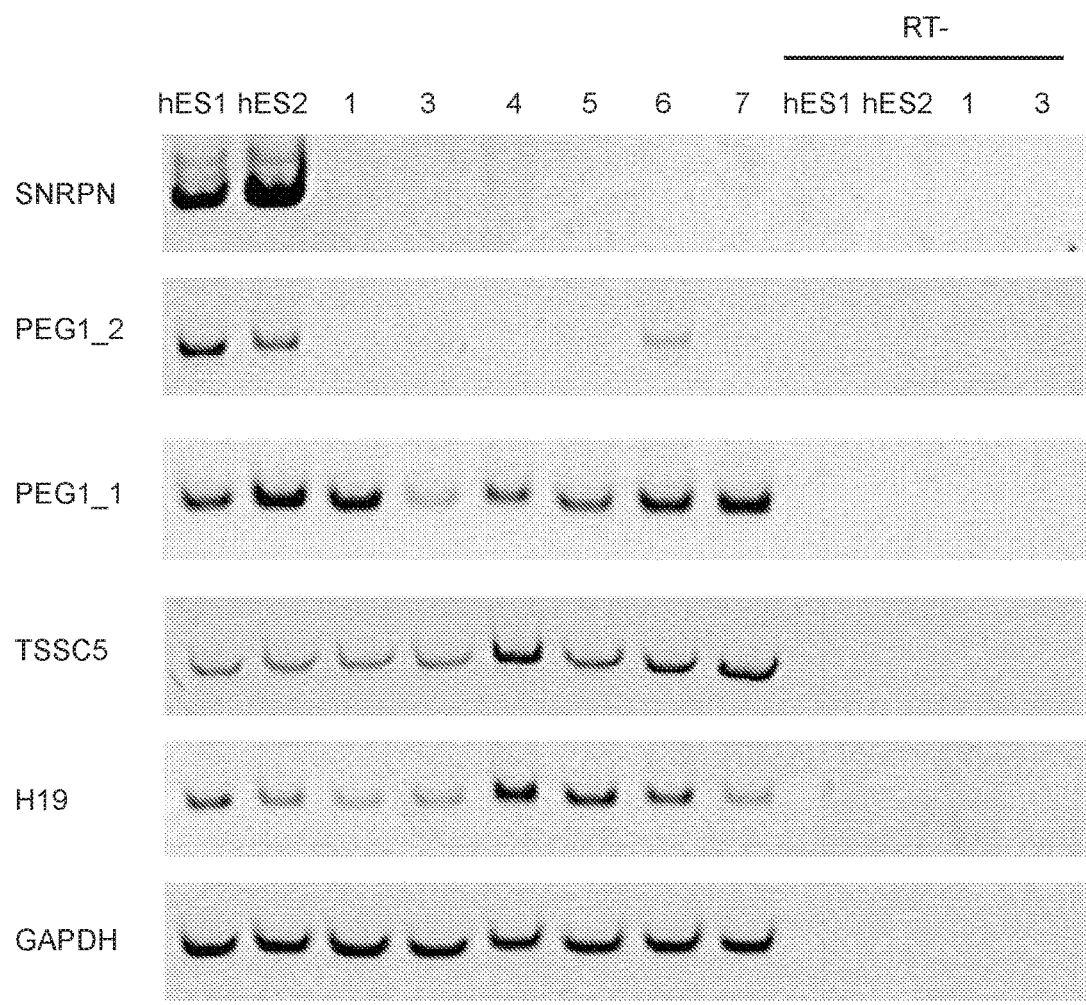
FIG. 6 shows RT-PCR analysis of imprinted gene expression. Two hESC lines hES1 and hES2 from discarded IVF embryos were used as positive controls for the expression analysis of the paternally expressed genes SNRPN and PEG1_2 and the maternally expressed genes TSSC5 and H19 in phESC lines: phESC-1; phESC-3; phESC-4; phESC-5; phESC-6 and phESC-7 (1, 3, 4, 5, 6, and 7 respectively.) The PEG1_1 gene is biallelically expressed and was used as an additional control. GAPDH was included as mRNA quantitative control. RT-data demonstrate no genomic contamination of RT samples.

Alterations of genomic imprinting in human embryos can contribute to the development of disorders linked to maternally or paternally expressed genes (Gabriel et al., Proc Natl Acad Sci USA (1998) 95:14857-14862). Studies of imprinting in phESC require a detailed investigation because of the possible influence upon phESC differentiation and functionality of their derivatives. As a preliminary study, expression analysis was performed for the human imprinted genes (Morison et al., Trends Genet (2005) 21:457-465) TSSC5, H19, PEG1 and SNRPN in undifferentiated phESC (FIG. 6). Two hESC lines derived from discarded IVF embryos were used as controls. The transcripts of maternally expressed genes TSSC5 (Morison et al., 2005, supra) and H19 (Morison et al., 2005, supra) were observed in all phESC lines and also in control lines. The human PEG1 gene is transcribed from two alternative promoters (Li et al., 2002, supra). The gene region from the first promoter is biallelically expressed, and the gene region from the second promoter (isoform 1) is paternally expressed (Li et al., 2002, supra). Expression of the PEG1 gene from the first promoter was no affected in the phESC lines. Analysis of the paternally expressed region of the PEG1 gene and the paternally expressed SNRPN gene (Morison et al., 2005, supra) demonstrated that expression of these genes was significantly downregulated in phESC lines in comparison with control hESC lines (FIG. 6 FP). These results provide further evidence of the parthenogenetic origin of the described phESC lines.

Example 2

Derivation of an hpSC-Hhom Line from an HLA Homozygous Donor

With an initial goal of isolating an HLA homozygous parthenogenetic human stem cell line, oocytes from an HLA homozygous donor were used. HLA genotyping of both the donor (donor 1) and her parents demonstrated that both parents were heterozygous. The same haplotype A*25, B*18, DRB1*15 was inherited from each parent, with the donor having an HLA homozygous genotype A*25, A*25, B*18, B*18, DRB1*15, DRB1*15 (Table 5, Case 1).

Nineteen cumulus-oocyte complexes (COCs) were taken from donor 1, of which seven were used for research (Table 4).

TABLE 4

Origin of parthenotes and HLA homozygous parthenogenetic human stem cell lines.

| Donor Number | Oocytes harvested | Oocytes donated | Blasto-cysts | Cell lines | IVF Result |
|---|---|---|---|---|---|
| 1 | 19 | 7 | 4 | hpSC-Hhom-1 | Successful |
| 2 | 18 | 7 | 3 | hpSC-Hhom-2 | Successful |
|  |  |  |  | hpSC-Hhom-3 | (Twin pregnancy) |
| 3 | 20 | 10 | 0 | 0 | Unsuccessful |
| 4 | 27 | 14 | 2 | hpSC-Hhom-4 | Successful |
| Total | 84 | 38 | 9 | 4 | NA |

Parthenogenetic activation was performed using a previously described protocol with A23187 and 6-DMAP treatment (Revazova et al., 2007, supra). Four parthenogenetic embryos achieved the blastocyst stage, from which one allowed isolation of the hpSC-Hhom-1 line.

Genotype relationship between cells of the hpSC-Hhom-1 line and donor 1 somatic cells were identified as "full siblings" (genetically matched) by SNP analysis. SNP marker comparison revealed that donor 1 cells appear to exhibit a pattern of heterozygosity whereas, hpSC-Hhom-1 cells display a lower proportion of heterozygosity.

HLA genotyping demonstrated that the hpSC-Hhom-1 line was HLA homozygous: A*25, A*25, B*18, B*18, DRB1*15, DRB1*15 and completely HLA matched with the donor (Table 5, Case 1).

TABLE 5

HLA genotyping.

| Case | | HLA-A | HLA-B | DRB1 |
|---|---|---|---|---|
| 1 | Donor's mother | **A*25** | **B*18** | **DRB1*15** |
|  |  | A*26 | B*44 | DRB1*11 |
|  | Donor's father | A*25 | B*18 | DRB1*15 |
|  |  | A*03 | B*07 | DRB1*15 |
|  | Donor | A*25 | B*18 | DRB1*15 |
|  |  | **A*25** | **B*18** | **DRB1*15** |
|  | hpSC-Hhom-1 | **A*25** | **B*18** | **DRB1*15** |
|  |  | A*25 | B*18 | DRB1*15 |
| 2 | Donor's mother | **A*02** | **B*13** | **DRB1*07** |
|  |  | A*33 | B*14 | DRB1*01 |
|  | Donor's father | A*68 | B*18 | DRB1*13 |
|  |  | A*03 | B*40 | DRB1*03 |
|  | Donor | A*02 | B*13 | DRB1*07 |
|  |  | A*68 | B*18 | DRB1*13 |
|  | hpSC-Hhom-2 | A*68 | B*18 | DRB1*13 |
|  |  | A*68 | B*18 | DRB1*13 |
|  | hpSC-Hhom-3 | **A*02** | **B*13** | **DRB1*07** |
|  |  | **A*02** | **B*13** | **DRB1*07** |
| 3 | Donor's mother | A*02 | B*08 | DRB1*03 |
|  |  | A*01 | B*15 | DRB1*01 |
|  | Donor's father | A*01 | B*51 | DRB1*11 |
|  |  | A*33 | B*15 | DRB1*04 |
|  | Donor | A*02 | B*08 | DRB1*03 |
|  |  | A*01 | B*51 | DRB1*11 |
|  | HLA haplotype N10: A*02 B*08 DRB1*03 | | | NO LINE |
| 4 | Donor's mother | A*02 | B*07 | DRB1*13 |
|  |  | A*02 | B*40 | DRB1*16 |
|  | Donor's father | A*01 | B*08 | DRB1*03 |
|  |  | A*24 | B*44 | DRB1*01 |
|  | Donor | A*02 | B*40 | DRB1*13 |
|  |  | A*01 | B*08 | DRB1*03 |

TABLE 5-continued

HLA genotyping.

| Case | | HLA-A | HLA-B | DRB1 |
|---|---|---|---|---|
|  | hpSC-Hhom-4 | A*01 | B*08 | DRB1*03 |
|  |  | A*01 | B*08 | DRB1*03 |
| Feeder | HLA haplotype N1 NSF | A*25 | B*15(62) | DRB1*04 |
|  |  | A*32 | B*18 | DRB1*15 |

Bold signifies donor's mother's HLA haplotype;
underlined signifies donor's father's HLA haplotype, each inherited by the donor and then subsequently by the hpSC-Hhom line.

Derivation of hpSC-Hhom Lines from an HLA Heterozygous Donor

Since HLA homozygous oocyte donors are a rare occurrence, isolation of HLA homozygous cell lines from oocytes obtained from HLA heterozygous donors was sought. In all, eighteen COCs were obtained from donor 2, of which seven were donated for research (Table 4). These oocytes were parthenogenetically activated using a different protocol with A23187 and puromycin treatment. Following 18 hours, 2nd polar body extrusion and formation of one pronucleus in the activated oocytes was observed. Three blastocysts developed from these zygotes, allowing isolation of two hpSC-Hhom lines: hpSC-Hhom-2 and hpSC-Hhom-3.

SNP analysis performed between oocyte donor 2's somatic cells and the hpSC-Hhom-2 and hpSC-Hhom-3 lines showed the relationship as "parent/offspring pair". Moreover both of these cell lines appeared to be homozygous throughout the genome (at the SNP markers evaluated) in contrast to the donor's heterozygous somatic cells.

Based on the HLA-genotyping results, cells from both of these lines appeared HLA homozygous: hpSC-Hhom-2 line exhibited HLA genotype A*68, A*68, B*18, B*18, DRB1*13, DRB1*13 and hpSC-Hhom-3 line exhibited HLA genotype A*02, A*02, B*13, B*13, DRB1*07, DRB1*07 (at the loci investigated). Also, each hpSC-Hhom line inherited a different HLA haplotype, one from the donor's father, and the other from the donor's mother. The donor's father's HLA haplotype (A*68, B*18, DRB1*13) was found in the homozygous state in the hpSC-Hhom-2 line and the donor's mother's HLA haplotype (A*02, B*13, DRB1*07) was found in the homozygous state in the hpSC-Hhom-3 line (Table 5, Case 2).

Isolation of hpSC-Hhom Lines from Oocytes of HLA Heterozygous Donors, Selected According to HLA Haplotype As a final step, isolation of hpSC-Hhom lines with an HLA haplotype known to have a high frequency among the population was carried out. HLA haplotype screening of IVF candidates produced two HLA heterozygous oocyte donors carrying a common haplotype. According to a published list of HLA haplotype frequencies (Mori M. et al., Transplantation (1997) 64:1017-1027), donor 3 (HLA haplotype A*02, B*08, DRB1*03) and donor 4 (HLA haplotype A*01, B*08, DRB1*03) (Table 5, Case 3 and Case 4) carried common haplotypes found within the U.S. population. However, with a heterozygous HLA genotype, each donor carried not only the frequent haplotype, but also a less common one as well. It was therefore not possible to predict with full accuracy which haplotype would be present in an isolated hpSC-Hhom line.

A23187 and puromycin were used for parthenogenetic activation of the donors' oocytes. Isolation of an hpSC-Hhom line from the oocytes of donor 3 was not successful, from which twenty COCs were obtained, with 10 oocytes donated for research. None of these reached the blastocyst stage. Furthermore, the IVF procedure for this donor was unsuccessful in achieving pregnancy. Together, these findings may reflect the poor quality of oocytes from this particular donor (Table 4).

From donor 4, 27 COCs were obtained, with fourteen oocytes donated for research. Following parthenogenetic activation of the oocytes, two blastocysts were obtained, from which the hpSC-Hhom-4 line was isolated (Table 4).

The genotype relationship between hpSC-Hhom-4 and Donor 4 somatic cells was identified as "parent/offspring pair" by SNP analysis, similar to Case 2. The hpSC-Hhom-4 line appeared homozygous throughout the genome (at the SNP markers evaluated) in comparison to the donor's heterozygous somatic cells (1,174 heterozygous SNP markers).

According to HLA genotyping, the hpSC-Hhom-4 line was HLA homozygous (at the loci evaluated) and had the most common HLA haplotype in the U.S. population, shared by a number of racial groups (Table 6): A*01, B*08, DRB1*03, (Table 5, Case 4).

TABLE 6

Frequency and ranking according to racial group for HLA haplotype A*01, B*08, DRB1*03 in the U.S. population (Adapted from Mori M. et al, 1997, supra).

| Racial Group[a] | Frequency (%)[b] | Ranking[c] |
|---|---|---|
| CAU | 5.1812 | 1 |
| NAT | 4.7439 | 1 |
| AFR | 1.2491 | 2 |
| LAT | 1.6733 | 3 |
| ASI | 0.3195 | 54 |

[a]Caucasian American (CAU), Native American (NAT), African-American (AFR), Latin American (LAT) and Asian-American (ASI).
[b]HLA-A, -B, -DR haplotype frequencies
[c]Respective ranking within each racial group IVF procedures resulted in pregnancies in three of the four donors (donors 1, 2 and 4). The high IVF success rate was largely due to the selection of donors with a good prognosis for an IVF pregnancy. Interestingly, from donor 2 two hpSC-Hhom lines were isolated, with the donor having a twin pregnancy from her IVF procedure.

Characterization of the hpSC-Hhom Lines

Figure 7:
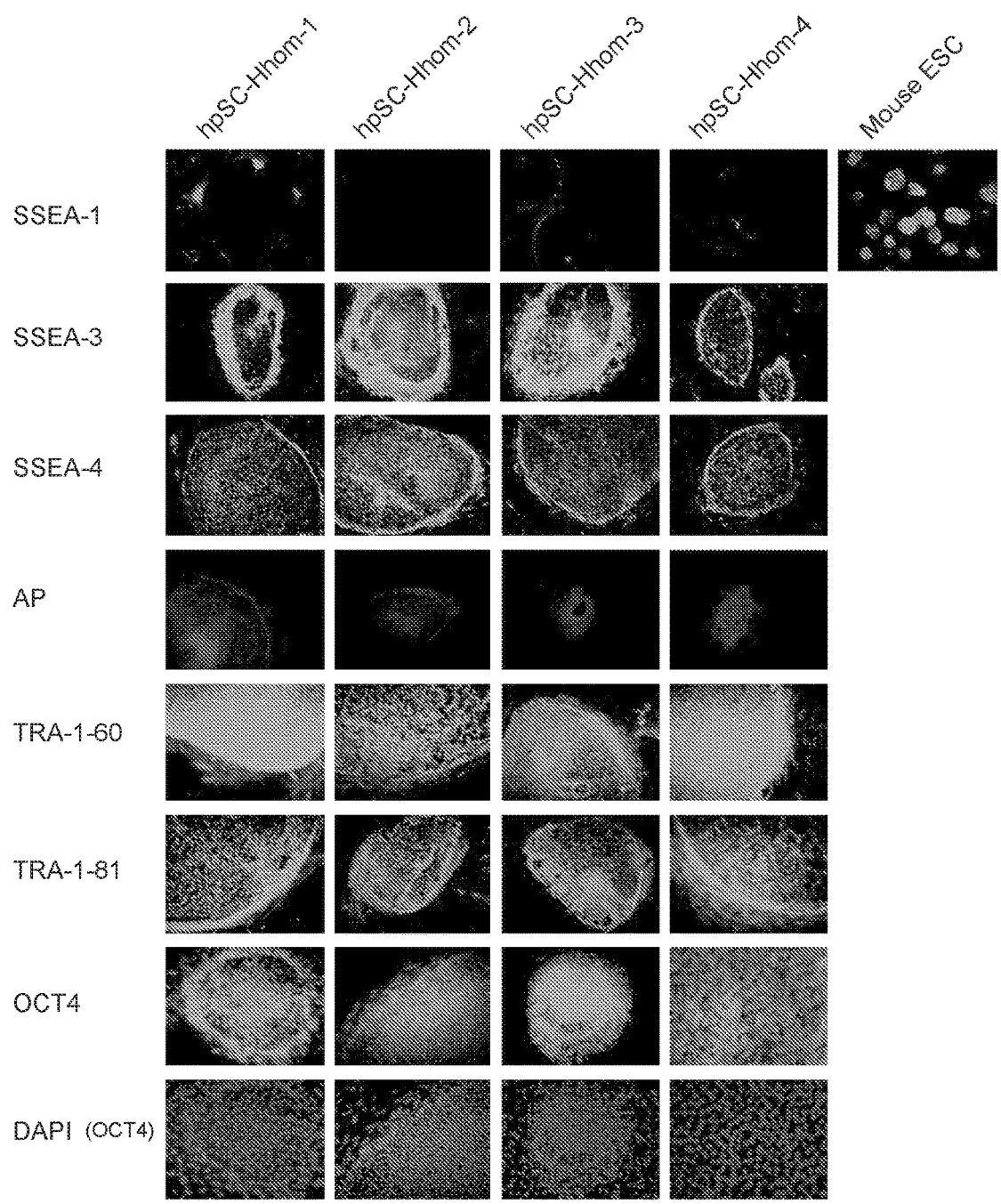
FIG. 7 shows specific markers characteristic for hpSC-Hhom lines. Cells from all four hpSC-Hhom lines demonstrate positive staining for SSEA-3, SSEA-4, TRA-1-60, TRA-1-81, OCT-4 (nuclei stained by DAPI), alkaline phosphatase and negative staining for SSEA-1. Mouse embryonic stem cells (ESC) were used as a positive control for SSAE-1 staining.
Figure 8:
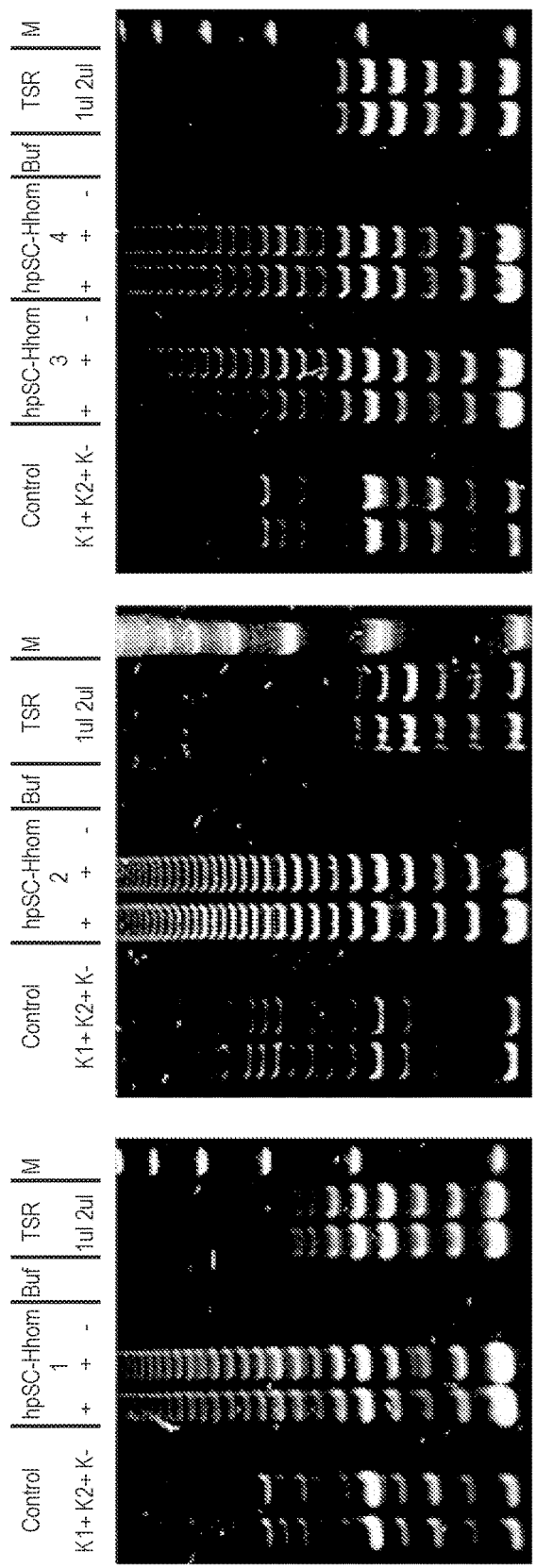
FIG. 8 shows that hpSC-Hhom lines demonstrate high levels of telomerase activity in comparison with positive control cells: "K1+"—telomerase positive cell extract (applied with TRAPEZE Kit); "K2+"—extract from 500 cells; "K−" or "−"—heat-treated cell extract with inactivated telomerase; Buf-CHAPS lysis buffer, primer-dimer/PCR contamination control; TSR-telomerase quantitative control template (0.1 and 0.2 amole/µl); "M"—marker, DNA ladder.

Cells from all of the hpSC-Hhom lines displayed morphology expected from human embryonic stem cells, formed densely-packed colonies, and displayed prominent nucleoli with a small cytoplasm to nucleus ratio. All cells expressed common human embryonic stem cell markers SSEA-3, SSEA-4, TRA-1-60, TRA-1-81 and OCT-4, while not expressing SSEA-1, a positive marker for undifferentiated mouse embryonic stem cells (FIG. 7). All lines exhibited high levels of alkaline phosphatase (FIG. 7) and telomerase activity (FIG. 8).

Figure 9:
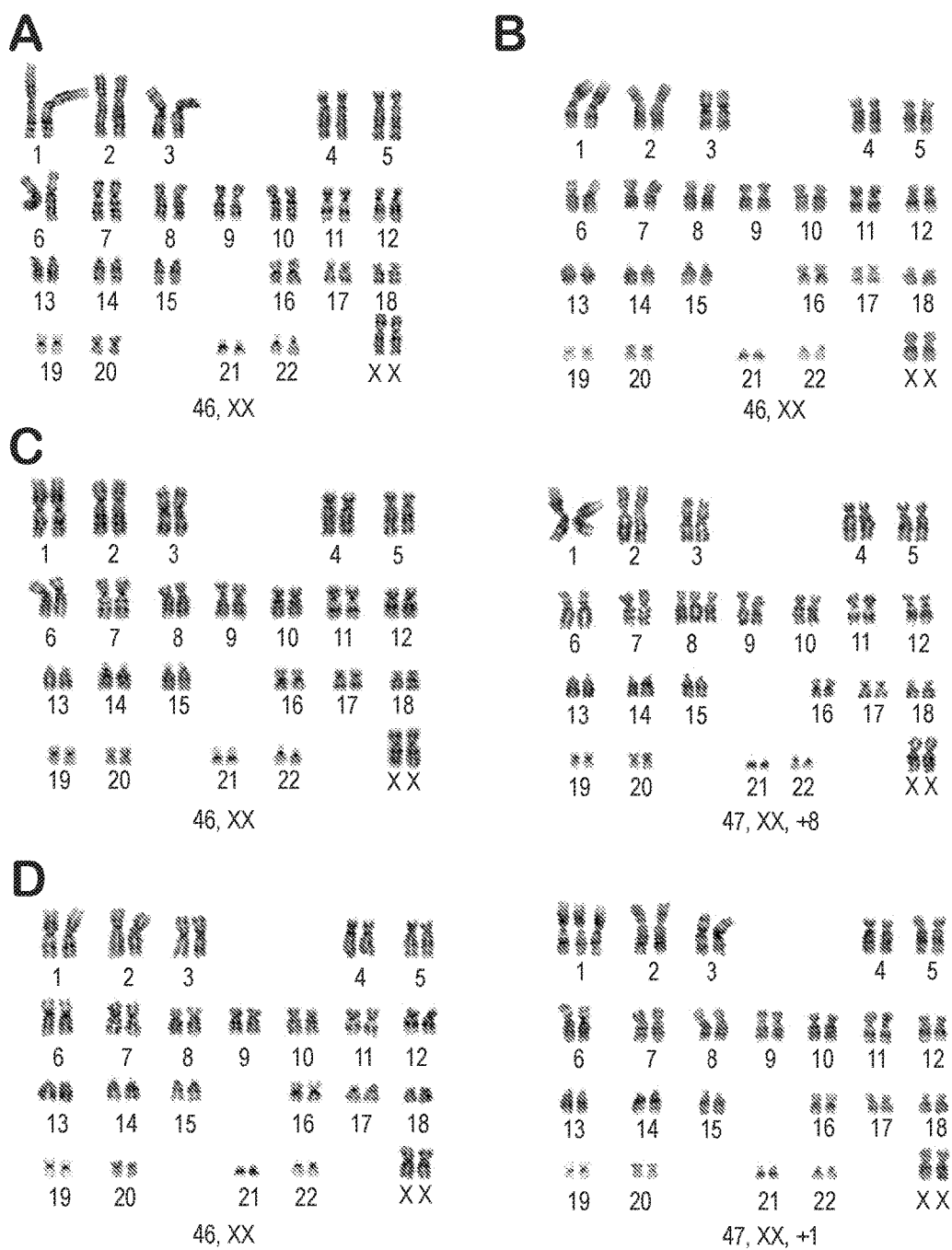
FIG. 9 shows the G-banded karyotyping of the human HLA homozygous parthenogenetic stem cell lines: hpSC-Hhom-1 (A) and hpSC-Hhom-4 (B) lines have a normal 46,XX karyotype; the hpSC-Hhom-2(C) line has 15% cells with 47,XX,+8 karyotype-aneuploidy of chromosome 8; the hpSC-Hhom-3(D) line has 4.2% cells with 47,XX, +1 karyotype-aneuploidy of chromosome 1.

G-banded karyotyping demonstrated that hpSC-Hhom-1 and hpSC-Hhom-4 lines had a normal human 46, XX karyotype (FIGS. 9, A and B). The hpSC-Hhom-2 and hpSC-Hhom-3 lines, both derived from a single donor, displayed karyotype anomalies. Approximately 15% of cells from the hpSC-Hhom-2 line exhibited aneuploidy of chromosome 8: 47, XX, +8 karyotype (FIG. 9, C) and 4.2% of cells from hpSC-Hhom-3 line exhibited aneuploidy of chromosome 1: 47, XX, +1 karyotype (FIG. 9, D). No X chromosome heteromorphism for any cell line was observed in the analysis of 100 metaphases. (FIG. 9).

Figure 10:
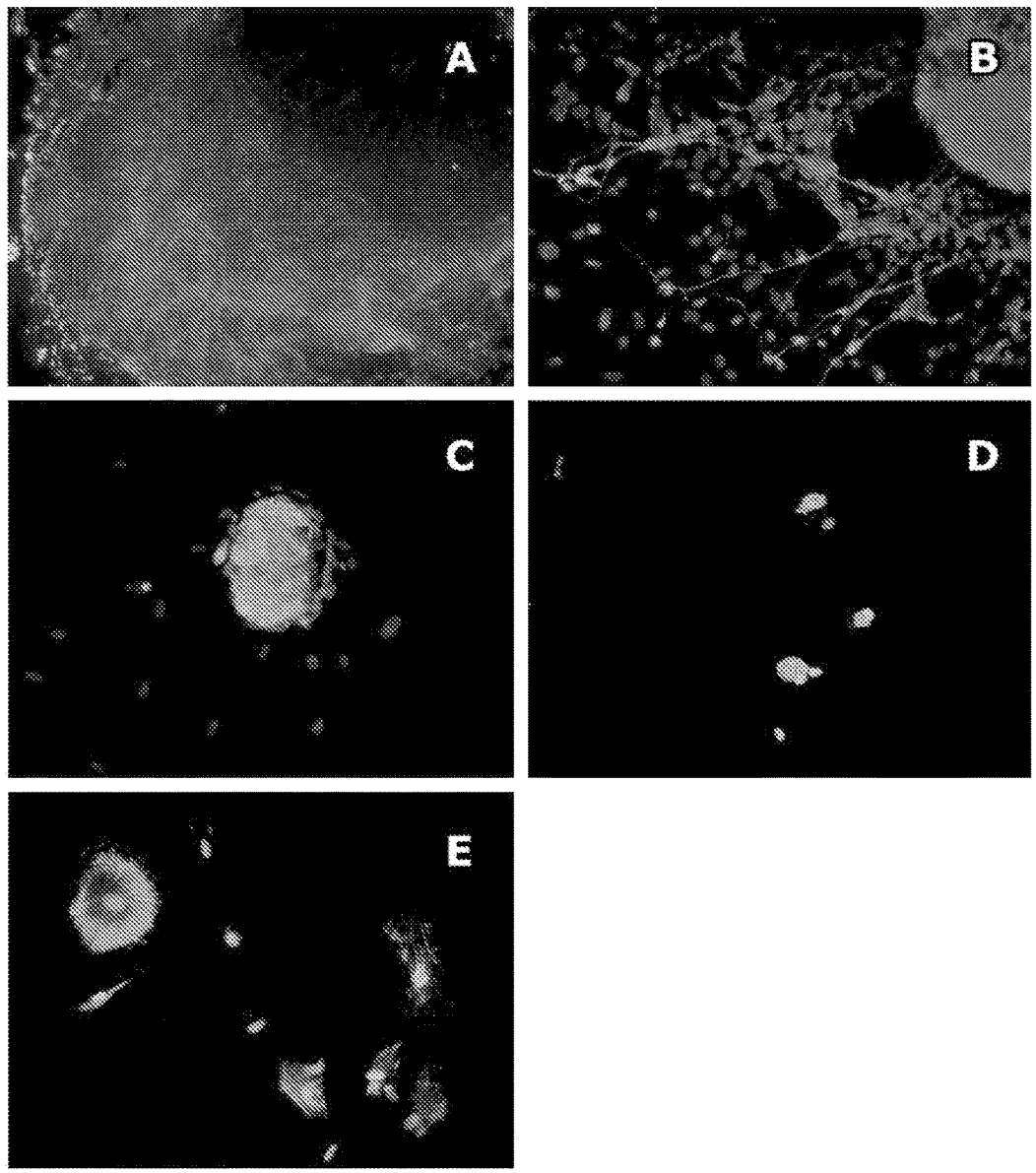
FIG. 10 shows the in vitro differentiation of hpSC-Hhom-4 into derivatives from all three germ layers: Ectoderm differentiation is evident as positive immunocytochemical staining for neuron specific markers neurofilament 68 (A) and NCAM (B); Endoderm differentiation is evident as positive staining for alpha-fetoprotein (C); Differentiated cells were positive for mesoderm markers muscle specific desmin (D) and alpha-actinin (E); Magnification ×200 (A-E).

The hpSC-Hhom-4 line remained undifferentiated over 27 passages. The other cell lines were successfully cultured over at least 21 passages. The cells from hpSC-Hhom-4 line formed cystic embryoid bodies in suspension culture and gave rise to derivatives from all three germ layers—ectoderm, mesoderm and endoderm—following differentiation in vitro (FIG. 10). Ectoderm differentiation was confirmed by positive immunocytochemical staining for neuron specific markers neurofilament 68 (FIG. 10A) and NCAM (FIG. 10B). Differentiated cells were also positive for mesoderm muscle specific markers desmin (FIG. 10C) and alpha-actinin (FIG. 10D). Endoderm differentiation was confirmed by positive staining for alpha-fetoprotein (FIG. 10E).

Figure 11:
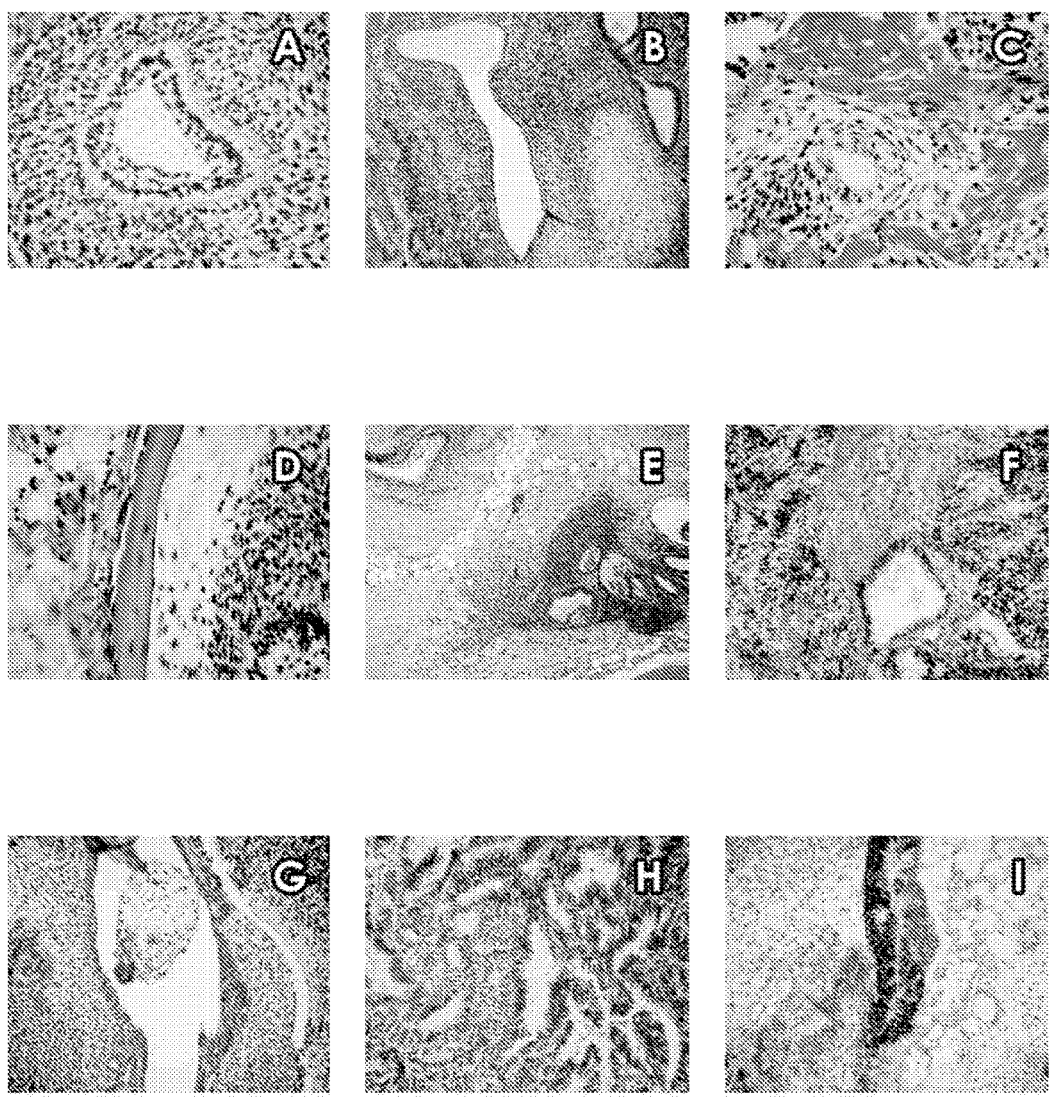
FIG. 11 shows the in vivo differentiation of hpSC-Hhom-4. Teratoma formation in SCID mice Derivatives from all three embryonic germ layers (ectoderm, endoderm and mesoderm): Well-formed respiratory-type glands surrounded by mesenchymal cells, hematoxylin/eosin (h/e) staining, magnification ×140 (A); Likely neural tube with a single-layer of cells; to the right an endodermal gland and at the bottom chondro-differentiation, h/e staining, magnification ×70 (B); Bone surrounded by mesenchymal cells, in the center is a tubular gland with cuboid epithelium, picrofucsin staining, magnification ×140 (C); Well-formed bone surrounded by mesenchymal cells and fat tissue, h/e staining, magnification ×140 (D); On the left are endodermal glands; mesodermal and fat tissue, collagen; bone is seen on the right and at the bottom, Kraberg staining, magnification ×70 (E); An endoderm glandular structure surrounded by mesenchymal cells, a high production of collagen fibers, Van Gieson staining, magnification ×280 (F); Stratified epithelium, in the center a hyperkeratotic pearl, on the left another gland, h/e staining, magnification ×140 (G); A colony of glands, h/e staining, magnification ×70 (H); Glands containing cells producing a brown pigment, possibly biliary pigment, surrounded by fat tissue and mesenchymal cells, h/e staining, magnification ×140 (I).

The ability of all hpSC-Hhom lines to form derivatives from all three germ layers was furthermore investigated in vivo by subcutaneous injection of hpSC-Hhom cells into immunodeficient mice (FIG. 11). All hpSC-Hhom lines were capable of forming teratomas approximately two months following injection. Teratocarcinoma formation was not observed. Approximately four million mitomycin-C treated human fibroblasts used as feeder layers for the hpSC-Hhom cells were also injected as controls and did not exhibit teratoma growth.

Histological examination of cell transplants demonstrated the presence of organized structures including: various gland types (some producing a brown pigment, possibly biliary pigment), chondro-differentiation, well-formed bones, mesenchymal cells, a high production of collagen fibers, fat tissue, neural tubes and stratified pavement epithelium with parakeratosis-pearls (FIG. 11). These findings suggest that hpSC-Hhom will differentiate in vivo into tissues derived from all three germ layers.

Although the invention has been described with reference to the above examples, it will be understood that modifications and variations are encompassed within the spirit and scope of the invention. Accordingly, the invention is limited only by the following claims.

What is claimed is:

1. A method of generating HLA homozygous stem cells comprising:
    a) screening oocyte donors for HLA-haplotypes found commonly in a given population group;
    b) parthenogenetically activating a human oocyte from (a), by:
        i) contacting the oocyte with an ionophore at high $O_2$ tension; and
        ii) contacting the oocyte with a serine-threonine kinase inhibitor under low $O_2$ tension;
    c) cultivating the activated oocyte of (b) at low $O_2$ tension until blastocyst formation;
    d) transferring the blastocyst to a layer of feeder cells and culturing the transferred blastocyst under high $O_2$ tension;
    e) isolating an inner cell mass (ICM) from the blastocyst of (c); and
    f) culturing the cells of the ICM of (d) on a layer of feeder cells under high $O_2$ tension, thereby producing HLA homozygous stem cells.

2. The method of claim 1, further comprising HLA-typing of the biological parents of the oocyte donor or step (a).

3. The method of claim 1, wherein the ionophore is selected from the group consisting of ionomycin or A23187.

4. The method of claim 1, wherein the serine-threonine kinase inhibitor is selected from the group consisting of staurosporine, 2-aminopurine, sphingosine, and 6-dimethylaminopurine (DMAP).

5. The method of claim 1, wherein low $O_2$ tension is maintained by incubation in a gas mixture environment comprising an $O_2$ concentration of about 2% $O_2$ to about 5% $O_2$.

6. The method of claim 1, wherein high $O_2$ tension is maintained by incubation in a gas mixture environment comprising an $O_2$ concentration of about 5% $O_2$ to about 20% $O_2$.

7. The method of claim 1, wherein the layer of feeder cells comprises human fibroblasts.

8. The method of claim 7, wherein the fibroblasts are postnatal human dermal fibroblasts.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Artificial sequence
<220> FEATURE:
<223> OTHER INFORMATION: Primer

<400> SEQUENCE: 1
gctcttcatg gtcatgttct cca                                           23

```
<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
ggagcagtgg ttgtacagag g                                      21

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
tacaaccact gcactacctg                                        20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tggccatgaa gatggagtcg                                        20

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
gagtcctgta ggcaaggtct tacct                                  25

<210> SEQ ID NO 6
<211> LENGTH: 25
<212> TYPE: DNA
<213> ORGANISM: Artificial sequence
<220> FEATURE:
<223> OTHER INFORMATION: Primer

<400> SEQUENCE: 6
cttgcctgaa gacttccatg agtga                                  25

<210> SEQ ID NO 7
<211> LENGTH: 25
<212> TYPE: DNA
<213> ORGANISM: Artificial sequence
<220> FEATURE:
<223> OTHER INFORMATION: Primer

<400> SEQUENCE: 7
gctgctggcc agctctgcac ggctg                                  25

<210> SEQ ID NO 8
<211> LENGTH: 25
<212> TYPE: DNA
<213> ORGANISM: Artificial sequence
<220> FEATURE:
<223> OTHER INFORMATION: Primer
```

```
<400> SEQUENCE: 8
cttgcctgaa gacttccatg agtga                                           25

<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9
cttagctgag acaccaagag g                                               21

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
gcagcatctt gctactcttg c                                               21

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
accacagtcc atgccatcac                                                 20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
tccaccaccc tgttgctgta                                                 20
```